(12) United States Patent
Durfee et al.

(10) Patent No.: US 11,672,866 B2
(45) Date of Patent: Jun. 13, 2023

(54) OSTEOTROPIC NANOPARTICLES FOR PREVENTION OR TREATMENT OF BONE METASTASES

(71) Applicants: Paul N. Durfee, Albuquerque, NM (US); Charles Jeffrey Brinker, Albuquerque, NM (US); Yu-Shen Lin, Seattle, WA (US); Hon Leong, London (CA)

(72) Inventors: Paul N. Durfee, Albuquerque, NM (US); Charles Jeffrey Brinker, Albuquerque, NM (US); Yu-Shen Lin, Seattle, WA (US); Hon Leong, London (CA)

(*) Notice: Subject to any disclaimer, the term of this patent is extended or adjusted under 35 U.S.C. 154(b) by 166 days.

(21) Appl. No.: 16/068,235

(22) PCT Filed: Jan. 6, 2017

(86) PCT No.: PCT/US2017/012583
§ 371 (c)(1),
(2) Date: Jul. 5, 2018

(87) PCT Pub. No.: WO2017/120504
PCT Pub. Date: Jul. 13, 2017

(65) Prior Publication Data
US 2019/0022235 A1    Jan. 24, 2019

Related U.S. Application Data

(60) Provisional application No. 62/395,196, filed on Sep. 15, 2016, provisional application No. 62/276,388, (Continued)

(51) Int. Cl.
*A61K 47/54* (2017.01)
*A61K 9/51* (2006.01)
(Continued)

(52) U.S. Cl.
CPC ........... *A61K 47/548* (2017.08); *A61K 9/16* (2013.01); *A61K 9/5115* (2013.01); (Continued)

(58) Field of Classification Search
CPC .................................................. A61K 47/548
See application file for complete search history.

(56) References Cited

U.S. PATENT DOCUMENTS 4,927,637 A    5/1990  Morano et al.
5,057,296 A   10/1991  Beck
(Continued)

FOREIGN PATENT DOCUMENTS

EP    1852393 A1    11/2007
JP    2009515520 A    4/2009
(Continued)

OTHER PUBLICATIONS

G Wang, NZ Mostafa, V Incani, C Kucharski, H Uludag. "Bisphosphonate-decorated lipid nanoparticles designed as drug carriers for bone diseases." Journal of Biomedical Materials Research A, vol. 100A Issue 3 Mar. 2012, pp. 684-693, published online Dec. 30, 2011. (Year: 2011).*

(Continued)

*Primary Examiner* — Isaac Shomer
(74) *Attorney, Agent, or Firm* — Schwegman Lundberg & Woessner, P.A.

(57) ABSTRACT

The present disclosure is directed to protocells or nanoparticles, which are optionally coated with a lipid bilayer, which can be used for targeting bone tissue for the delivery of bioactive agents useful in the treatment and/or diagnosis of bone cancer, often metastatic bone cancer which often occurs secondary to a primary cancer such as prostate cancer, breast cancer, lung cancer and ovarian cancer, among numerous others. These protocells or nanoparticles target (Continued)

- Steric barrier
  - PEG

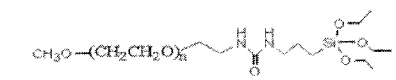

PEG silane MW 550 – 5000 g/mol

- Zwitterionic coating

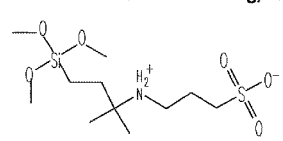

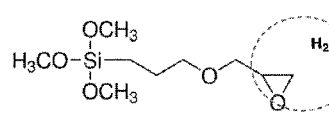

3-{[DIMETHYL(3-TRIMETHOXYSILYL)PROPYL]AMMONIO}PROPANE-1-SULFONATE
MW = 329.485 g/mol

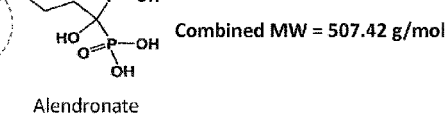

Combined MW = 507.42 g/mol (3-Glycidyloxypropyl)trimethoxysilane    Alendronate bone cancer especially metastatic bone cancer with bioactive agents including anticancer agents and/or diagnostic agents for purposes of treating, diagnosing and/or monitoring the therapy of the bone cancer. Osteotropic protocells or nanoparticles, pharmaceutical compositions comprising a population of osteotropic protocells or nanoparticles and methods of diagnosing, treating and/or monitoring therapy of bone cancer are representative aspects.

11 Claims, 28 Drawing Sheets

Specification includes a Sequence Listing.

Related U.S. Application Data filed on Jan. 8, 2016, provisional application No. 62/276,297, filed on Jan. 8, 2016.

(51) Int. Cl.

| | |
|---|---|
| *A61P 35/00* | (2006.01) |
| *A61K 9/16* | (2006.01) |
| *B82Y 5/00* | (2011.01) |
| *A61K 47/69* | (2017.01) |
| *C12N 15/88* | (2006.01) |
| *A61K 47/10* | (2017.01) |
| *A61K 45/06* | (2006.01) |

(52) U.S. Cl.
CPC .......... *A61K 9/5123* (2013.01); *A61K 9/5192* (2013.01); *A61K 47/10* (2013.01); *A61K 47/6923* (2017.08); *A61P 35/00* (2018.01); *C12N 15/88* (2013.01); *A61K 45/06* (2013.01); *A61K 2300/00* (2013.01); *B82Y 5/00* (2013.01)

(56) References Cited

U.S. PATENT DOCUMENTS

| | | | |
|---|---|---|---|
| 5,098,684 A | 3/1992 | Kresge et al. | |
| 5,360,834 A | 11/1994 | Popall et al. | |
| 5,689,574 A | 11/1997 | Heirich et al. | |
| 5,789,230 A | 8/1998 | Cotten | |
| 6,194,388 B1 | 2/2001 | Krieg et al. | |
| 6,365,266 B1 | 4/2002 | MacDougall et al. | |
| 6,387,453 B1 | 5/2002 | Brinker et al. | |
| 6,808,867 B2 | 10/2004 | Doshi et al. | |
| 6,913,832 B2 | 7/2005 | Fan et al. | |
| 7,101,967 B2 | 9/2006 | Fischer et al. | |
| 7,332,264 B2 | 2/2008 | Doshi et al. | |
| 7,514,267 B1 | 4/2009 | Lopez et al. | |
| 7,563,451 B2 | 7/2009 | Lin et al. | |
| 8,268,962 B2 | 9/2012 | Heemskerk et al. | |
| 8,374,816 B2 | 2/2013 | Vu | |
| 8,734,816 B2 | 5/2014 | Liu et al. | |
| 8,926,994 B2 | 1/2015 | Serda et al. | |
| 8,992,984 B1 | 3/2015 | Brinker et al. | |
| 9,480,653 B2 | 11/2016 | Brinker et al. | |
| 9,579,283 B2 | 2/2017 | Brinker et al. | |
| 9,855,217 B2 | 1/2018 | Brinker et al. | |
| 9,989,447 B1 | 6/2018 | Kaehr et al. | |
| 10,022,327 B2 | 7/2018 | Brinker et al. | |
| 10,465,189 B2 | 11/2019 | Venkatraman et al. | |
| 11,344,629 B2 | 5/2022 | Brinker et al. | |
| 2002/0147105 A1 | 10/2002 | Shamshoum et al. | |
| 2004/0005352 A1 | 1/2004 | Lopez et al. | |
| 2004/0258671 A1 | 12/2004 | Watkins | |
| 2005/0239687 A1 | 10/2005 | Divita et al. | |
| 2006/0154069 A1 | 7/2006 | Lin et al. | |
| 2007/0224257 A1 | 9/2007 | Commander et al. | |
| 2007/0287104 A1 | 12/2007 | Doshi et al. | |
| 2008/0095852 A1 | 4/2008 | Kong et al. | |
| 2008/0160313 A1 | 7/2008 | Lopez et al. | |
| 2008/0213377 A1 | 9/2008 | Bhatia et al. | |
| 2008/0241262 A1 | 10/2008 | Lee et al. | |
| 2008/0241917 A1 | 10/2008 | Akita et al. | |
| 2008/0286371 A1 | 11/2008 | Pacheco et al. | |
| 2009/0054246 A1 | 2/2009 | Peabody et al. | |
| 2009/0181090 A1 | 7/2009 | Dreis et al. | |
| 2009/0208563 A1 | 8/2009 | Watkins et al. | |
| 2009/0305409 A1 | 12/2009 | Kogure et al. | |
| 2010/0028341 A1 | 2/2010 | Hermans et al. | |
| 2010/0055167 A1 | 3/2010 | Zhang et al. | |
| 2010/0152699 A1 | 6/2010 | Ferrari et al. | |
| 2010/0166665 A1* | 7/2010 | Butts .............. A61K 49/0428 424/9.32 |
| 2010/0168120 A1 | 7/2010 | Watterson et al. | |
| 2010/0255103 A1 | 10/2010 | Liong et al. | |
| 2011/0059156 A9 | 3/2011 | Mirkin et al. | |
| 2011/0097819 A1 | 4/2011 | Groves et al. | |
| 2011/0135571 A1 | 6/2011 | Lin et al. | |
| 2011/0230372 A1 | 9/2011 | Willman et al. | |
| 2011/0268791 A1 | 11/2011 | Liu et al. | |
| 2011/0300186 A1 | 12/2011 | Hellstrom et al. | |
| 2012/0207795 A1 | 8/2012 | Zink et al. | |
| 2013/0095039 A1 | 4/2013 | Lu et al. | |
| 2013/0108661 A1 | 5/2013 | Blander et al. | |
| 2013/0115169 A1 | 5/2013 | Lahann et al. | |
| 2013/0122054 A1 | 5/2013 | Harashima et al. | |
| 2013/0185823 A1 | 7/2013 | Kuang et al. | |
| 2013/0195963 A1 | 8/2013 | Serda et al. | |
| 2013/0197103 A1 | 8/2013 | Brown | |
| 2014/0023700 A1 | 1/2014 | Knudsen et al. | |
| 2014/0079774 A1* | 3/2014 | Brinker .............. C07K 14/47 424/450 |
| 2014/0141089 A1 | 5/2014 | Liang | |
| 2014/0212479 A1 | 7/2014 | Zeinelden | |
| 2014/0234210 A1* | 8/2014 | Lin .................. A61K 49/00 424/1.21 |
| 2014/0301951 A1 | 10/2014 | Liu et al. | |
| 2015/0010475 A1 | 1/2015 | Brinker et al. | |
| 2015/0118247 A1 | 4/2015 | Hotson et al. | |
| 2015/0125391 A1* | 5/2015 | Swami .............. A61K 47/548 424/9.1 |
| 2015/0164798 A1 | 6/2015 | Brinker et al. | |
| 2015/0272885 A1 | 10/2015 | Ashley et al. | |
| 2015/0320681 A1 | 11/2015 | Brinker et al. | |
| 2016/0090603 A1 | 3/2016 | Carnes et al. | |
| 2016/0106671 A1 | 4/2016 | Brinker et al. | |
| 2016/0151482 A1 | 6/2016 | Carnes et al. | |
| 2016/0193588 A1 | 7/2016 | Haynes et al. | |
| 2016/0287717 A1 | 10/2016 | Brinker | |
| 2016/0338954 A1 | 11/2016 | Brinker | |
| 2016/0361411 A1 | 12/2016 | Gindy et al. | |
| 2017/0165375 A1 | 6/2017 | Ashley et al. | |
| 2017/0232115 A1 | 8/2017 | Ashley et al. | |
| 2018/0028686 A1 | 2/2018 | Brinker et al. | |
| 2018/0049984 A1 | 2/2018 | Brinker et al. | |
| 2018/0105430 A1 | 4/2018 | Carnes et al. | |
| 2018/0110831 A1 | 4/2018 | Brinker et al. | |
| 2018/0344641 A1 | 12/2018 | Brinker et al. | |
| 2019/0091150 A1 | 3/2019 | Brinker et al. | |
| 2019/0262469 A1 | 8/2019 | Brinker et al. | |
| 2020/0009264 A1 | 1/2020 | Brinker et al. | |
| 2020/0197536 A1 | 6/2020 | Brinker et al. | |
| 2020/0375912 A1 | 12/2020 | Serda et al. | |
| 2020/0405650 A1 | 12/2020 | Noureddine et al. | |
| 2021/0030675 A1 | 2/2021 | Brinker et al. | |
| 2021/0315822 A1 | 10/2021 | Guo et al. | |
| 2022/0033767 A1 | 2/2022 | Guo et al. | |
| 2022/0033768 A1 | 2/2022 | Guo et al. | |
| 2022/0151924 A1 | 5/2022 | Brinker et al. | |

FOREIGN PATENT DOCUMENTS

| | | |
|---|---|---|
| WO | WO-9747296 A2 | 12/1997 |
| WO | WO-0076556 A2 | 12/2000 |
| WO | WO-02066506 A2 | 8/2002 |
| WO | WO-03055469 A1 | 7/2003 |
| WO | WO-2004096140 A2 | 11/2004 |
| WO | WO-2005009602 A2 | 3/2005 |

(56) References Cited

FOREIGN PATENT DOCUMENTS

| | | |
|---|---|---|
| WO | WO-2005084710 A2 | 9/2005 |
| WO | WO-2007140618 A1 | 12/2007 |
| WO | WO-2009051837 A2 | 4/2009 |
| WO | WO-2010035304 A2 | 4/2010 |
| WO | WO-2010048572 A1 | 4/2010 |
| WO | WO-2010078569 A2 | 7/2010 |
| WO | WO-2011116219 A1 | 9/2011 |
| WO | WO-2011116226 A2 | 9/2011 |
| WO | WO-2011150264 A2 | 12/2011 |
| WO | WO-2012149376 A2 | 11/2012 |
| WO | WO-2013012891 A1 | 1/2013 |
| WO | WO-2013056132 A2 | 4/2013 |
| WO | WO-2013082612 A1 | 6/2013 |
| WO | WO-2013103614 A1 | 7/2013 |
| WO | WO-2014093635 A1 | 6/2014 |
| WO | WO-2014165608 A1 | 10/2014 |
| WO | WO-2014165617 A1 | 10/2014 |
| WO | WO-2015042268 A1 | 3/2015 |
| WO | WO-2015042279 A1 | 3/2015 |
| WO | WO-2015095340 A1 | 6/2015 |
| WO | 2015130584 | 9/2015 |
| WO | WO-2016145031 A1 | 9/2016 |
| WO | WO-2016145335 A1 | 9/2016 |
| WO | WO-2017041032 A1 | 3/2017 |
| WO | WO-2017041033 A1 | 3/2017 |
| WO | WO-2017120504 A1 | 7/2017 |
| WO | WO-2018000043 A1 | 1/2018 |
| WO | WO-2018160865 | 9/2018 |
| WO | WO-2018187287 A1 | 10/2018 |
| WO | WO-2019028387 A1 | 2/2019 |
| WO | WO-2019169152 A1 | 9/2019 |
| WO | WO-2020028342 A1 | 2/2020 |
| WO | WO-2020068798 A1 | 4/2020 |
| WO | WO-2020068806 A1 | 4/2020 |
| WO | WO-2020176716 A1 | 9/2020 |

OTHER PUBLICATIONS

Wenyi Gu, Chengtie Wu, Jiezhong Chen, Yin Xiao. "Nanotechnology in the targeted drug delivery for bone diseases and bone regeneration." International Journal of Nanomedicine, vol. 8, 2013, pp. 2305-2317. (Year: 2013).*

Tejinder Singh, Veerpal Kaur, Manish Kumar, Prabhjot Kaur, R. S. R. Murthy, and Ravindra K. Rawal. "The critical role of bisphosphonates to target bone cancer metastasis: an overview." Journal of Drug Targeting, vol. 23(1), 2015, pp. 1-15, available online Sep. 9, 2014. (Year: 2014).*

Lingxiang Wu et al. "Synthesis of a Zwitterionic Silane and Its Application in the Surface Modification of Silicon-Based Material Surfaces for Improved Hemocompatibility." ACS Applied Materials & Interfaces, vol. 2 No. 10, 2010, pp. 2781-2788. (Year: 2010).*

Satoshi Yamamoto, Satomi Takao, Shinji Muraishi, Cheng Xu, Minoru Taya. "Synthesis of Fe70Pd30 nanoparticles and their surface modification by zwitterionic linker." Materials Chemistry and Physics 234 (2019) 237-244. (Year: 2019).*

N. S. Einkolopiyan. "New Aspects of the Nucleophilic Opening of Epoxide Rings." Pure & Applied Chemistry, vol. 48, Perpmon Pross, 1976, pp. 317-328. (Year: 1976).*

Rosario Pignatello et al. "A novel biomaterial for osteotropic drug nanocarriers: synthesis and biocompatibility evaluation of a PLGA-ALE conjugate." Nanomedicine, vol. 4(2), 2009, pp. 161-175. (Year: 2009).*

Francisco Balas et al. "Confinement and Controlled Release of Bisphosphonates on Ordered Mesoporous Silica-Based Materials." Journal of the American Chemical Society, vol. 128, 2006, pp. 8116-8117. (Year: 2006).*

"International Application Serial No. PCT/US2017/012583, International Preliminary Report on Patentability dated Jul. 19, 2018", 7 pgs.

Ashley, C E, et al., "The targeted delivery of multicomponent cargos to cancer cells by nanoporous particle-supported lipid bilayers", Nature Materials, No. 5. vol. 10, (Apr. 17, 2011), 389-397.

Russell, R G et al., "Bisphosphonates: An Update on Mechanisms of Action and How These Relate to Clinical Efficacy", Ann NY Acad Sci 1117, (2007), 209-257.

Tran, Chris, et al., "Development of a second-generation antiandrogen for treatment of advanced prostate cancer", Science 324(5928), (2009), 787-790.

"International Application Serial No. PCT/US2017/012583, International Search Report dated Apr. 20, 2017", 3 pgs.

"International Application Serial No. PCT/US2017/012583, Written Opinion dated Apr. 20, 2017", 5 pgs.

Liu, Juewen, et al., "Porous Nanoparticle Supported Lipid Bilayers (Protocells) as Delivery Vehicles", J. Am. Chem. Soc., vol. 131, No. 4, (2009), 7 pgs.

"U.S. Appl. No. 10/100,108, Non Final Office Action dated Jan. 22, 2004", 8 pgs.

"U.S. Appl. No. 10/100,108, Notice of Allowance dated Jul. 13, 2004", 10 pgs.

"U.S. Appl. No. 10/100,108, Response filed Apr. 21, 2004 to Non Final Office Action dated Jan. 22, 2004", 9 pgs.

"U.S. Appl. No. 10/163,425, Advisory Action dated Jul. 2, 2004".

"U.S. Appl. No. 10/163,425, Examiner Interview Summary filed Mar. 29, 2005", 9 pgs.

"U.S. Appl. No. 10/163,425, Final Office Action dated Mar. 31, 2004", 8 pgs.

"U.S. Appl. No. 10/163,425, Non Final Office Action dated Aug. 1, 2003", 10 pgs.

"U.S. Appl. No. 10/163,425, Non Final Office Action dated Sep. 22, 2004", 6 pgs.

"U.S. Appl. No. 10/163,425, Notice of Allowance dated Feb. 10, 2005", 8 pgs.

"U.S. Appl. No. 10/163,425, Response filed Jan. 2, 2004 to Non Final Office Action dated Aug. 1, 2003", 13 pgs.

"U.S. Appl. No. 10/163,425, Response filed May 28, 2004 to Final Office Action dated Mar. 31, 2004", 15 pgs.

"U.S. Appl. No. 10/163,425, Response filed Jul. 23, 2004 to Advisory Action dated Jul. 2, 2004", 15 pgs.

"U.S. Appl. No. 10/163,425, Response filed Dec. 22, 2004 to Non Final Office Action dated Sep. 22, 2004", 11 pgs.

"U.S. Appl. No. 10/373,565, Notice of Allowance dated Sep. 11, 2007", 4 pgs.

"U.S. Appl. No. 12/903,577, Advisory Action dated Mar. 20, 2012", 3 pgs.

"U.S. Appl. No. 12/903,577, Advisory Action dated Jun. 7, 2017", 2 pgs.

"U.S. Appl. No. 12/903,577, Final Office Action dated May 8, 2015", 19 pgs

"U.S. Appl. No. 12/903,577, Final Office Action dated Nov. 30, 2011", 19 pgs.

"U.S. Appl. No. 12/903,577, Non Final Office Action dated Jun. 3, 2014", 16 pgs.

"U.S. Appl. No. 12/903,577, Non Final Office Action dated Jun. 30, 2011", 13 pgs.

"U.S. Appl. No. 12/903,577, Non Final Office Action dated Oct. 25, 2017", 16 pgs.

"U.S. Appl. No. 12/903,577, Notice of Non-Compliant Amendment dated Feb. 4, 2015", 5 pgs.

"U.S. Appl. No. 12/903,577, Response filed Jan. 20, 2016 to Final Office Action dated May 8, 2015", 7 pgs.

"U.S. Appl. No. 12/903,577, Response filed Feb. 26, 2015 to Notice of Non-Compliant Amendment dated Feb. 4, 2015", 5 pgs.

"U.S. Appl. No. 12/903,577, Response filed Mar. 9, 2012 to Final Office Action dated Nov. 30, 2011", 22 pgs.

"U.S. Appl. No. 12/903,577, Response filed Jun. 1, 2011 to Restriction Requirement dated May 13, 2011", 2 pgs.

"U.S. Appl. No. 12/903,577, Response filed Jul. 12, 2017 to Advisory Action dated Jul. 7, 2017", 7 pgs.

"U.S. Appl. No. 12/903,577, Response filed Sep. 30, 2011 to Non Final Office Action dated Jun. 30, 2011", 9 pgs.

"U.S. Appl. No. 12/903,577, Response filed Dec. 3, 2014 to Non Final Office Action dated Jun. 3, 2014", 15 pgs.

"U.S. Appl. No. 12/903,577, Restriction Requirement dated May 13, 2011", 10 pgs.

(56) References Cited

OTHER PUBLICATIONS

"U.S. Appl. No. 13/143,164, 312 Amendment filed Mar. 27, 2014", 5 pgs.
"U.S, Appl. No. 13/143,164, Final Office Action dated Jun. 26, 2013", 14 pgs.
"U.S. Appl. No. 13/143,164, Non Final Office Action dated Jan. 11, 2013", 12 pgs.
"U.S. Appl. No. 13/143,164, Notice of Allowance dated Jan. 13, 2014", 7 pgs.
"U.S. Appl. No. 13/143,164, Response filed Apr. 10, 2013 to Non Final Office Action dated Jan. 11, 2013", 13 pgs.
"U.S. Appl. No. 13/143,164, Response filed Nov. 7, 2012 to Restriction Requirement dated Oct. 10, 2012", 4 pgs.
"U.S. Appl. No. 13/143,164, Response filed Nov. 26, 2013 to Final Office Action dated Jun. 26, 2013", 18 pgs.
"U.S. Appl. No. 13/143,164, Restriction Requirement dated Oct. 10, 2012", 11 pgs.
"U.S. Appl. No. 14/113,371, 312 Amendment filed Dec. 21, 2016", 4 pgs.
"U.S. Appl. No. 14/113,371, Amendment filed Sep. 23, 2016", 16 pgs.
"U.S. Appl. No. 14/113,371, Examiner Interview Summary dated Mar. 25, 2016", 1 pg.
"U.S. Appl. No. 14/113,371, Final Office Action dated Feb. 1, 2016", 15 pgs.
"U.S. Appl. No. 14/113,371, Final Office Action dated Mar. 25, 2016", 13 pgs.
"U.S. Appl. No. 14/113,371, Non Final Office Action dated Jul. 13, 2015", 14 pgs.
"U.S. Appl. No. 14/113,371, Non Final Office Action dated Dec. 17, 2014", 15 pgs.
"U.S. Appl. No. 14/113,371, Notice of Allowability dated Jan. 31, 2017", 4 pgs.
"U.S. Appl. No. 14/113,371, Notice of Allowance dated Oct. 11, 2016", 9 pgs.
"U.S. Appl. No. 14/113,371, Preliminary Amendment filed Oct. 22, 2013", 14 pgs.
"U.S. Appl. No. 14/113,371, Response filed Apr. 16, 2015 to Non Final Office Action dated Dec. 17-1", 23 pgs.
"U.S. Appl. No. 14/113,371, Response filed Aug. 25, 2016 to Final Office Action dated Mar. 25, 2016", 17 pgs.
"U.S. Appl. No. 14/113,371, Response filed Oct. 17, 2014 to Restriction Requirement dated Aug. 18, 2014", 19 pgs.
"U.S. Appl. No. 14/113,371, Response filed Nov. 4, 2015 to Non Final Office Action dated Jul. 13, 2015", 25 pgs.
"U.S. Appl. No. 14/113,371, Response filed Sep. 26, 2016 to Final Office Action dated Mar. 25, 2016", 16 pgs.
"U.S. Appl. No. 14/113,371, Restriction Requirement dated Aug. 18, 2014", 12 pgs.
"U.S. Appl. No. 14/253,030, Advisory Action dated Apr. 11, 2018", 25 pgs.
"U.S. Appl. No. 14/253,030, Advisory Action dated Sep. 5, 2017", 22 pgs.
"U.S. Appl. No. 14/253,030, Advisory Action dated Sep. 9, 2016", 16 pgs.
"U.S. Appl. No. 14/253,030, Declaration under 37 C.F.R 1.132 filed Mar. 27, 2018", 4 pgs.
"U.S. Appl. No. 14/253,030, Final Office Action dated May 11, 2016", 15 pgs.
"U.S. Appl. No. 14/253,030, Final Office Action dated Jun. 9, 2017", 19 pgs.
"U.S. Appl. No. 14/253,030, Final Office Action dated Dec. 1, 2017", 21 pgs.
"U.S. Appl. No. 14/253,030, Non Final Office Action dated Dec. 9, 2016", 19 pgs.
"U.S. Appl. No. 14/253,030, Non Final Office Action dated Dec. 10, 2015", 14 pgs.
"U.S. Appl. No. 14/253,030, Preliminary Amendment filed Jul. 1, 2015", 8 pgs.
"U.S. Appl. No. 14/253,030, Preliminary Amendment filed Dec. 9, 2014", 3 pgs.
"U.S. Appl. No. 14/253,030, Response filed Mar. 10, 2016 to Non Final Office Action dated Dec. 10, 2015", 11 pgs.
"U.S. Appl. No. 14/253,030, Response filed Aug. 11, 2016 to Final Office Action dated May 11, 2016", 9 pgs.
"U.S. Appl. No. 14/253,030, Response filed Oct. 10, 2017 to Advisory Action dated Sep. 5, 2017", 12 pgs.
"U.S. Appl. No. 14/253,030, Response filed Oct. 11, 2016 to Advisory Action dated Sep. 9, 2016", 9 pgs.
"U.S. Appl. No. 14/253,030, Response filed Nov. 2, 2015 to Restriction Requirement dated Oct. 6, 2015", 4 pgs.
"U.S. Appl. No. 14/253,030, Response filed Apr. 2, 2018 to Final Office Action dated Dec. 1, 2017", 10 pgs.
"U.S. Appl. No. 14/253,030, Response filed May 9, 2017 to Non-Final Office Action dated Dec. 9, 2016", 8 pgs.
"U.S. Appl. No. 14/253,030, Response filed Aug. 10, 2017 to Final Office Action dated Jun. 9, 2017", 12 pgs.
"U.S. Appl. No. 14/253,030, Restriction Requirement dated Sep. 17, 2015", 7 pgs.
"U.S. Appl. No. 14/253,030, Restriction Requirement dated Oct. 6, 2015", 7 pgs.
"U.S. Appl. No. 14/253,030, Supplemental Declaration under 37 C.F.R. 1.132 filed Aug. 7, 2017", 2 pgs.
"U.S. Appl. No. 14/350,674, Non Final Office Action dated Jun. 17, 2016", 19 pgs.
"U.S. Appl. No. 14/350,674, Preliminary Amendment filed Jun. 4, 2015", 12 pgs.
"U.S. Appl. No. 14/350,674, Response filed May 16, 2016 to Restriction Requirement dated Mar. 14, 2016", 10 pgs.
"U.S. Appl. No. 14/350,674, Restriction Requirement dated Mar. 14, 2016", 12 pgs.
"U.S. Appl. No. 14/369,741, Final Office Action dated Apr. 19, 2017", 10 pgs.
"U.S. Appl. No. 14/369,741, Non Final Office Action dated Aug. 22, 2016", 17 pgs.
"U.S. Appl. No. 14/369,741, Non Final Office Action dated Nov. 23, 2015", 11 pgs.
"U.S. Appl. No. 14/369,741, Preliminary Amendment filed Jun. 26, 2014", 16 pgs.
"U.S. Appl. No. 14/369,741, Response filed Mar. 23, 2016 to Non Final Office Action dated Nov. 23, 2015", 12 pgs.
"U.S. Appl. No. 14/369,741, Response filed Sep. 14, 2015 to Restriction Requirement dated May 14, 2015", 13 pgs.
"U.S. Appl. No. 14/369,741, Response filed Dec. 22, 2016 to Non-Final Office Action dated Aug. 22, 2016", 12 pgs.
"U.S. Appl. No. 14/369,741, Restriction Requirement dated May 14, 2015", 12 pgs.
"U.S. Appl. No. 14/627,739, Non Final Office Action dated Jan. 29, 2016", 4 pgs.
"U.S. Appl. No. 14/627,739, Notice of Allowance dated Jul. 6, 2016", 6 pgs.
"U.S. Appl. No. 14/627,739, Preliminary Amendment filed Feb. 20, 2015", 5 pgs.
"U.S. Appl. No. 14/627,739, Response filed Apr. 15, 2016 to Non Final Office Action dated Jan. 29, 2016", 6 pgs.
"U.S. Appl. No. 14/627,739, Response filed Nov. 5, 2015 to Restriction Requirement dated Aug. 6, 2015", 7 pgs.
"U.S. Appl. No. 14/627,739, Restriction Requirement dated Aug. 6, 2015", 5 pgs.
"U.S. Appl. No. 14/781,765, Advisory Action dated Jan. 29, 2019", 4 pgs.
"U.S. Appl. No. 14/781,765, Final Office Action dated Aug. 28, 2018", 9 pgs.
"U.S. Appl. No. 14/781,765, Non Final Office Action dated Feb. 15, 2018", 9 pgs.
"U.S. Appl. No. 14/781,765, Non Final Office Action dated Jul. 15, 2019", 7 pgs.
"U.S. Appl. No. 14/781,765, Response filed Jan. 21, 2019 to Final Office Action dated Aug. 28, 2018", 7 pgs.
"U.S. Appl. No. 14/781,765, Response filed Jun. 15, 2018 to Non Final Office Action dated Feb. 15, 2018", 6 pgs.

(56) References Cited

OTHER PUBLICATIONS

"U.S. Appl. No. 14/781,765, Response filed Jan. 24, 2018 to Restriction Requirement dated Aug. 24, 2017", 4 pgs.
"U.S. Appl. No. 14/781,765, Response filed Jan. 28, 2019 to Non-Final Office Action dated Aug. 28, 2018", 7 pgs.
"U.S. Appl. No. 14/781,765, Restriction Requirement dated Aug. 24, 2017", 6 pgs.
"U.S. Appl. No. 14/781,817, Preliminary Amendment filed Jan. 17, 2017", 5 pgs.
"U.S. Appl. No. 14/781,817, Restriction Requirement dated Oct. 31, 2018", 9 pgs.
"U.S. Appl. No. 14/781,817, Supplemental Preliminary Amendment field Aug. 8, 2017", 9 pgs.
"U.S. Appl. No. 14/781,817, Supplemental Preliminary Amendment filed Jun. 27, 2017", 9 pgs.
"U.S. Appl. No. 14/797,487, Non Final Office Action dated Jun. 14, 2017", 7 pgs.
"U.S. Appl. No. 14/797,487, Preliminary Amendment filed Jul. 24, 2015", 10 pgs.
"U.S. Appl. No. 14/797,487, Response filed Mar. 3, 2017 to Restriction Requirement dated Jan. 3, 2017", 10 pgs.
"U.S. Appl. No. 14/797,487, Restriction Requirement dated Jan. 3, 2017", 12 pgs.
"U.S. Appl. No. 14/970,998, Final Office Action dated Sep. 27, 2017", 13 pgs.
"U.S. Appl. No. 14/970,998, Non Final Office Action dated Apr. 6, 2017", 17 pgs.
"U.S. Appl. No. 14/970,998, Notice of Allowance dated Mar. 16, 2018", 9 pgs.
"U.S. Appl. No. 14/970,998, Preliminary Amendment filed Dec. 16, 2015", 3 pgs.
"U.S. Appl. No. 14/970,998, Preliminary Amendment filed Dec. 28, 2015", 13 pgs.
"U.S. Appl. No. 14/970,998, Response filed Feb. 27, 2018 to Final Office Action dated Sep. 27, 2017", 8 pgs.
"U.S. Appl. No. 14/970,998, Response filed Mar. 17, 2017 to Restriction Requirement dated Jan. 19, 2017", 8 pgs.
"U.S. Appl. No. 14/970,998, Response filed Aug. 7, 2017 to Non-Final Office Action dated Apr. 6, 2017", 13 pgs.
"U.S. Appl. No. 14/970,998, Restriction Requirement dated Jan. 19, 2017", 8 pgs.
"U.S. Appl. No. 15/023,093 Responsed filed Feb. 3, 2017 to Restriction Requirement dated Nov. 3, 2016", 12 pgs.
"U.S. Appl. No. 15/023,093, Non Final Office Action dated Apr. 11, 2017", 12 pgs.
"U.S. Appl. No. 15/023,093, Preliminary Amendment filed Mar. 18, 2016", 3 pgs.
"U.S. Appl. No. 15/023,093, Restriction Requirement dated Nov. 3, 2016", 10 pgs.
"U.S. Appl. No. 15/023,110, Corrected Notice of Allowance dated Sep. 5, 2017", 8 pgs.
"U.S. Appl. No. 15/023,110, Non Final Office Action dated Feb. 24, 2017", 10 pgs.
"U.S. Appl. No. 15/023,110, Notice of Allowance dated Aug. 21, 2017", 11 pgs.
"U.S. Appl. No. 15/023,110, Preliminary Amendment filed Mar. 18, 2016", 3 pgs.
"U.S. Appl. No. 15/023,110, Preliminary Amendment filed Jul. 5, 2016", 7 pgs.
"U.S. Appl. No. 15/023,110, Response filed Jul. 24, 2017 to Non-Final Office Action dated Feb. 24, 2017", 10 pgs.
"U.S. Appl. No. 15/380,962, Non Final Office Action dated Aug. 2, 2017", 20 pgs.
"U.S. Appl. No. 15/380,962, Preliminary Amendment filed Dec. 15, 2016", 3 pgs.
"U.S. Appl. No. 15/380,962, Response filed Jul. 19, 2017 to Restriction Requirement dated May 18, 2017", 9 pgs.
"U.S. Appl. No. 15/380,962, Restriction Requirement dated May 18, 2017", 9 pgs.
"U.S. Appl. No. 15/474,800, Final Office Action dated Mar. 8, 2019", 9 pgs.
"U.S. Appl. No. 15/474,800, Non Final Office Action dated Oct. 18, 2018", 8 pgs.
"U.S. Appl. No. 15/474,800, Preliminary Amendment filed Jul. 19, 2017", 12 pgs.
"U.S. Appl. No. 15/474,800, Preliminary Amendment filed Oct. 10, 2017", 4 pgs.
"U.S. Appl. No. 15/474,800, Response filed Jan. 18, 2019 t Non-Final Office Action dated Oct. 18, 2019", 11 pg.
"U.S. Appl. No. 15/474,800, Response filed Aug. 13, 2018 to Restriction Requirement dated Mar. 12, 2018", 11 pgs.
"U.S. Appl. No. 15/474,800, Restriction Requirement dated Mar. 12, 2018", 8 pgs.
"U.S. Appl. No. 15/474,810, Final Office Action dated Mar. 8, 2019", 10 pgs.
"U.S. Appl. No. 15/474,810, Non Final Office Action dated Sep. 20, 2018", 12 pgs.
"U.S. Appl. No. 15/474,810, Preliminary Amendment filed Jul. 18, 2017", 8 pgs.
"U.S. Appl. No. 15/474,810, Response filed Jan. 18, 2019 to Non-Final Office Action dated Sep. 20, 2018", 8 pgs.
"U.S. Appl. No. 15/474,810, Response filed Aug. 7, 2018 to Restriction Requirement dated Mar. 7, 2018", 8 pgs.
"U.S. Appl. No. 15/474,810, Restriction Requirement dated Mar. 7, 2018", 8 pgs.
"U.S. Appl. No. 15/474,810. Supplemental Preliminary Amendment filed Oct. 30, 2017", 4 pgs.
"U.S. Appl. No. 15/557,000, Preliminary Amendment filed Sep. 8, 2017", 7 pgs.
"U.S. Appl. No. 15/557,000, Restriction Requirement dated Mar. 11, 2019", 9 pgs.
"U.S. Appl. No. 15/557,368, Preliminary Amendment filed Sep. 11, 2017", 8 pgs.
"U.S. Appl. No. 15/557,368, Restriction Requirement dated Feb. 15, 2019", 8 pgs.
"U.S. Appl. No. 15/757,254, Preliminary Amendment filed Mar. 2, 2018", 11 pgs.
"U.S. Appl. No. 15/757,254, Restriction Requirement dated Sep. 16, 2019", 11 pgs.
"U.S. Appl. No. 15/757,269, Examiner Interview Summary dated Jun. 25, 2019", 5 pgs.
"U.S. Appl. No. 15/757,269, Final Office Action dated Oct. 25, 2019", 20 pgs.
"U.S. Appl. No. 15/757,269, Non Final Office Action dated Apr. 12, 2019", 30 pgs.
"U.S. Appl. No. 15/757,269, Non Final Office Action dated Dec. 4, 2018", 19 pgs.
"U.S. Appl. No. 15/757,269, Response filed Oct. 14, 2019 to Non-Final Office Action dated Apr. 12, 2019", 10 pgs.
"U.S. Appl. No. 15/757,269, Response filed Mar. 28, 2019 to Non-Final Office Action dated Dec. 4, 2018", 10 pgs.
"U.S. Appl. No. 16/025,557, Non Final Office Action dated Feb. 6, 2020", 8 pgs.
"U.S. Appl. No. 16/025,557, Preliminary Amendment filed Jul. 2, 2018", 10 pgs.
"U.S. Appl. No. 16/490,280, Advisory Action dated Sep. 21, 2021", 3 pgs.
"U.S. Appl. No. 16/490,280, Final Office Action dated May 13, 2021", 9 pgs.
"U.S. Appl. No. 16/490,280, Non Final Office Action dated Nov. 13, 2020", 8 pgs.
"U.S. Appl. No. 16/490,280, Preliminary Amendment filed Aug. 30, 2019", 7 pgs.
"U.S. Appl. No. 16/490,280, Response filed Apr. 13, 2021 to Non Final Office Action dated Nov. 13, 2020", 7 pgs.
"U.S. Appl. No. 16/490,280, Response filed Sep. 13, 2021 to Final Office Action dated May 13, 2021", 9 pgs.
"U.S. Appl. No. 16/490,280, Response filed Sep. 28, 2020 to Restriction Requirement dated Jul. 27, 2020", 7 pgs.
"U.S. Appl. No. 16/490,280, Restriction Requirement dated Jul. 27, 2020", 8 pgs.

(56) References Cited

OTHER PUBLICATIONS

"U.S. Appl. No. 16/500,349, Preliminary Amendment filed Oct. 2, 2019", 7 pgs.
"U.S. Appl. No. 16/635,246. Preliminary Amendment filed Jan. 30, 2020", 7 pgs.
"U.S. Appl. No. 16/828,137, Non Final Office Action dated Jun. 15, 2021", 29 pgs.
"U.S. Appl. No. 16/828,137, Preliminary Amendment filed Mar. 24, 2020", 6 pgs.
"U.S. Appl. No. 16/828,137, Response filed Jun. 2, 2021 to Restriction Requirement dated Apr. 2, 2021", 6 pgs.
"U.S. Appl. No. 17/264,452, Restriction Requirement dated Apr. 2, 2021", 13 pgs.
"U.S. Appl. No. 17/264,452, Preliminary Amendment filed Aug. 28, 2020", 7 pgs.
"U.S. Appl. No. 17/264,452, Preliminary Amendment Filed Jan. 29, 2021", 6 pgs.
"U.S. Appl. No. 17/277,256, Preliminary Amendment filed Mar. 17, 2021", 7 pgs.
"U.S. Appl. No. 17/277,260, Preliminary Amendment filed Mar. 17, 2021", 7 pgs.
"U.S. Appl. No. 17/434,363, Preliminary Amendment filed Aug. 26, 2021", 7 pgs.
"U.S. Appl. No. 14/781,765, Preliminary Amendment filed Jul. 20, 2016", 6 pgs.
"U.S. Appl. No. 15/858,923, Preliminary Amendment filed Jun. 23, 2016", 11 pgs.
"U.S. Appl. No. 15/858,923, Preliminary Amendment filed Dec. 29, 2017", 7 pgs.
"Australian Application Serial No. 2012249474, First Examiner Report dated Jul. 20, 2016", 4 pgs.
"Australian Application Serial No. 2012323937, First Examiner Report dated Oct. 7, 2016", 5 pgs.
"Chinese Application Serial No. 201280031496.8, Decision on Rejection dated Jun. 7, 2016", (English Translation), 9 pgs.
"Chinese Application Serial No. 201280061866.2, Office Action dated Mar. 17, 2016", with English translation of claims, 23 pgs.
"European Application Serial No. 12776480.1, Extended European Search Report dated Oct. 9, 2014", 8 pgs.
"European Application Serial No. 12776480.1, Response filed May 5, 2015 to Office Action dated Oct. 28, 2014", 10 pgs.
"European Application Serial No. 12840155.1, Communication Pursuant to Article 94(3) EPC dated Nov. 24, 2016", 5 pgs.
"European Application Serial No. 12840155.1, Extended European Search Report dated May 28, 2015", 6 pgs.
"European Application Serial No. 14778464.9, Amendment filed Oct. 28, 2015", 18 pgs.
"European Application Serial No. 14778464.9, Extended European Search Report dated Oct. 21, 2016", 8 pgs.
"European Application Serial No. 14778464.9, Response filed May 13, 2016 to Communication pursuant to Rules 161(2) and 162 EPC dated Nov. 20, 2015", 17 pgs.
"European Application Serial No. 14779421.8, Extended European Search Report dated Oct. 13, 2016", 11 pgs.
"European Application Serial No. 14779421.8, Response filed May 12, 2016 to Communication pursuant to Rules 161(2) and 162 EPC dated Nov. 13, 2015", 21 pgs.
"European Application Serial No. 14845415.0, Response filed Nov. 2, 2016 to Communication pursuant to Rules 161(1) and 162 EPC dated May 2, 2016", 9 pgs.
"European Application Serial No. 14846653.5, Extended European Search Report dated Apr. 26, 2017", 9 pgs.
"European Application Serial No. 14846653.5, Response filed Nov. 2, 2016 to Communication pursuant to Rules 161(1) and 162 EPC dated May 2, 2016", 37 pgs.
"International Application Serial No. PCT/US2014/056342, International Preliminary Report on Patentability dated Mar. 22, 2016", 9 pgs.
"International Application Serial No. PCT/US2010/020096, International Preliminary Report on Patentability dated Jul. 14, 2011", 5 pgs.
"International Application Serial No. PCT/US2010/020096, International Search Report dated Sep. 17, 2010", 3 pgs.
"International Application Serial No. PCT/US2010/020096, Written Opinion dated Sep. 17, 2010", 3 pgs.
"International Application Serial No. PCT/US2012/035529, International Preliminary Report on Patentability dated Nov. 7, 2013", 8 pgs.
"International Application Serial No. PCT/US2012/035529, International Search Report dated Oct. 23, 2012", 5 pgs.
"International Application Serial No. PCT/US2012/035529, Written Opinion dated Oct. 23, 2012", 8 pgs.
"International Application Serial No. PCT/US2012/060072, International Preliminary Report on Patentability mailed", 10 pgs.
"International Application Serial No. PCT/US2012/060072, International Search Report dated Mar. 28, 2013", 6 pgs.
"International Application Serial No. PCT/US2012/060072, Written Opinion dated Mar. 28, 2013", 9 pgs.
"International Application Serial No. PCT/US2012/072297, International Preliminary Report on Patentability dated Jul. 10, 2014", 13 pgs.
"International Application Serial No. PCT/US2012/072297, International Search Report dated Jun. 2, 2013", 6 pgs.
"International Application Serial No. PCT/US2012/072297, Written Opinion dated Jun. 2, 2013", 11 pgs.
"International Application Serial No. PCT/US2014/032702, International Preliminary Report on Patentability dated Oct. 6, 2015", 10 pgs.
"International Application Serial No. PCT/US2014/032702, International Search Report dated Aug. 26, 2014", 5 pgs.
"International Application Serial No. PCT/US2014/032702, Written Opinion dated Aug. 26, 2014", 9 pgs.
"International Application Serial No. PCT/US2014/032711, International Preliminary Report on Patentability Oct. 6, 2015", 10 pgs.
"International Application Serial No. PCT/US2014/032711, International Search Report dated Aug. 5, 2014", 5 pgs.
"International Application Serial No. PCT/US2014/032711, Written Opinion dated Aug. 5, 2014", 9 pgs.
"International Application Serial No. PCT/US2014/056312, International Preliminary Report on Patentability dated Mar. 31, 2016", 10 pgs.
"International Application Serial No. PCT/US2014/056312, International Search Report dated Dec. 24, 2014", 5 pgs.
"International Application Serial No. PCT/US2014/056312, Written Opinion dated Dec. 24, 2014", 8 pgs.
"International Application Serial No. PCT/US2014/056342, International Search Report dated Dec. 23, 2014", 4 pgs.
"International Application Serial No. PCT/US2014/056342, Written Opinion dated Dec. 23, 2014", 8 pgs.
"International Application Serial No. PCT/US2015/053244, International Preliminary Report on Patentability dated Apr. 13, 2017", 10 pgs.
"International Application Serial No. PCT/US2015/053244, International Search Report dated Feb. 4, 2016", 5 pgs.
"International Application Serial No. PCT/US2015/053244, Written Opinion dated Feb. 4, 2016", 8 pgs.
"International Application Serial No. PCT/US2016/021490, International Preliminary Report on Patentability dated Sep. 21, 2017", 7 pgs.
"International Application Serial No. PCT/US2016/021490, International Search Report dated Jun. 30, 2016", 4 pgs.
"International Application Serial No. PCT/US2016/021490, Written Opinion dated Jun. 30, 2016", 5 pgs.
"International Application Serial No. PCT/US2016/022056, International Preliminary Report on Patentability dated Sep. 21, 2017", 7 pgs.
"International Application Serial No. PCT/US2016/022056, International Search Report dated Jul. 7, 2016", 4 pgs.
"International Application Serial No. PCT/US2016/022056, Written Opinion dated Jul. 7, 2016", 5 pgs.

(56) References Cited

OTHER PUBLICATIONS

"International Application Serial No. PCT/US2016/050259, International Preliminary Report on Patentability dated Mar. 15, 2018", 10 pgs.
"International Application Serial No. PCT/US2016/050259, International Search Report dated Dec. 15, 2016", 4 pgs.
"International Application Serial No. PCT/US2016/050259, Written Opinion dated Dec. 15, 2016", 8 pgs.
"International Application Serial No. PCT/US2016/050260, International Preliminary Report on Patentability dated Mar. 15, 2018", 8 pgs.
"International Application Serial No. PCT/US2016/050260, International Search Report dated Dec. 22, 2016", 3 pgs.
"International Application Serial No. PCT/US2016/050260, Written Opinion dated Dec. 22, 2016", 6 pgs.
"International Application Serial No. PCT/US2018/020496, International Preliminary Report on Patentability dated Sep. 12, 2019", 6 pgs.
"International Application Serial No. PCT/US2018/020496, International Search Report dated Jun. 14, 2018", 4 pgs.
"International Application Serial No. PCT/US2018/020496, Written Opinion dated Jun. 14, 2018", 4 pgs.
"International Application Serial No. PCT/US2018/025830, International Preliminary Report on Patentability dated Oct. 17, 2019", 9 pgs.
"International Application Serial No. PCT/US2018/025830, International Search Report dated Aug. 2, 2018", 4 pgs.
"International Application Serial No. PCT/US2018/025830, Written Opinion dated Aug. 2, 2018", 7 pgs.
"International Application Serial No. PCT/US2018/045218, International Preliminary Report on Patentability dated Feb. 13, 2020", 7 pgs.
"International Application Serial No. PCT/US2018/045218, International Search Report dated Nov. 29, 2018", 3 pgs.
"International Application Serial No. PCT/US2018/045218, Written Opinion dated Nov. 29, 2018", 5 pgs.
"International Application Serial No. PCT/US2019/020084, International Preliminary Report on Patentability dated Sep. 10, 2020", 7 pgs.
"International Application Serial No. PCT/US2019/020084, International Search Report dated Jun. 6, 2019", 3 pgs.
"International Application Serial No. PCT/US2019/020084, Written Opinion dated Jun. 6, 2019", 5 pgs.
"International Application Serial No. PCT/US2019/044107, International Preliminary Report on Patentability dated Feb. 11, 2021", 6 pgs.
"International Application Serial No. PCT/US2019/044107, International Search Report dated Nov. 14, 2019", 2 pgs.
"International Application Serial No. PCT/US2019/044107, Written Opinion dated Nov. 14, 2019", 4 pgs.
"International Application Serial No. PCT/US2019/052658, International Preliminary Report on Patentability dated Apr. 1, 2021", 6 pgs.
"International Application Serial No. PCT/US2019/052658, International Search Report dated Mar. 12, 2020", 3 pgs.
"International Application Serial No. PCT/US2019/052658, Written Opinion dated Mar. 12, 2020", 4 pgs.
"International Application Serial No. PCT/US2019/052669, International Preliminary Report on Patentability dated Apr. 1, 2021", 7 pgs.
"International Application Serial No. PCT/US2019/052669, International Search Report dated Jan. 9, 2020", 3 pgs.
"International Application Serial No. PCT/US2019/052669, Written Opinion dated Jan. 9, 2020", 5 pgs.
"International Application Serial No. PCT/US2020/020066, International Preliminary Report on Patentability dated Sep. 10, 2021", 6 pgs.
"International Application Serial No. PCT/US2020/020066, International Search Report dated Jun. 25, 2020", 2 pgs.
"International Application Serial No. PCT/US2020/020066, Written Opinion dated Jun. 25, 2020", 4 pgs.
"Israel Application Serial No. 232025, Office Action dated May 1, 2016", 2 pgs.
"Japanese Application Serial No. 2014-508125, Office Action dated Feb. 15, 2016", with English translation of claims, 9 pgs.
"Japanese Application Serial No. 2014-508125, Written Amendment filed Apr. 27, 2015", with English translation, 29 pgs.
"Japanese Application Serial No. 2014-508125, Decision on Refusal dated Dec. 26, 2016", with English translation, 2 pgs.
"Japanese Application Serial No. 2014-535948, Office Action dated Jun. 27, 2016", with machine translation, 16 pgs.
"Mexican Application Serial No. MX/a/2014/004415, Office Action dated Apr. 19, 2018", with machine translation, 6 pgs.
"New Zealand Application Serial No. 624962, First Examiner Report dated Feb. 9, 2016", 3 pg.
"Russian Application Serial No. 2014119428, Office Action dated Apr. 15, 2016", 2 pgs.
"Russian Application Serial No. 2014119428, Office Action dated Apr. 21, 2017", with English Translation, 7 pgs.
"Singapore Application Serial No. 11201401499X, Office Action dated Apr. 19, 2016", 11 pgs.
"Singapore Application Serial No. 11201401499X, Written Opinion dated Oct. 5, 2015", 11 pgs.
Akazawa, Takashi, et al., "Development of a dendritic cell-targeting lipopeptide as an immunoadjuvant that inhibits tumor growth without inducing local inflammation", International Journal of Cancer, vol. 135, (2014), 2847-2856.
Ashley, et al., "(abstract) Development of a Virus-Like Particle that integrates Phage Display and Targeted delivery capabilities", MRS meeting, (2010), 1 pg.
Ashley, C E, et al., "Cell-Specific Delivery of Diverse Cargos by Bacteriophage MS2 Virus-like Particles", ACSNano, 5(7), (2011), 1-26.
Ashley, Ce, et al., "Delivery of Small Interfering RNA by Peptide-Targeted Mesoporous Silica Nanoparticle-Supported Lipid Bilayers", ACS Nano, vol. 6, No. 3, (2012), 2174-2188.
Attard, George S, et al., "Liquid-crystalline phases as templates for the synthesis of mesoporous silica", Nature Publishing Group vol. 378, (Nov. 23, 1995), 3 pgs.
Aubin, R. A., et al., "Highly effective delivery of foreign DNA to adherent cells via polybrene/DMSO-assisted gene transfer", Methods Mol Biol., 62, (1997), 319-42.
Bao, et al., "Targeted Gene Therapy of Ovarian Cancer using an Ovarian-Specific Promoter", Gynecologic Oncology, 84, (2002), 228-34.
Beckett, D, et al., "Roles of Operator and Non-operator RNA Sequences in Bacteriophage R17 Capsid Assembly", J Moi Biol, 204, (1988), 939-947.
Benneti, GJ, et al., "A peripheral mononeuropathy in rat that produces disorders of pain sensation like those seen in man", Pain, (1988), 87-107.
Bennett, Gary, et al., "A peripheral mononeuropathy in rat that produces disorders of pain sensation like those seen in man.", Pain, 33, (1988), 87-107.
Beteck, Richard, "Chemical and biochemical modification of mesoporous silicon for in vivo analysis.", Master's thesis, University of Eastern Finland,, (2013), 8-9.
Brinker, C Jeffrey, et al., "Evaporation-Induced Self-Assembly: Nanostructures Made Easy", Advanced Materials, 11(7), (May 1999), 579-585.
Buranda, T, et al., "Biomimetic Molecular Assemblies on Glass and Mesoporous Silica Microbeads for Biotechnology", Langmuir, 19, (2003), 1654-1663.
Butler, Kimberly, et al., "Protocells: Modular Mesoporous Silica Nanoparticle-Supported Lipid Bilayers for Drug Delivery", Small 12, No. 16, (2016), 2173-2185.
Caldeira, J C, et al., "Stability and assembly in vitro of bacteriophage PP7 virus-like particles", Journal of Nanobiotechnology, 5, (2007), 1-13.
Carnes, E C, et al., "Confinement-induced quorum sensing of individual *Staphylococcus aureus* bacteria", Nature Chemical Biology, 6, (2010), 1-12.

(56) References Cited

OTHER PUBLICATIONS

Carnes, Eric C., et al., "Targeted Nanoporaus Particle-Supported Lipid Bllayen for Treatment of Childhood Leukemia", (Jun. 2011), 1 pg.
Carroll, N J, et al., "Microparticles with Bimodal Nanoporosity Derived by Microemulsion Templating", Langmuir 25(23), (2009), 13540-13544.
Cartier, et al., "Utilization of synthetic peptides containing nuclear localization signals for nonviral gene transfer systems", Gene Therapy, 9, (2002), 157-67.
Chackerian, B, et al., "Peptide Epitope Identification by Affinity Selection on Bacteriophage MS2 Virus-Like Particles", J Mol Biol; 409, (2011), 1-18.
Chacur, M, et al., "A new model of sciatic inflammatory neuritis (SIN): induction of unilateral and bilateral mechanical allodynia following acute unilateral peri-sciatic immune activation in rats", Pain, 94, (2001), 231-244.
Chedid, Georgeset, et al., "Recent Trends in Covalent and Metal Organic Frameworks for Biomedical Applications", Nanomaterials (Basel), 8(11)., (Nov. 7, 2018), 27 pgs.
Cheng, Wwk, et al., "Expression and purification of two anti-CD19 single chain Fv fragments for targeting of liposomes to CD19-expressing cells", Biochimica et Biophysics Acta, 1768, (2007), 21-29.
Citorik, R J, et al., "Sequence-specific antimicrobials using efficiently delivered RNA-guided nucleases", Nature biotechnology, (Sep. 21, 2014), 13 pgs.
Clemens, Daniel L., et al., "Targeted Intracellular Delivery of Antituberculosis Drugs to *Mycobacterium tuberculosis*-infected Macrophages via Functionalized Mesoporous Silica Nanoparticles", Antimicrobial Agents and Chemotherapy, (Feb. 2012), 2535-2545.
Cokol, M, et al., "Finding nuclear localization signals", EMBO Reports, 1(5), (2000), 1-17.
Crombez, Laurence, et al., "Targeting cyclin B1 through peptide-based delivery of siRNA prevents tumour growth", Nucleic Acids Res., vol. 37, No. 14, (2009), 4559-4569.
Dengler, Ellen C, et al., "Improvement of spinal non-viral IL-10 gene delivery by D-mannose as a transgene adjuvant to control chronic neuropathic pain", Journal of Neuroinflammation, (2014), 1-21.
Dengler, Ellen C., et al., "Mesoporous silica-supported lipid bilayers (protocells) for DAN cargo delivery to the spinal cord", Journal of Controlled Release 168, (2013), 209-224.
Dubertret, B, et al., "In Vivo Imaging of Quantum Dots Encapsulated in Phospholipid Micelles", Science, vol. 298, (Nov. 29, 2002), 1759-1762.
Epler, et al., "Nanopourous-Supported Lipid Bilayer Nanocarriers for Treatment of Childhood Leukemia", Materials Research Society, Symposium LL: Biometic Engineering of Micro-and Nanoparticles; LL6.11, (2011), 32 pgs.
Epler, K, et al., "Delivery of Ricin Toxin A-Chain by Peptide-Targeted mesoporous Silica Nanoparticle Supported Lipid Bilayers.", Advanced Healthcare Materials, (2012), 348-353.
Fan, H, et al., "Rapid prototyping of patterned functional nanostructures", Nature, 405(6782), (May 4, 2000), 56-60.
Fang, Aiping, et al., "Template-Free Formation of Monodisperse Doughnut-Shaped Silica Microparitcles by Droplet-Based Microfluidics", Chem. Mater, (2011), 4660-4662 pgs.
Feng, Pingyun, et al., "Control of Pore Sizes in Mesoporous Silica Templated by Liquid Crystals in Block Copolymer-Cosurfactant-Water Systems", Langmuir, vol. 16, No. 12,, (Mar. 24, 2000), 7 pgs.
Fishkis, M, et al., "Abstracts: 'Self organization of short peptides and simple amphiphiles into membranes' and 'Encapsulation of polynucleotide/polypeptide systems by membranes', from Steps Towards the Formation of a Protocell: The Possible Role of Short Peptides", Orig Life Evol Biosph, vol. 37, (2007), 543-545.
Fishkis, Maya, "Steps Towards the Formation of a Protocell: The Possible Role of Short Peptides", Orig Live Evol Biosph 37, (2007), 537-553.

Gamal, M M, et al., "Skin delivery of oestradiol from lipid vesicles: importance of liposome structure", Int. J. Pharm., vol. 204, No. 1-2, (2000), 159-169.
Gariepy, et al., "Vectorial Delivery of Macromolecules Into Cells Using Peptide-Based Vehicles", Trends in Biotechnology vol. 19, (2001), 21-28.
Giacomo, Dacarro, et al., "Monolayers of Polyethilenimine on Flat Glass: A Versatile Platform for Cations Coordination and Nanoparticle Grafting in the Preparation of Antibacterial Surfaces", Dalton Trans. 41, 2456, (Jan. 5, 2012), 8 pgs.
Gordon, Alan N., et al., "Recurrent Epithelial Ovarian Carcinoma: A Randomized Phase III Study of Pegylated Liposomal Doxorubicin Versus Topotecan", Journal of Clinical Oncology, 19(14), (2001), 3312-3322.
Hatakeyama, "A pH-sensitive fusogenic peptide facilitates endosomal escape and greatly enhances the gene silencing of siRNA-containing nanoparticles in vitro and in vivo", Journal of Controlled Release, 139(2), (Oct. 15, 2009), 127-132.
Hicks, Randall W, et al., "Nanoparticle Assembly of Mesoporous A100H (Boehmite)", Chemistry of Materials, vol. 15, No. 1, (Jan. 1, 2003), 78-82.
Hildebrand, et al., "Nanoscale control of silica morphology and three-dimensional structure during diatom cell wall formation", Mater. Res. vol. 21, No. 10, (2006), 2689-2698.
Hooker, J M, et al., "Interior Surface Modification of Bacteriophage MS2", J Am Chem Soc, 126, (2004), 3718-3719.
Huo, Qisheng, et al., "Surfactant Control of Phases in the Synthesis of Mesoporous Silica-Based Materials", Chem. Mater. 1996, 8, (Feb. 15, 1996), 14 pgs.
Iskandar, Ferry, et al., "Control of the morphology of nanostructured particles prepared by the spray drying of nanopartilce sol", Journal of Colloid and Interface Science 265, (2003), 296-303.
Israelachvili, J N, et al., "Physical principles of membrane organization", Quarterly Reviews of Biophysics, vol. 13(2),, (1980), 121-200.
Jain, P T, et al., "Enhancement of liposomal gene delivery in human breast cancer cells by dimethyl sulfoxide", (Mar. 1998), 609-611.
Jain, R. K, "Barriers to drug delivery in Solid Tumors", Scientific American,.271 (1), (Jul. 1994), 58-65.
Jewett, M C, et al., "Mimicking the *Escherichia coli* Cytoplasmic Environment Activates Long-Lived and Efficient Cell-Free Protein Synthesis", Wiley InterScience, [Online] Retrieved from the internet: <www.interscience.wiley.com DOI: 10.1002/bit.20026>, (2004), 19-26.
Jillavenkatesa, A, "Particle Size Characterization", National Institute of Standards and Technology, Special Publication 960-1, (2001), 1-167.
Jinping, Lai, et al., "Versatile Fluorescence Resonance Energy Transfer-Based Mesoporous Silica Nanoparticles for Real-Time Monitoring of Drug Release", ACS Nano, vol. 7, No. 3, (2013), 2741-2750.
Kaczanowska, Sabina, et al., "TLR agonists: our best frenemy in cancer immunotherapy", Journal of leukocyte Biology, 93(6), (2013), 847-863.
Kennedy, E M, et al., "Inactivation of the Human Papilloma virus E6 or E7 Gene in Cervical Carcinoma Cells by Using a Bacterial CRISPR/Cas RNA-Guided Endonuclease", Journal of Virology, (Aug. 6, 2014), 12 pgs.
Kim, D M, "A highly efficient cell-free protein synthesis system from *Excherichia coli*", Eur J Biochem, 239, (1996), 881-886.
Kim, E, et al., "Iodine 125-labeled mesenchymal-epithelial transition factor binding peptide-click-cRGDyk heterodimer for glioma imaging", Cancer Science, vol. 102, No. 8, (2011), 1516-1521.
Konermann, S, et al., "Genome-scale transcriptional activation by an engineered CRISPR-Cas9 complex", Nature, 2015, vol. 517, 583-588.
Kunkel, T. A., "Rapid and Efficient Site-Specific Mutagenesis without Phenotypic Selection", Proc. Natl. Acad. Sci. USA, 82, (1985), 488-492.
Lacasse, E C, et al., "Nuclear localization signals overlap DNA- or RNA-binding domains in nucleic acid-binding proteins", Nucleic Acids Research, 23(10), (1995), 1647-1656.

(56) References Cited

OTHER PUBLICATIONS

Li, Z., et al., "Mesoporous Silica Nanoparticles in Biomedical Applications", Chemical Society Reviews 41, (2012), 2590-2605.
Lim, F, et al., "RNA recognition site of PP7 coat protein", Nucleic Acids Research, 30(19), (2002), 4138-4144.
Liu, J, et al., "Electrostatically Mediated Liposome Fusion and Lipid Exchange with a Nanoparticle-Supported Bilayer for Control of Surface Charge, Drug Containment, and Delivery.", J Am Chem Soc, 131, (2009), 7567-7569.
Liu, Juewen, et al., "Silica nanoparticle supported lipid bilayers for gene delivery.", Chem Commun, (2009), 5100-5102.
Liu, Xiangsheng, et al., "Irinotecan Delivery by Lipid-Coated Mesoporous Silica Nanoparticles Shows Improved Efficacy and Safety over Liposomes for Pancreatic Cancer", ACS Nano 10, (2016), 2702-2715.
Lo, et al., "Hepatocellular Carcinoma Cell-Specific Peptide Ligand for Targeted Drug Delivery", Molecular Cancer Therapeutics 7(3), (2008), 579-589.
Lu, Weigang, et al., "Tuning the structure and function of metal-organic frameworks via linker design", Chemical Society Reviews, 43, (2014), 5561-5593.
Lu, Y, et al., "Aerosol-assisted self-assembly of mesostructured spherical nanoparticles", Nature, 398, (1999), 223-226.
Lu, Yunfeng, et al., "Continuous formation of supported cubic and hexagonal mesoporous films by sol-gel-dip-coating", Nature, 389(6649), (Sep. 25, 1997), 364-368.
Lu, Yunfeng, et al., "Evaporation-Induced Self-Assembly of Hybrid Bridged Silsesquioxane Film and Particulat Mesophases With Integral Organic Functionalitiy", Journal of the American Chemical Society, 122(22), (Jun. 1, 2000), 5258-5261.
Maghraby, El, et al., "Interactions of surfactants (edge activators) and skin penetration enhancers with liposomes", Int. J. Pharm., vol. 276, No. 1-2, (2004), 143-161.
Mamaeva, Veronika, et al., "Mesoporous silica nanoparticles in medicine—Recent adva", Advanced Drug Delivery Reviews, Elsevier, Amsterdam, NL, vol. 65, No. 5, (Aug. 18, 2012), 689-702.
Mao, A, et al., "Deterministic encapsulation of single cells in thin tunable microgels for niche modeling and therapeutic delivery", Nat Mater 16, pp. 236-243, (2017), 21 pgs.
Matteo, Porotto, et al., "Synthetic protocells interact with viral nanomachinery and inactivate pathogenic human virus", PLOS One, val. 6, No. 3, (Mar. 1, 2011), 16874 pgs.
McDonald, Michael, "Functioning Nanostructures Self-Assemble Out of Ink", Posted May 8, 2000, http://www.amtexpo.com/nano/messages/255.html, (May 8, 2000), 3 pgs.
Meng, Huan, et al., "Co-delivery of an Optimal Drug/siRNA Combination Using Mesoporous Silica Nanoparticle to Overcome Drug Resistance in Breast Cancer In Vitro and In Vivo", ACS Nano., (2013), 1-21.
Meng, Huan, et al., "Two-Wave Nanotherapy to Target the Stroma and Optimize Gemcitabine Delivery to a Human Pancreatic Cancer Model in Mice", ACS Nano vol. 7 No. 11, (2013), 10048-10065.
Meng, Huan, et al., "Use of a Lipid-Coated Mesoporous Silica Nanoparticle Platform for Synergistic Gemcitabine and Paclitaxel Delivery to Human Pancreatic Cancer in Mice", ACS Nano, vol. 9, No. 4, (2015), 3540-3557.
Meng, Huan, et al., "Use of Size and a Co-polymer Design Feature to Improve the Biodistribution and the Enhanced Permeability and Retention Effect of Doxorubicin-loaded Mesoporous Silica Nanoparticles in a Murine Xenograft Tumor Model", ACS Nano, (2011), 32 pgs.
Midoux, P, et al., "Membrane Permeabilization and Efficient Gene Transfer by a Peptide Containing Several Histidines", Bioconjugate Chem, 9, (1998), 260-267.
Milligan, Ed, et al., "Pathological and protective roles of glia in chronic pain.", Nature Reviews Neuroscience, 10, (2009), 23-36.
Milligan, Ed, et al., "Thermal hyperalgesia and mechanical allodynia produced by intrathecal administration of the human immunodeficiency virus-1 (HIV-1) envelope glycoprotein, gp 120.", Brain Research, 861, (2000), 105-116.

Milligan, Erin, et al., "Intrathecal polymer-based interleukin-10 gene delivery for neuropathic pain", Neuron Glia Biology 2, (2007), 1-16.
Mohamed, Salma, et al., "(Abstract) Polymeric nano-micelles: versatile platform for targeted delivery in cancer", Ther. Deliv., vol. 5, No. 10, pp. 1101-1121, (Oct. 2014), 1 pg.
Moller, K, et al., "Highly efficient siRNA delivery from core-shell mesoporous silica nanoparticles with multifunctional polymer caps", Nanoscale, 8, (2016), 13 pgs.
Mollick, Samraj, et al., "(Abstract) Outer Surface Hydrophobic Shielding Strategy to Enhance the Chemical Stability of Metal-Organic Polyhedra", Angew Chem Int Ed Engl, vol. 58, No. 4, pp. 1041-1045, (Jan. 21, 2019), 1 pg.
Mornet, et al., "The Formation of Support Lipid Bilayers on Silica Nanoparticles Revealed by Cryoelectron Microscopy", NanoLetters 5(2), (2005), 281-285.
Mungall, Bruce, et al., "Inhibition of Henipavirus infection by RNA interference", Antiviral Res., vol. 80, No. 3, (2008), 324-331.
Nakamura, Takashi, et al., "Nanoparticulation of BCG-CWS for application to bladder cancer therapy", Journal of Controlled Release vol. 176, (2014), 44-53.
Nikolic, M, et al., "Synthesis and characterization of mesoporous silica core-shell particles", Processing and Application of Ceramics, 4(2), (2010), 81-85.
Park, J, et al., "Cell-in-Shell Hybrids: Chemical Nanoencapsulation of Individual Cells", Acc. Chem. Res., 49(5), (2016), 792-800.
Pastan, I, et al., "Immunotoxin therapy of cancer.", Nature Reviews 6, (2006), 559-565.
Peabody, D S, "A Viral Platform for Chemical Modification and Multivalent Display", Journal of Nanobiotechnology, 1, (2003), 1-8.
Peabody, D S, et al., "Immunogenic Display of Diverse Peptides on Virus-like Particles of RNA Phage MS2", J Mol Biol, 380, (2008), 1-18.
Peabody, D S, "Translational Repression by Bacteriophage MS2 Coat Protein Expressed from a Plasmid", The Journal of Biological Chemistry; 265(10), (1990), 5684-5689.
Pickett, G G, et al., "Encapsidation of heterologous RNAs by bacteriophage MS2 coat protein", Nucleic Acids Research, 21(19), (1993), 4621-4626.
PN, Durfee, et al., "Mesoporous Silica Nanoparticle-Supported Lipid Bilayers (Protocells) for Active Targeting and Delivery to Individual Leukemia Cells", ACS Nano, vol. 10, (2016), 8325-8345.
Porotto, M, et al., "Synthetic Protocells Interact with Viral Nano machinery and Inactivate Pathogenic Human Virus", (2011), 1-9 pgs.
Prokop, Ales, "Intracellular Delivery Fundamentals and Applications", ISBN Springer, (2011), 1-867.
Rao, G.V. R, et al., "Monodisperse Mesoporous Silica Microspheres Formed by Evaporation-Induced Self Assembly of Surfactant Templates in Aerosols", Adv. Mater, 14, No. 18, (Sep. 16, 2002), 1301-1304.
Raskopf, et al., "siRNA Targeting Vegf Inhibits Hepatocellular Carcinoma Growth and Tumor Angiogenesis In Vivo", Journal of Heptaology 49, (2008), 977-984.
Ricco, R, et al., "Metal-Organic Frameworks for Cell and Virus Biology: A Perspective", ACS Nano, 12, (Jan. 8, 2018), 13-23.
Rocca, F D, et al., "Cell Composition of the Human Pulmonary Valve: A Comparative Study with the Aortic Valve—The VESALIO* Project", Ann Thorac Surg. 70, (2000), 1594-1600.
Rodriguez, et al., "Minimal Self Peptides That Inhibit Phagocytic Clearance and Enhance Delivery of Nano particles", (2013), 971-975 pgs.
Rodriguez, F, et al., "DNA Immunization: Ubiquitination of a Viral Protein Enhances Cytotoxic T-Lymphocyte Induction and Antiviral Protection but Abrogates Antibody Induction", Journal of Virology, vol. 7 No. 11, (Nov. 1997), 8497-8503.
Rosenholm, Jessica M, et al.,, "Towards multifunctional, targeted drug delivery systems using mesoporous silica nanoparticles—opportunities", Nanoscale, vol. 2, No. 10, (Jan. 1, 2010), 1870-1883.
Ryther, RCC, et al., "siRNA therapeutics: big potential from small RNAs", Gene Therapy, vol. 12, (2005), 5-11.

(56) References Cited

OTHER PUBLICATIONS

Sanjana, N E, et al., "Improved vectors and genome-wide libraries for CRISPR screening", Nat Methods, (2014), 783-784.
Sapra P, Allen TM, et al., "Internalizing Antibodies are Necessary for Improved Therapeutic Efficacy of Antibody-targeted Liposomal Drugs.", Cancer Res 62, (2002), 7190-7194.
Schiller, Renate, et al., "Synthesis of Mesoporous Silica Particles and Capsules by Miniemulsion Technique", Chem. Mater. 2009, 21, (Sep. 23, 2009), 11 pgs.
Seo, Seog-Jin, et al., "Gene delivery techniques for adult stem cell-based regenerative therapy", Nanomedicine, vol. 8, No. 11,, (2013), 2 pgs.
Shiraishi, T., et al., "Photochemically enhanced cellular delivery of cell penetrating peptide-PNA conjugates.", FEBS Letters, 580(5), (2006), 1451-1456.
Shou-Cang, Shen, et al., "Mesoporous silica nanoparticle-functionalized poly(methylmethacrylate)-based bone cement for effective antibiotics delivery", Journal of Materials Science: Materials in Medicine, Kluwer Academic Publishers, BO,vol. 22, No. 10, (Jul. 24, 2011), 2283-2292.
Sloane, E, et al., "Chronic constriction injury induced pathological pain states are controlled long term via intrathecal administration of a non-viral vector (NW) encoding the anti-inflammatory cy1okine interleukin-10 (IL-10).", Second Joint Scientific Meeting of the American Pain Society and the Canadian Pain Society. Churchill Livingstone., (2004), p. 15.
Sloane, E, et al., "Immunological priming potentiates non-viral anti-inflammatory gene therapy treatment of neuropathic pain.", Gene Therapy, 16, (2009), 1210-1222.
Slowing, I I, et al., "(Abstract) Mesoporous silica nanoparticles as Controlled release drug delivery and gene transfection carriers", Advanced Drug Delivery Reviews vol. 60, Issue 11, (2008), 1278-1288.
Smothers, J F, et al., "Affinity Selection from Biological Libraries", Science, 298, (2002), 621-622.
Soderquist, et al., "Microparticle-mediated delivery of interleukin-1 0 plasmid DNA for the treatment of neuropathic pain", Poster Abstract No. 206d, (May 2008), 2 pgs.
Soderquist, R., et al., "Release of Plasmid DNA-Encoding IL-10 from PLGA Microparticles Facilitates Long-Term Reversal of Neuropathic Pain Following a Single Intrathecal Administration.", Pharmaceutical Research, (2010), 841-854.
Sorensen, Malin, "Mesostructured particulate silica materials with tunable pore size", Doctoral Thesis at the Royal Institute of Technology. Stockholm, Sweden,, (2009), 19-21.
Stemmer, WPC, et al., "Single-step assembly of a gene and entire plasmid from large numbers of oligodeoxyribonucleotides", Gene,164, (1995), 49-53.
Suteewong, T, et al., "(Abstract) Synthesis and formation mechanism of aminated mesoporous silica nanoparticles", Chemistry of Materials, 24, (2012), 1 pg.
Suteewong, T, et al., "Highly aminated mesoporous silica nanoparticles with cubic pore structure", Journal of the American Chemical Society, 133(2), (2011), 172-175.
Takeuchi, S, "An Axisymmetric Flow-Focusing Microfluidic Device", Adv Mater, 17:8, (2005), 1067-1072.
Tarn, D, et al., "Mesoporous Silica Nanoparticle Nanocarriers: Biofunctionality and Biocompatibility.", Accounts of Chemical Research, (2013), 792-801.
Tatusova, T A, et al., "BLAST 2 Sequences, a new tool for comparing protein and nucleotide sequences", FEMS Microbiology Letters, 174, (1999), 247-250.
Tawfik, D S, et al., "Man-made cell-like compartments for molecular evolution", Nature Biotechnology; 16, (1998), 652-656.
Tianyi, Wang, et al., "Enhanced mucosal and systemic immune responses obtained by porous silica nanoparticles used as an oral vaccine adjuvant: Effect of silica architecture on immunological properties", International Journal of Pharmaceutics, vol. 436, No. 1-2, (Oct. 1, 2012), 351-358.

Torchilin, VP, et al., "Recent Advances with Liposomes as Pharmaceutical Carriers.", Nature Reviews, vol. 4, (2005), 145-159.
Townson, Jason L, et al., "Re-examining the Size/Charge Paradigm: Differing in Vivo Characteristics of Size- and Charge-Matched Mesoporous Silica Nanoparticles", J Am Chem Soc 135(43), (Oct. 30, 2013), 4 pgs.
Uhlenbeck, O C, "A coat for all sequences", Nature structural biology, 5(3), (1998), 174-176.
Videira, et al., "Lymphatic uptake of lipid nanoparticles following endotracheal administration", Journal of Microencapsulation: Micro and Nano Carriers, 23(8), (2006), 855-862.
Villegas, et al., "Hybrid Collagenase Nanocapsules for Enhanced Nanocarrier Penetration in Tumoral Tissues", ACS Appl. Mater. Interfaces vol. 7, (2015), 24075-24081.
Vingerhoeds, et al., "Immunoliposome-mediated targeting of doxorubicin to human ovarian carcinoma in vitro and in vivo", British Journal of Cancer, (1996), 1023-29.
Wang, L-S, et al., "Biofunctionalized Phospholipid-Capped Mesoporous Silica Nanoshuttles for Targeted Drug Delivery: Improved Water Suspensibility and Decreased", ACS Nano, vol. 4 No. 8, (2010), 4371-4379.
Wang, Qingmin, et al., "improved Cellular Immune Response Elicited by a Ubiquitin-Fused DNA Vaccine Against *Mycobacterium tuberculosis*", DNA and Cell Biology, vol. 31, No. 4, (2012), 489-495.
Wani, Amit, et al., "Surface Functionalization of Mesoporous Silica Nanoparticles Controls Loading and Release Behavior of Mitoxantrane", Pharmaceutical Research, Kluwer Academic Publishers—Plenum Publishers, NL, vol. 29, No. 9, (May 4, 2012), 2407-2418.
Weis, K, "Importins and exportins: how to get in and out of the nucleus", TIBS, 23, (1998), 185-189.
Wu, M, et al., "Cell-specific Delivery of Bacteriophage-Encapsidated Ricin A Chain", Bioconjugate Chem, 6, (1992), 587-595.
Xia, Tian, et al., "Polyethyleneimine Coating Enhances the Cellular Uptake of Mesoporous Silica Nanoparticles and Allows Safe Delivery of siRNA and DNA Constructs", ACS Nano; 3(10), (Oct. 27, 2009), 25 pgs.
Yazdi, I, et al., "Novel mesoporous silicon particles as an efficient sustained delivery system for antibiotics", NSTI—Nanotech 2010, [Online] Retrieved from the Internet: <https://www.researchgate.net/profile/Iman Yazdi/publication/290613308 Novel mesaporous silicon particles as an efficient sustained delivery system-for antibiotics/links>, (Jan. 1, 2010), 324-325.
Youn, W, et al., "(Abstract) Cytoprotective Encapsulation of Individual Jurkat T Cells within Durable TiO2 Shells for T-Cell Therapy", Angew. Chem, Int. Ed., 56(36), pp. 10702-10706, (2017), 1 pg.
Yu-Shen, Lin, et al., "Well-Ordered Mesoporous Silica Nanoparticles as Cell Markers", Chem. Mater, 17, (2005), 4570-4573.
Zapryanova, et al., "Toroidal Microporous Silica Gel", Journal of Materials Science 14, (1979), 1175-1178 pgs.
Zelphati, et al., "Mechanism of Oligonucleotide Release from Cationic Liposomes", Proceedings of the National Academy of Sciences USA 93, (1996), 11493-98.
Zhang, Haiyuan, et al., "Differential Expression of Syndecan-1 Mediates Cationic Nanoparticle Toxicity in Undifferentiated versus Differentiated Normal Human Bronchial Epithelial Cells", ACS Nano, (2011), 1-29.
Zhang, Jing, et al., "Multifunctional Envelope-Type Mesoporous Silica Nanoparticles for Tumor-Triggered Targeting Drug Delivery", J. Am. Chem. Soc, 135 (13), (2013), 5068-5073.
Zhang, K, et al., "Facile Large-Scale Synthesis of Monodisperse Mesoporous Silica Nanospheres with Tunable Pore Structure", Journal of the American Chemical Society, (2013), 2427-2430.
Zhu, Kelong, et al., "Metal-Organic Frameworks with Mechanically Interlocked Pillars: Controlling Ring Dynamics in the Solid-State via a Reversible Phase Change", J Am Chem Soc. 136(20), (May 21, 2014), 7403-7409.
Zhu, Wei, et al., "Modular Metal-Organic Polyhedra Superassambly: From Molecular-Level Design to Targeted Drug Delivery", Adv. Mater., vol. 31, No. 12, 1806774, (Mar. 2019), 10 pgs.

(56) References Cited

OTHER PUBLICATIONS

U.S. Appl. No. 09/838,153 U.S. Pat. No. 6,471,761, filed Apr. 20, 2001, Rapid Prototyping of Patterned Organic/Inorganic Functional Nanostructures.
U.S. Appl. No. 10/163,425 U.S. Pat. No. 6,913,832, filed Jun. 7, 2002, Prototyping of Patterned Functional Nanostructures.
U.S. Appl. No. 09/543,572, filed Apr. 5, 2000, Photo-Definable Self-Assembled Materials.
U.S. Appl. No. 10/100,108 U.S. Pat. No. 6,808,867, filed Mar. 19, 2002, Photo-Definable Self-Assembled Materials.
U.S. Appl. No. 10/373,565 U.S. Pat. No. 7,332,264, filed Feb. 26, 2003, Photo-Definable Self-Assembled Materials.
U.S. Appl. No. 09/389,085, filed Sep. 2, 1999, Low Frequency Feedback Speaker System.
U.S. Appl. No. 08/385,338, filed Feb. 8, 1995, Unidirectional Ring Laser Gyroscope.
U.S. Appl. No. 08/250,882 U.S. Pat. No. 5,438,585, filed May 31, 1994, Unstable Resonator Semiconductor Laser.
U.S. Appl. No. 16/500,349, filed Oct. 2, 2019, Porous Nanoparticle-Supported Lipid Bilayer Delivery of Transcriptional Gene Modulators.
U.S. Appl. No. 15/023,093, filed Mar. 18, 2016, Core and Surface Modification of Mesoporous Silica Nanoparticles to Achieve Cell Specific Targeting In Vivo.
U.S. Appl. No. 15/023,110 U.S. Pat. No. 9,855,217, filed Mar. 18, 2016, Toroidal Mesoporous Silica Nanoparticles (TMSNPS) and Related Protocells.
U.S. Appl. No. 15/858,923, filed Dec. 29, 2017, Toroidal Mesoporous Silica Nanoparticles (TMSNPS) and Related Protocells.
U.S. Appl. No. 14/350,674, filed May 20, 2014, Porous Nanoparticle-Supported Lipid Bilayers (Protocells) for Targeted Delivery Including Transdermal Delivery of Cargo and Methods Thereof.
U.S. Appl. No. 15/380,962, filed Dec. 15, 2016, Porous Nanoparticle-Supported Lipid Bilayers (Protocells) for Delivery Including Transdermal Delivery of Cargo and Methods Thereof.
U.S. Appl. No. 14/781,765, filed Nov. 23, 2015, Mesoporous Alum Nanoparticles as a Universal Platform for Antigen Adsorption, Presentation, and Delivery.
U.S. Appl. No. 12/909,572 U.S. Pat. No. 8,992,984, filed Oct. 21, 2010, Protocells and Their Use for Targeted Delivery of Multicomponent Cargos to Cancer Cells.
U.S. Appl. No. 14/627,739 U.S. Pat. No. 9,480,653, filed Feb. 20, 2015, Protocells and Their Use for Targeted Delivery of Multicomponent Cargos to Cancer Cells.
U.S. Appl. No. 14/797,487, filed Jul. 13, 2015, Protocells and Their Use for Targeted Delivery of Multicomponent Cargos to Cancer Cells.
U.S. Appl. No. 14/113,371 U.S. Pat. No. 9,579,283, filed Dec. 4, 2013, Porous Nanoparticle-Supported Lipid Bilayers (Protocells) for Targeted Delivery and Methods of Using Same.
U.S. Appl. No. 14/970,998 U.S. Pat. No. 10,022,327, filed Dec. 16, 2015, Porous Nanoparticle-Supported Lipid Bilayers (Protocells) for Targeted Delivery and Methods of Using Same.
U.S. Appl. No. 16/025,557, filed Jul. 2, 2018, Porous Nanoparticle-Supported Lipid Bilayers (Protocells) for Targeted Delivery and Methods of Using Same.
U.S. Appl. No. 14/781,817, filed Nov. 9, 2015, Antibiotic Protocells and Related Pharmaceutical Formulations and Methods of Treatment.
U.S. Appl. No. 15/474,800, filed Mar. 30, 2017, Protocells for Plasmid and RNP Delivery in the Treatment of Cancer and Other Disease States.
U.S. Appl. No. 14/474,810, filed Mar. 30, 2017, Carriers for Plasmid and RNP Delivery in the Treatment of Cancer and Other Disease States.
U.S. Appl. No. 14/369,741, filed Jun. 30, 2014, CRLF-2 Binding Peptides, Protocells and Viral-Like Particles Useful in the Treatment of Cancer, Including Acute Lymphoblastic Leukemia (ALL).
U.S. Appl. No. 15/788,634, filed Oct. 19, 2017, CRLF-2 Binding Peptides, Protocells and Viral-Like Particles Useful in the Treatment of Cancer, Including Acute Lymphoblastic Leukemia (ALL).
U.S. Appl. No. 13/143,164 U.S. Pat. No. 8,734,816, filed Jul. 1, 2011, Porous Nanoparticle Supported Lipid Bilayer Nanostructures.
U.S. Appl. No. 14/253,030, filed Apr. 15, 2014, Porous Nanoparticle Supported Lipid Bilayer Nanostructures.
U.S. Appl. No. 15/557,368, filed Sep. 11, 2017, Generation of Mesoporous Materials Using Multiphase Surfactant Systems.
U.S. Appl. No. 12/903,577, filed Oct. 13, 2010, Protocells and Their Use for Pain Treatment.
U.S. Appl. No. 15/757,254, filed Mar. 2, 2018, Protocells to Treat Microbial Infection and for Synergistic Delivery.
U.S. Appl. No. 15/757,269, filed Mar. 2, 2018, Mesoporous Silica Nanoparticles and Supported Lipid Bi-Layer Nanoparticles for Biomedical Applications.
U.S. Appl. No. 16/828,137, filed Mar. 24, 2020, Mesoporous Silica Nanoparticles and Supported Lipid Bi-Layer Nanoparticles for Biomedical Applications.
U.S. Appl. No. 15/557,000, filed Sep. 8, 2017, CD 47 Containing Porous Nanoparticle Supported Lipid Bilayers (Protocells) Field of the Invention.
U.S. Appl. No. 16/490,280, filed Aug. 30, 2019, Active Targeting of Cells by Monosized Protocells.
U.S. Appl. No. 16/635,246, filed Jan. 30, 2020, Liposomal Coated Nanoparticles for Immunotherapy Applications.
U.S. Appl. No. 15/887,619, filed Feb. 2, 2018, Porous Nanoparticle-Supported Lipid Bilayers (Protocells) for Delivery Including Transdermal Delivery of Cargo and Methods Thereof.
U.S. Appl. No. 16/976,651, filed Aug. 28, 2020, Starry Mesoporous Silica Nanoparticles and Supported Lipid Bi-Layer Nanoparticles.
U.S. Appl. No. 17/264,452, filed Jan. 29, 2021, Biomimetic Rebuilding of Multifunctional Red Blood Cells.
U.S. Appl. No. 17/277,256, filed Mar. 17, 2021, Living Mammalian Cells Modified With Functional Modular Nanoparticles.
U.S. Appl. No. 17/277,260, filed Mar. 17, 2021, Armored Cells.
U.S. Appl. No. 17/434,363, filed Aug. 26, 2021, Modular Metal-Organic Polyhedra Superassembly Compositions.
"U.S. Appl. No. 16/490,280, Notice of Allowability dated Feb. 9, 2022", 3 pgs.
"U.S. Appl. No. 16/490,280, Notice of Allowance dated Jan. 28, 2022", 9 pgs.
"U.S. Appl. No. 16/635,246, Response filed Mar. 9, 2022 to Restriction Requirement dated Feb. 17, 2022", 7 pgs.
"U.S. Appl. No. 16/635,246, Restriction Requirement dated Feb. 17, 2022", 11 pgs.
"U.S. Appl. No. 16/976,651, Response filed Apr. 11, 2022 to Restriction Requirement dated Mar. 9, 2022", 6 pgs.
"U.S. Appl. No. 16/976,651, Restriction Requirement dated Mar. 9, 2022", 8 pgs.
Chantal, Pichon, et al., "Mannosylated and Histidylated LPR Technology for Vaccination with Tumor Antigen mRNA", <https://link.springer.com/content/pdf/10.1007%2F978-1-62703-260-5_16.pdf>, (2013), 247-274.
Harvey, R C, et al., "Rearrangement of CRLF2 is associated with mutation of JAK kinases, alteration of IKZF1, Hispanic/Latino ethnicity, and a poor outcome in pediatric, B-progenitor acute lymphoblastic leukemia", Blood, 115(26), (2010), 5312-5321.
Ikari, Kenichi, et al., "Structural Control of Mesoporous Silica Nanoparticles in a Binary Surfactant System", Langmuir 22(2), (2006), 5 pgs.
Martin, Kreutz, et al., "Targeting dendritic cells—why bother?", Blood, vol. 121, No. 15, (Apr. 11, 2013), 2836-2844.
Nekhotiaeva, Natalia, et al., "Inhibition of *Staphylococcus aureus* gene expression and growth using antisense peptide nucleic acids", Molecular Therapy, vol. 10, No. 4, (2004), 652-659.
"U.S. Appl. No. 16/500,349, Restriction Requirement dated Jun. 22, 2022", 9 pgs.
"U.S. Appl. No. 16/635,246, Non Final Office Action dated May 31, 2022", 19 pgs.
"U.S. Appl. No. 16/976,651, Non Final Office Action dated Jul. 19, 2022", 34 pgs.

(56) References Cited

OTHER PUBLICATIONS

Guo, Jimin, et al., "Cancer vaccines from cryogenically silicified tumour cells functionalized with pathogen-associated molecular patterns", Nature Biomedical Engineering vol. 6, (Jan. 2022), 19-31.
James, J Kobie, et al., "Transforming Growth Factor B Inhibits the Antigen-Presenting Functions and Antitumor Activity of Dendritic Cell Vaccines", Cancer Research, vol. 63, (Apr. 15, 2003), 1860-1864.
Kun, Zhang, et al., "Facile Large-Scale Synthesis of Monodisperse Mesoporous Silica Nanospheres with Tunable Pore Structure (Supporting Information)", Journal of the American Chemical Society, vol. 135, (2013), 16 pgs.
Lin, Xiong, et al., "Tunable stellate mesoporous silica nanoparticles for intracellular drug delivery", Journal of Materials Chemistry B, vol. 3, (2015), 1712-1721.
Socorro, Espuelas, et al., "Influence of Ligand Valency on the Targeting of Immature Human Dendritic Cells by Mannosylated Liposomes", Bioconjugate Chemistry, vol. 19, (2008), 2385-2393.
Yao, Sun, et al., "Stimuli-Responsive Shapeshifting Mesoporous Silica Nanoparticles", Nano Letters, vol. 16, (2016), 651-655.
Yao, Sun, et al., "Stimuli-Responsive Shapeshifting Mesoporous Silica Nanoparticles (Supporting Information)", Nano Letters, vol. 1, of supporting information, (2016), 1-11.
"U.S. Appl. No. 16/500,349, Response filed Aug. 22, 2022 to Restriction Requirement dated Jun. 22, 2022", 8 pgs.
"U.S. Appl. No. 16/635,246, Response filed Aug. 31, 2022 to Non Final Office Action dated May 31, 2022", 8 pgs.
"U.S. Appl. No. 16/635,246, Final Office Action dated Sep. 19, 2022", 19 pgs.
Berge, Stephen M, "Pharmaceutical Salts", Journal of Pharmaceutical Sciences, 66(1), (Jan. 1977), 1-19.
"U.S. Appl. No. 16/500,349, Non Final Office Action dated Nov. 30, 2022", 13 pgs.
"U.S. Appl. No. 16/976,651, Non Final Office Action dated Nov. 2, 2022", 37 pgs.
"U.S. Appl. No. 16/976,651, Response filed Oct. 19, 2022 to Non Final Office Action dated Jul. 19, 2022", 10 pgs.
Doshi, Nishit, et al., "Red blood cell-mimicking synthetic biomaterial particles", PNAS, vol. 106, No. 51, (Dec. 22, 2009), 21495-21499.
Langley, P J, "Nanoporous and mesoporaus organic structures: new openings for materials research", Chemical Society Reviews, vol. 28, (1999), 279-291.
Maeder, Morgan L, et al., "CRISPR RNA-guided activation of endogenous human genes", Nature Methods, (2013), 977-979.
Merkel, Timothy J., et al., "Using mechanobiological mimicry of red blood cells to extend circulation times of hydrogel microparticles", PNAS, vol. 108, No. 2, (Jan. 11, 2011), 586-591.
Qi, Lei S., et al., "Repurposing CRISPR as RNA-Guided Platform for Sequence-Specitic Control of Gene Expression", Cell, 1-22.
Wan, Chao, et al., "Activation of the hypoxia-inducible factor-1a pathway accelerates bone regeneration", PNAS, (2008), 686-691.
Wang, Zhen, et al., "Targeting p53 for Novel Anticancer Therapy", Translational Oncology, (2010), 1-12.
"U.S. Appl. No. 16/635,246, Response filed Jan. 19, 2023 to Final Office Action dated Sep. 19, 2022", 7 pgs.
"U.S. Appl. No. 16/635,246, Advisory Action dated Jan. 27, 2023", 5 pgs.
"U.S. Appl. No. 16/976,651, Examiner Interview Summary dated Jan. 27, 2023", 4 pgs.
"U.S. Appl. No. 16/976,651, Response filed Feb. 1, 2023 to Non Final Office Action dated Nov. 2, 2022", 13 pgs.
Taylor, Erik N., "Monitoring Therapeutic Responses to Silicified Cancer Cell Immunotherapy Using PET MRI in a Mouse Model of Disseminated Ovarian Cancer", Int. J. Mol. Sci. 2022, 23(18), 10525, (Sep. 10, 2022), 14 pgs.

\* cited by examiner

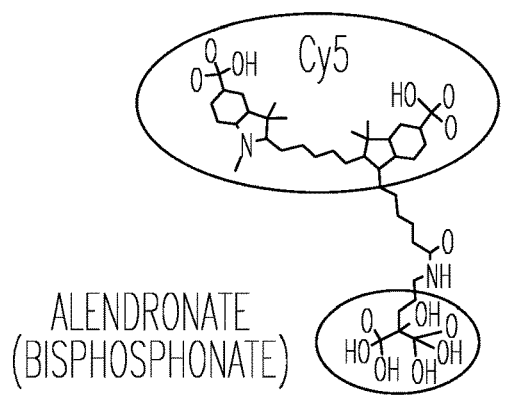 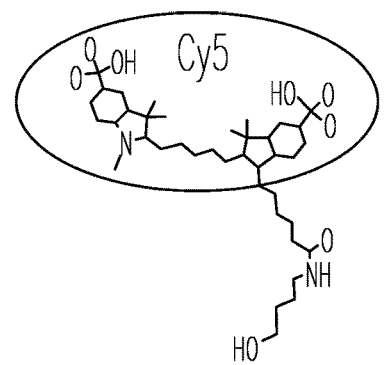
Fig. 3A    Fig. 3B
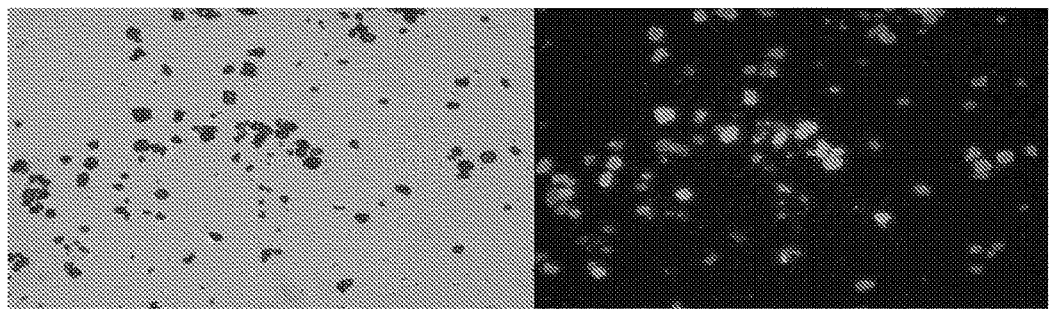
MSNP P2-A (ALENDRONATE CONJUGATED)
Fig. 4A
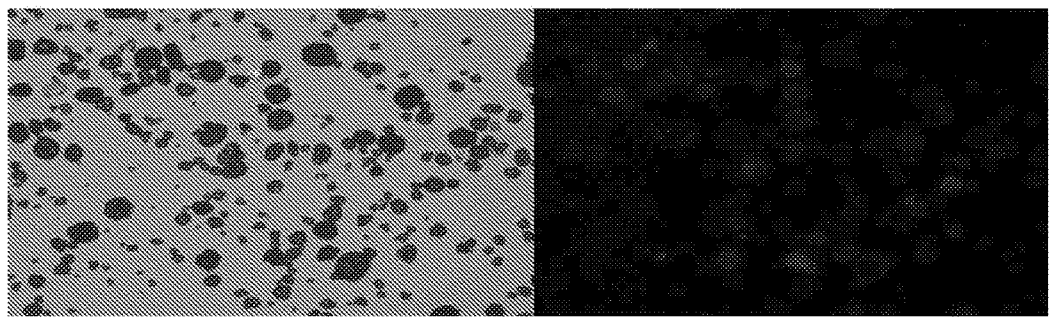
MSNP P2-COOH (BARE CARBOXYLIC ACID, NEGATIVE CONTROL)
Fig. 4B COOH-modified MSNP Bisphosphonate-modified MSNP COOH-modified MSNP Bisphosphonate-modified aSNP

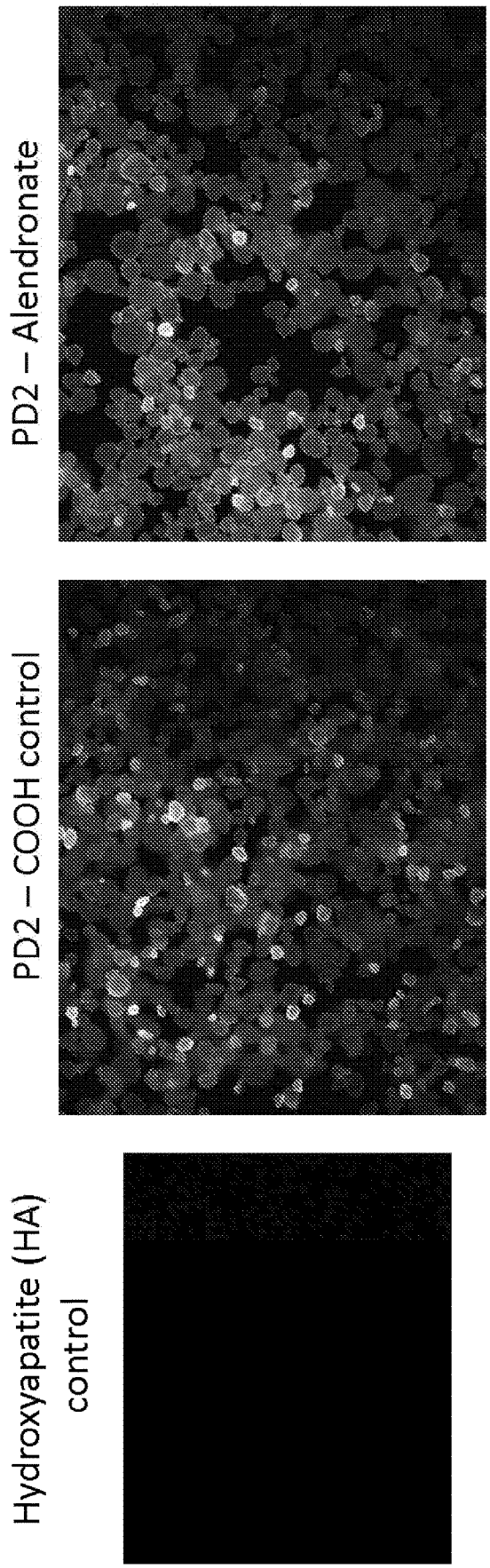

- Steric barrier
  - PEG
  - Zwitterionic coating
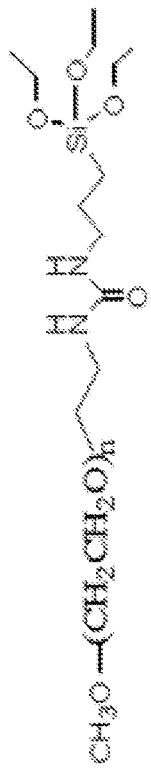
PEG silane MW 550 – 5000 g/mol
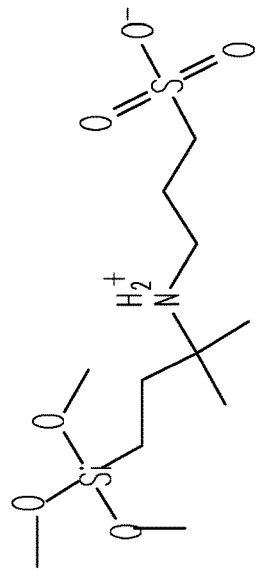
3-{[DIMETHYL(3-TRIMETHOXYSILYL)PROPYL]AMMONIO}PROPANE-1-SULFONATE
MW = 329.485 g/mol
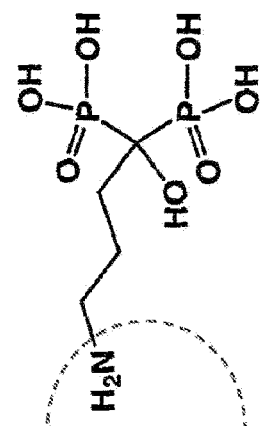
Combined MW = 507.42 g/mol
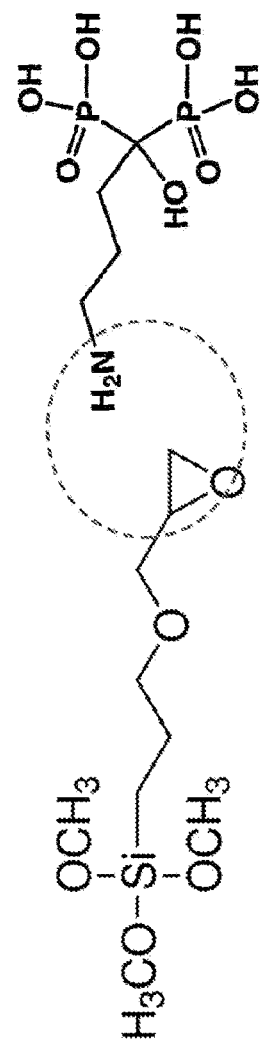
Alendronate
(3-Glycidyloxypropyl)trimethoxysilane
Fig. 19

PD42 – DBCO modified

PD47 Tibia

PD47 Liver

PD47 Heart

SEQUENCE LISTING

<160> NUMBER OF SEQ ID NOS: 9

<210> SEQ ID NO 1
<211> LENGTH: 8
<212> TYPE: PRT
<213> ORGANISM: Artificial Sequence
<220> FEATURE:
<223> OTHER INFORMATION: A synthetic amino acid sequence -continued

```
<400> SEQUENCE: 1

Arg Arg Arg Arg Arg Arg Arg
1               5

<210> SEQ ID NO 2
<211> LENGTH: 25
<212> TYPE: PRT
<213> ORGANISM: Artificial Sequence
<220> FEATURE:
<223> OTHER INFORMATION: A synthetic amino acid sequence

<400> SEQUENCE: 2

Gly Leu Phe His Ala Ile Ala His Phe Ile His Gly Gly Trp His Gly
1               5                   10                  15

Leu Ile His Gly Trp Tyr Gly Gly Cys
            20                  25

<210> SEQ ID NO 3
<211> LENGTH: 30
<212> TYPE: PRT
<213> ORGANISM: Artificial Sequence
<220> FEATURE:
<223> OTHER INFORMATION: A synthetic amino acid sequence

<400> SEQUENCE: 3

Trp Glu Ala Arg Leu Ala Arg Ala Leu Ala Arg Ala Leu Ala Arg His
1               5                   10                  15

Leu Ala Arg Ala Leu Ala Arg Ala Leu Arg Ala Gly Glu Ala
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: A synthetic amino acid sequence

<400> SEQUENCE: 4

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Gly Glu Ala
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: A synthetic amino acid sequence

<400> SEQUENCE: 5

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 6
<211> LENGTH: 23
<212> TYPE: PRT
<213> ORGANISM: Artificial Sequence
<220> FEATURE:
<223> OTHER INFORMATION: A synthetic amino acid sequence
```

```
<400> SEQUENCE: 6

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 7
<211> LENGTH: 26
<212> TYPE: PRT
<213> ORGANISM: Artificial Sequence
<220> FEATURE:
<223> OTHER INFORMATION: A synthetic amino acid sequence

<400> SEQUENCE: 7

Gly Leu Phe His Ala Ile Ala His Phe Ile His Gly Gly Trp His Gly
1               5                   10                  15

Leu Ile His Gly Trp Tyr Gly Gly Gly Cys
            20                  25

<210> SEQ ID NO 8
<211> LENGTH: 22
<212> TYPE: PRT
<213> ORGANISM: Artificial Sequence
<220> FEATURE:
<223> OTHER INFORMATION: A synthetic amino acid sequence

<400> SEQUENCE: 8

Gly Leu Phe His Ala Ile Ala His Phe Ile His Gly Gly Trp His Gly
1               5                   10                  15

Leu Ile His Gly Trp Tyr
            20

<210> SEQ ID NO 9
<211> LENGTH: 10
<212> TYPE: PRT
<213> ORGANISM: Artificial Sequence
<220> FEATURE:
<223> OTHER INFORMATION: A synthetic sequence
<221> NAME/KEY: SITE
<222> LOCATION: 6
<223> OTHER INFORMATION: Ser is D-Ser(But)
<221> NAME/KEY: SITE
<222> LOCATION: 10
<223> OTHER INFORMATION: Gly is Azgly

<400> SEQUENCE: 9

Gly His Trp Ser Tyr Ser Leu Arg Pro Gly
1               5                   10
```

OSTEOTROPIC NANOPARTICLES FOR PREVENTION OR TREATMENT OF BONE METASTASES

CROSS-REFERENCE TO RELATED APPLICATIONS

This application is a U.S. National Stage Filing under 35 U.S.C. 371 from International Application No. PCT/US2017/012583, filed on 6 Jan. 2017, and published as WO 2017/120504 on 13 Jul. 2017, which application claims the benefit of the filing date of U.S. application Ser. No. 62/276,388, filed on Jan. 8, 2016, U.S. application Ser. No. 62/276,297, filed Jan. 8, 2016, and U.S. application Ser. No. 62/395,196, tiled on Sep. 15, 2016, the disclosures of which are incorporated by reference herein.

BACKGROUND

Prostate cancer (PCa) is the most common non-cutaneous malignancy in men (1 in 14 ages 60-69) and with about 23,600 newly diagnosed cases and 4,000 deaths estimated in Canada during 2014. These deaths are primarily due to the emergence of prostate cancer bone metastases present in the axial skeleton, vertebral column, and major shaft bones years later (Chun et al., 2006; Han et al., 2001; Bianco et al., 2005; Kupelian et al., 1997; Pound et al., 1999). Metastatic prostate cancer is unique because of its predilection to the bone marrow, as determined by Tc-99m radiographic imaging; the knowledge of which is very important for the clinical management of these patients. The abundance of bone metastases in these patients, also known as skeletal related events (SRE), often lead to bone fractures and bone pain significantly decreasing quality of life (Suva et al., 2011). In recent years, exciting therapeutic drug options have been developed for use in patients with metastatic prostate cancer (Docetaxel, Cabazitaxel, Abiraterone, Enzalutamide) but these new agents have only generated modest survival and quality of life benefits (Heidenreich et al., 2014). Hence, optimization of existing therapeutic approaches remains necessary and a constant challenge for clinicians. The side effects associated with these drugs are clinically significant, considering that Docetaxel is intravenously administered at 70-115 mg/m$^2$ over 1-2 hours, for three cycles. Aside from these pharmacological offerings, radiopharmaceuticals such as Radium-223 chloride have emerged as significant therapeutic options which target the bone directly (Parker et al., 2013). Radium-223 exhibits a high affinity for hydroxyapatite, the mineralized component of bone, due to its chemical similarity to calcium (Parker et al., 2013). Benefits include an advantage in all major end-points such as an overall survival benefit (Parker et al., 2013) and is now approved for use in metastatic prostate cancer patients and is anticipated to become standard of care (Shirley and McCormack, 2014). Unfortunately, this radiopharmaceutical is not available to many patients due to a worldwide shortage of radiopharmaceuticals, as well as difficulty in providing the infrastructure for provision of this medication, and its high cost.

SUMMARY

The present disclosure provides for osteotropic (bone-specific) nanoparticle drug delivery system that when administered, preferentially accumulate in bone. After targeting to bone, nanoparticles elute an anticancer cargo, e.g., a multi-platform therapeutic payload (small molecules and/or siRNA) into the tumor microenvironment thus maximizing the anti-cancer effect and minimize exposure to normal tissues outside of bone. By concentrating drug within the bony structures, where the vast majority of prostate cancer metastases are found, greater therapeutic effect is achieved. These osteotropic nanoparticles are composed of mesoporous silica that can contain various payload types within the pores and where the surface of the nanoparticle and/or the protocell is decorated (generally, through chemical conjugation) with therapeutic agents, such as bisphosphonates. Bisphosphonates are widely used to inhibit bone loss/formation and covalently bind to hydroxyapatite (Russell et al., 2007), the mineralized calcium-based component of bone, and therefore bone targeting using bisphosphonate-decorated nanoparticles is a logical goal. After nanoparticle homing to bone, the payload is released in a slow and controlled manner into the surrounding bone marrow microenvironment. The ability of these nanoparticles to be incorporated into newly formed bone is highly convenient given the osteoblastic nature of metastatic prostate cancer. In this "bone-first" targeting strategy, drug/biologics/siRNA payloads are specifically incorporated into sites of bone formation induced by bone metastases (prostate cancer, breast cancer, lung cancer, ovarian cancer, among others) while levels in the general hematogenous circulation can be minimized.

Mesoporous silica nanoparticles (MSNPs) that contain drug/biologics/imaging agents are generally made of silicon dioxide and in various forms have FDA-approval. By themselves MSNPs exhibit negligible toxicities in the human body. See the FDA website fda.gov/food/ingredients packaging labeling/gras/scogs/ucm261095.htm. The lack of toxicity of MSNPs is based on the fact that each of the silica bonds are able to hydrolyze in vivo, releasing drug into surrounding areas while the solubilized silica is readily passed by the kidney and excreted via urine. Biophysically, MNSPs range in size considerably, but in one embodiment diameters include 50-80 run (in certain embodiments, about 150 to about 200 nm in diameter), which exhibit a half-life of 5-7 days, continuously releasing drug/cargo into the immediate microenvironment (Lin et al., 2015). The implications of this bone-specific drug delivery system are potentially significant because present FDA-approved drugs for treatment of CRPC can be specifically delivered in these nanoparticles, at a much lower dose and cost and minimum side-effects because of the targeting feature of the nanoparticles. Payloads that will be used for incorporation with the nanoparticles include chemotherapy (Docetaxel) and siRNA specific for Androgen Receptor (AR(I6)), an important target for metastatic prostate cancer. As siRNA technology continues to be a promising and specific means of targeting and sensitizing tumor cells to other treatments (e.g., AR(16)), this osteotropic drug delivery system could maximize the effectiveness of siRNA therapeutics designed to target CRPC while minimizing the loss of siRNA in the hematogenous circulation due to the short serum half-life of siRNA. Experiments in this project are designed to fully elucidate the relationship between target and non-target exposure as a consequence of bone targeting technology.

BRIEF DESCRIPTION OF THE FIGURES

FIGS. 3A-B. Chemical structures of Alendronate-Cy5 and NOTdronate-Cy5. A) Cy5 is conjugated to Alendronate which is a bisphosphonate. B) Cy5 is conjugated to a molecule lacking the bisphosphonate.

FIGS. 4A-B. A) Brightfield (left) and fluorescent (right) images of Alendronate MSNPs. B) Brightfield (left) and fluorescent (right) images of carboxylic acid MSNPs, (right) images of NOTdronate-FITC stained hydroxyapatite particles.

FIGS. 18A-C. Hydroxyapatite (HA) binding of modified MSNPs. A) HA control. B) PD2 Control. C) PD2-Alendronate. Hydroxyapatite is a naturally occurring mineral form of calcium apatite $[Ca_{10}(PO_4)_6(OH)_2]$ with a positive charge. COOH modified MSNPs have about a −50 mV zeta potential, and DBCO-modified MSNPs have about a −30 mV zeta potential.

FIG. 19. Exemplary reagents to decrease non-specific binding.

DETAILED DESCRIPTION

Figure 1A:
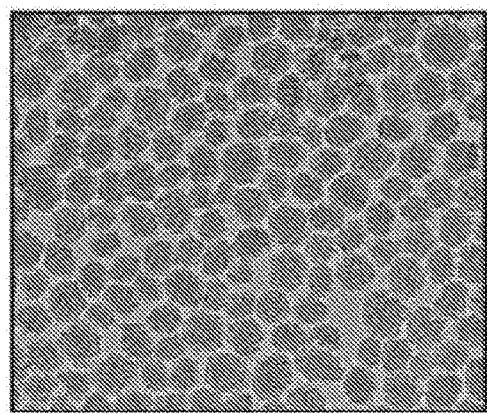
FIGS. 1A-C. Ultrastructure of various mesoporous silica nanoparticles (MSNPs) and their ability to hold different types of cargo. Transmission electron microscopy (TEM) of MSNPs with normal pores (A). TEM of MSNPs loaded with magnetite core (contrast agent) shown in B. TEM of MSNPs with large pores (C). Scale bar is 50 nm.
Figure 1B:
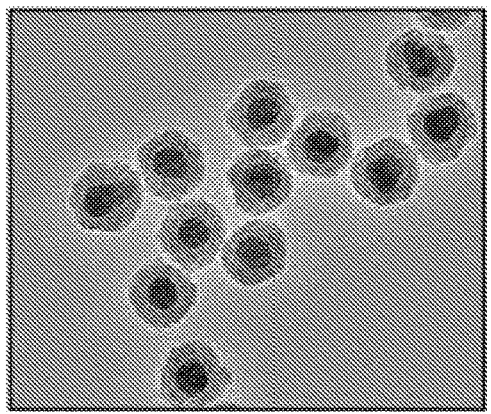
Figure 1C:
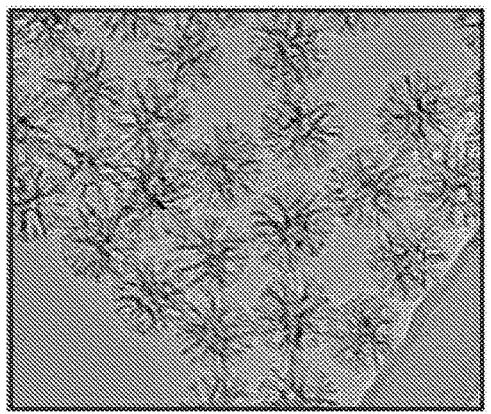

Embodiments are directed to particles and protocells for specific targeting of cells, in particular aspects, cancer bone cells, especially metastatic cancer bone cells. The protocells are useful in diagnostic, therapeutic and therapeutic monitoring applications.

In one embodiment, the present disclosure is directed to a bone cell-targeting porous particles and protocells comprising a mesoporous silica nanoparticle optionally with a supported lipid bilayer coating said nanoparticle, at least one bisphosphonate moiety conjugated to the surface of the the lipid bilayer and at least one cargo selected from the group consisting of at least one anticancer small molecule, at least one RNA molecule selected from the group consisting of small interfering RNA (siRNA), small hairpin RNA (shRNA), microRNA or a mixture thereof, e.g., a siRNA with anticancer activity, a peptide including an anticancer peptide and a reporter (e.g., diagnostic agent such as an imaging agent, which imaging agent may also function as a therapeutic agent); and optionally, at least one cell penetrating peptide (e.g., a fusogenic peptide that promotes endosomal escape of particles and protocells and encapsulated DNA, if present), a cell targeting peptide and other cargo comprising at least one cargo component selected from the group consisting of a DNA molecule (e.g., naked DNA, a double stranded linear DNA or a plasmid DNA which optionally produces an anticancer peptide) wherein said DNA molecule is optionally conjugated further with a nuclear localization sequence.

In certain embodiments, particles, e.g., MSNPs, or MSNP supported lipid bilayers (protocells) having a nanoporous silica core with a supported lipid bilayer either or both of which is conjugated to a bisphosphonate moiety for targeting the protocell to bone cancer cells; a cargo comprising at least one therapeutic agent which optionally facilitates cancer cell death such as a traditional small molecule, a macromolecular cargo (e.g. siRNA such as S565, S7824 and/or S 10234, among others, shRNA, a radionuclide complexed with a chelating moiety such as DOTA, among others, a protein toxin such as a ricin toxin A-chain or diphtheria toxin A-chain) and/or a packaged plasmid DNA (in certain embodiments—histone packaged) disposed within the nanoporous silica core (e.g., supercoiled as otherwise described herein in order to more efficiently package the DNA into protocells as a cargo element) which is optionally modified with a nuclear localization sequence to assist in localizing/presenting the plasmid within the nucleus of the cancer cell and the ability to express peptides involved in therapy (e.g., apoptosis/cell death of the cancer cell) or as a reporter (fluorescent green protein, fluorescent red protein, a fluorescent dye, a radionuclide among others, as otherwise described herein) for diagnostic applications, including monitoring therapy of the cancer treated, where applicable. Protocells may further include a targeting peptide which targets cells for therapy (e.g., cancer cells in tissue to be treated) such that binding of the protocell to the targeted cells is specific and further enhanced and a fusogenic peptide that promotes endosomal escape of protocells and encapsulated DNA. Protocells may be used in therapy, in diagnostics and/or monitoring therapy, more specifically to treat bone cancer, especially metastatic bone cancer. In other aspects, protocells use binding peptides which selectively bind to cancer tissue (especially bone cancer, including especially metastatic bone cancer) for therapy and/or diagnosis of cancer, including the monitoring of cancer treatment and drug discovery.

In one aspect, a porous nanoparticle may comprise a nanoporous silica core optionally with a supported lipid bilayer. In this aspect, the particle or protocell comprises a targeting peptide which is or contains a cancer binding moiety, often in combination with a cell penetrating peptide such as a fusogenic peptide on the surface of the particle or protocell. The particle or protocell may be loaded with various therapeutic and/or diagnostic cargo, including for example, small molecules (therapeutic anticancer and/or diagnostic, macromolecules including polypeptides and nucleotides, including RNA (shRNA and especially siRNA) or plasmid DNA which may be supercoiled and histone-packaged including a nuclear localization sequence, which may be therapeutic and/or diagnostic which may include a small molecule fluorescent day, or other reporter molecule (including a reporter molecule such as a fluorescent peptide, including fluorescent green protein/FGP, fluorescent red protein/FRP, among others), or a chelating compound such as DOT A or a related radionuclide chelator in combination with a radionuclide which may be used for diagnostic and/or therapeutic purposes.

Pharmaceutical compositions comprise a population of particles, e.g., MSNPs, or protocells as otherwise described herein in combination with a carrier, additive and/or excipient. These pharmaceutical compositions may be used in diagnostic and/or therapeutic applications, including applications related to the monitoring of therapy, especially cancer therapy.

Methods for treating bone cancer, especially including metastatic bone cancer, or reducing the likelihood that a cancer will metastasize to bone cancer in a patient in need, comprise administering a therapeutically effective number of bone-targeted particles or protocells comprising at least one anticancer agent or an effective amount of a pharmaceutical composition comprising the bone-targeted particles or protocells which comprise at least one anticancer agent, often multiple cancer anticancer agents.

Methods for diagnosing bone cancer, especially including metastatic bone cancer (for example, secondary to a primary cancer such as prostate cancer, breast cancer, lung cancer and ovarian cancer, among numerous others, comprise administering an effective amount of a population of particles or protocells as described herein which bind to bone cancer cells and include at least one reporter or other diagnostic agent in the particle or protocell to a patient suspected of having cancer or known to have primary cancer, determining the number or amount of said particles or protocells or a diagnostic agent contained in said particles or protocells which bind to or are incorporated into bone tissue of said patient and comparing the number or amount of said particles or protocells or said diagnostic agent which bind to or are incorporated into said bone tissue in said patient to a standard (which standard may include a standard obtained from one or more healthy patients, including the patient being diagnosed, a standard obtained from one or more patients with bone cancer, including metastatic bone cancer) and comparing the binding of the particles or protocells and/or diagnostic agent in the patent with the standard wherein a level above or below the standard is indicative of the presence or absence of bone cancer, including metastatic cancer.

The present disclosure is also directed to a method of monitoring therapy of cancer, including metastatic bone cancer in a patient in need, the method comprising administering to a patient at least twice at different times during therapy for said cancer a diagnostic effective amount of a population of particles or protocells which bind to bone tissue and which contain a reporter (e.g., a diagnostic agent), determining the number or amount of said particles or protocells or said reporter which binds to or is incorporated into bone tissue in said patient at said times and comparing the binding/incorporation of said particles or protocells or said reporter at said different times to determine whether therapy in said patient is progressing. In some aspects, the patient is administered said particles or protocells at about the same time that therapy is commenced and at least one time thereafter to determine the number of amount of said particles or protocells or said diagnostic agents which bind to bone tissue in said patient at the start of therapy and alter a period of therapy, wherein a reduction in the binding/incorporation of said particles or protocells and/or said reporter after a period of treatment is indicative that the therapy is favorably treating the cancer.

Definitions

The following terms shall be used throughout the specification. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed. The upper and lower limits of these smaller ranges may independently be included in the smaller ranges is also encompassed, subject to any specifically excluded limit in the stated range. Where the stated range includes one or both of the limits, ranges excluding either both of those included limits are also included. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art. Although any methods and materials similar or equivalent to those described herein can also be used in the practice or testing, the exemplary methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal or a human, to whom treatment, including prophylactic treatment (prophylaxis), with the compounds or compositions is provided. For treatment of those infections, conditions or disease states which are specific for a specific animal such as a human patient, the term patient refers to that specific animal. In most instances, the patient or subject is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "compound" is used herein to describe any specific compound or bioactive agent disclosed herein, including any and all stereoisomers (including diastereomers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein.

The term "bioactive agent" refers to any biologically active compound or drug which may be formulated for use in an embodiment. Exemplary bioactive agents include the compounds which are used to treat cancer or a disease state or condition which occurs secondary to cancer and may include antiviral agents, especially anti-HIV, anti-HBV and/or anti-HCV agents (especially where hepatocellular cancer is to be treated) as well as other compounds or agents which are otherwise described herein.

The terms "treat", "treating", and "treatment", are used synonymously to refer to any action providing a benefit to a patient at risk for or afflicted with a disease, including improvement in the condition through lessening, inhibition, suppression or elimination of at least one symptom, delay in progression of the disease, prevention, delay in or inhibition of the likelihood of the onset of the disease, etc. In the case of viral infections, these terms also apply to viral infections and may include, in certain particularly favorable embodiments the eradication or elimination (as provided by limits of diagnostics) of the virus which is the causative agent of the infection.

Treatment, as used herein, encompasses both prophylactic and therapeutic treatment, principally of cancer, but also of other disease states. Compounds can, for example, be administered prophylactically to a mammal in advance of the occurrence of disease to reduce the likelihood of that disease, especially metastasis of bone cancer. Prophylactic administration is effective to reduce or decrease the likelihood of the subsequent occurrence of disease in the mammal, or decrease the severity of disease (inhibition) that subsequently occurs, especially including metastasis of cancer. Alternatively, compounds can, for example, be administered therapeutically to a mammal that is already afflicted by disease. In one embodiment of therapeutic administration, administration of the present compounds is effective to eliminate the disease and produce a remission or substantially eliminate the likelihood of metastasis of a cancer. Administration of the compounds is effective to decrease the severity of the disease or lengthen the lifespan of the mammal so afflicted, as in the case of cancer, or inhibit or even eliminate the likelihood of disease, especially the metastasis of cancer to become metastatic bone cancer.

The term "pharmaceutically acceptable" as used herein means that the compound or composition is suitable for administration to a subject, including a human patient, to achieve the treatments described herein, without unduly deleterious side effects in light of the severity of the disease and necessity of the treatment.

The term "inhibit" as used herein refers to the partial or complete elimination of a potential effect, while inhibitors are compounds/compositions that have the ability to inhibit.

The term "prevention" when used in context shall mean "reducing the likelihood" or preventing a disease, condition or disease state from occurring as a consequence of administration or concurrent administration of one or more compounds or compositions, alone or in combination with another agent. It is noted that prophylaxis will rarely be 100% effective; consequently the terms prevention and reducing the likelihood are used to denote the fact that within a given population of patients or subjects, administration with compounds will reduce the likelihood or inhibit a particular condition or disease state (in particular, the worsening of a disease state such as the growth or metastasis of cancer) or other accepted indicators of disease progression from occurring.

The term "particle" is used to describe a porous nanoparticle which is made of a material comprising silica, polystyrene, alumina, titania, zirconia, or generally metal oxides, organometallates, organosilicates or mixtures thereof.

The terms "nanoparticulate" and "porous nanoparticulate" are used interchangeably herein and such particles may exist in a crystalline phase, an amorphous phase, a semicrystalline phase, a semi amorphous phase, or a mixture thereof.

The phrase "effective average particle size" as used herein to describe a multiparticulate (e.g., a porous nanoparticulate) means that at least 50% of the particles therein are of a specified size. Accordingly, "effective average particle size of less than about 2,000 nm in diameter" means that at least 50% of the particles therein are less than about 2000 nm in diameter. In certain embodiments, nanoparticulates have an effective average particle size of less than about 2,000 nm (i.e., 2 microns), less than about 900 nm, less than about 1,800 nm, less than about 1,700 nm, less than about 1,600 nm, less than about 1,500 nm, less than about 1,400 nm, less than about 1,300 nm, less than about 1,200 nm, less than about 1,100 nm, less than about 1,000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, Jess than about 100 nm, less than about 75 nm, or Jess than about 50 nm, as measured by light-scattering methods, microscopy, or other appropriate methods. "D50" refers to the particle size below which 50% of the particles in a multi particulate fall. Similarly, "$D_{90}$" is the particle size below which 90% of the particles in a multiparticulate fall.

"Amine-containing silanes" include, but are not limited to, a primary amine, a secondary amine or a tertiary amine functionalized with a silicon atom, and may be a monoamine or a polyamine such as diamine. For example, the amine-containing silane is N-(2-aminoethyl)-3-aminopropyltrimethoxysilane (AEPTMS). Non-limiting examples of amine-containing silanes also include 3-aminopropyltrimethoxysilane (APTMS) and 3-aminopropyltriethoxysilane (APTS), as well as an amino-functional trialkoxysilane. Protonated secondary amines, protonated tertiary alkyl amines, protonated amidines, protonated guanidines, protonated pyridines, protonated pyrimidines, protonated pyrazines, protonated purines, protonated imidazoles, protonated pyrroles, quaternary alkyl amines, or combinations thereof, can also be used. These are used to modify the charge (Zeta potential) of the nanoparticle, which typically has a negative Zeta charge to something which is more neutral or even more positive in character.

The term "bone cancer" is used to describe a primary cancer of the bone. Bone cancer is an uncommon cancer that begins in a bone. Bone cancer can begin in any bone in the body, but it most commonly affects the long bones that make up the arms and legs. Several types of bone cancer exist. Some types of bone cancer occur primarily in children, while others affect mostly adults. The term "metastatic bone cancer" is used to describe cancers that begin elsewhere in the body and spread (metastasize) to the bone. These cancers are often named for the tissue where they began, such as prostate cancer or breast cancer that has metastasized to the bone. "Bone metastasis" occurs when cancer cells spread from their original site to a bone. Nearly all types of cancer can spread (metastasize) to the bones. Certain types of cancer are particularly likely to spread to bone, including breast cancer and prostate cancer. Bone metastasis can occur in any bone but more commonly occurs in the spine, pelvis and thigh. Bone metastasis may be the first sign that you have cancer, or bone metastasis may occur years after cancer treatment.

The terms "coadminister" and "coadministration" are used synonymously to describe the administration of at least one of the particle or protocell compositions in combination with at least one other agent, which agent can include an agent in another particle or protocell composition, often at least one additional anti-cancer agent in a particle or protocell or otherwise as described herein, which are specifically disclosed herein in amounts or at concentrations which would be considered to be effective amounts at or about the same time. While coadministered compositions/agents may be administered at the same time, agents may be administered at times such that effective concentrations of both (or more) compositions/agents appear in the patient at the same time for at least a brief period of time. Alternatively, in certain aspects, it may be possible to have each coadministered composition/agent exhibit its inhibitory effect at different times in the patient, with the ultimate result being the inhibition and treatment of cancer, especially including bone cancer, especially metastatic bone cancer, as well as the reduction or inhibition of other disease states, conditions or complications. Of course, when more than one disease state, infection or other condition is present, the present compounds may be combined with other agents to treat that other infection or disease or condition as required. The term "anticancer agent" or "additional anticancer agent" is used to describe mean a chemotherapeutic agent such as an agent selected from the group consisting of microtubule stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes. These may be selected from the group consisting of a FLT-3 inhibitor, a VEGFR inhibitor, an EGFR TK inhibitor, an aurora kinase inhibitor, a PK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a P13 kinase inhibitors, an AKT inhibitor, a JAK/ST AT inhibitor, a checkpoint-I or 2 inhibitor, a focal adhesion kinase inhibitor, a Map kinase (mek) inhibitor, a VEGF trap antibody, everolimus, trabectedin, abraxane, TLK 286 (canfosfamide), AV-299 (ficlatuzumab), DN-101 (calcitriol), pazopanib, GSK690693 (4-2-(4-amino-1,2,5-oxadiazol-3-yl)-1-ethyl-7-R(3S)-3-piperidinylmethoxy]-1H-imidazo[4,5-c[pyridin-4-yl]-2-methyl-3-butyn-2-ol), RTA 744 (berubicin), AZD 6244 (selumetinib), AMN-107 (nilotinib), TKI-258 (dovitinib), GSK461364 ((R)-5-46-(4-methyl-1-piperazin]methyl-1H-benzimidazol-1-yl]-3-(1r)-142-(trifluoromothyl)phenyl]ethoxyl-2-thiophenecarboxamide), AZD 1152 (barasertib), enzastaurin, vandetanib, ARQ-197 (tivantinib), MK-0457 (tozasertib), MLN8054 ([[9-Chloro-7-(2,6-difluorophenyl)-5H-pyrimido [5,4-d][2]benzazepin-2-yl]aminobenzoic acid), PHA-739338 (danusertib), R-763 (cenisertib), pemetrexed, erlotinib, amrubicin, oregovomab, Lep-etu (liposomal paclitaxel), nolatrexed, azd2171, batabulin, ofatumumab, zanclimumab, edotecarin, tetrandrine, rubitecan, tesmilifene, oblimersen, ticilimumab, ipilimumab, gossypol, 131-1-TM-60 (iodine-131 substituted chlorotoxin), CC 8490 (custirsen), cilengitide, gimatecan, IL13-PE3800R (human IL-13 conjugated with a truncated *Pseudomonas* exotoxin), INO 1001 (N-[3-(4-Morpholinyl)propyl]-5-oxo-6,11-dihydro-5H-Indeno[1,2-c]is oquinoline-9-sulfonamide),lucanthone, LY 317615 (enzastaurin), neuradiab, vitespen, Sdx 102 (L-Alanosine), talampanel, atrasentan, romidepsin, sunitinib, 5-flurouracil, vorinostat, etoposide, gemcitabine, doxorubicin, liposomal doxorubicin, 5'-deoxy-5-fluorouridine, vincristine, temozolomide, ZK-304709 ((S)-4-((5-bromo-4-((1-hydroxypropan-2-yl)amino)pyrimidin-2-yl) amino)benzenesulfonamide), seliciclib; PD0325901 (mirdametinib), capecitabine, L-Glutamic acid, N-[4-[2-(2-amino-4,7-dihydro-4-oxo-1 H-pyrrolo[2,3-d]pyrimidin-5-yl]ethyl]benzoyl]-disodium salt hepahydrate, camptothecin, PEG-labeled irinotecan, tamoxifen, toremifene citrate, anastrozole, exemestane, letrozole, DES(diethylstilbestrol), estradiol, estrogen, conjugated estrogen, bevacizumab, IMC-1C11 (antibody against human vascular endothelial growth factor 2), 3-[5-(methylsulfonylpiperadinemethyl)-indolyl]-quinolone, vatalanib, AG-013736 (axitinib), AVE-0005, (pyro-Glu-His-Trp-Ser-Tyr-D-Ser(Bu t)-Leu-Arg-Pro-Azgly-NH2 (SEQ ID NO: 9) acetate $[C_{59}H_{84}O_{14}$-$C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714 (2-Methoxy-N-1(2E)-3 4-43-methyl-4-4(6-methyl-3-pyridinyl)oxy]phenyl]amino]-6-quinazolinyl]-2-propen-1-yl]acetamide), TAK.-165 (mubritinib), HKI-272 (neratinib), erlotinib, lapatinib, canertinib, ABX-EGF antibody (panitumumab), cetuximab, lonafamib, BMS-214662 ((3R)-2,3,4,5-Tetrahydro-1-(1H-Imidazol-4-ylmethyl)-3-(phenylmethyl)-4-(2-thienylsulfonyl)-1H-1,4-benzodiazepine-7-carbonitrile), tipifarnib, amifostine, NVP-LAQ824 (dacinostat), suberoyl anilide hydroxamic acid, valproic acid, trichostatin A, FK-228 (romidepsin), sorafenib, KRN951 (tivozanib), aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis retinoic acid, phenylalanine mustard, aracil mustard, estramustine, altretamine, floxuridine, 5-deoxyuridine, cytosine arabinoside, 6-mercaptopurine, deoxycoformycin, calcitriol, valrubicin, mithramycin, vinblastine, vinorelbine, topotecan, razoxin, marimastat, COL-3 (incyclinide), neovastat, BMS-275291 (rebimastat), squalamine, endostatin, SU5416 (semaxanib), EMD121974 (cilengitide), interleukin-12, IM862 (glufanide disodium), angiostatin, vitaxin, droloxifene, idoxifene, spironolactone, finasteride, cimetidine, trastuzumab, denileukin diftitox, gefitinib, bortezomib, paclitaxel, cremophor-free paclitaxel, docetaxel, epithilone B, BMS-247550 (ixabepilone), BMS-310705 (21-aminoepothilone B), droloxifene, 4-hydroxytamoxifen, pipendoxifene, ERA-923 (pipendoxifene), arzoxifene, fulvestrant, acolbifene, lasofoxifene, idoxifene, TSE-424 (bazedoxifene), HMR-3339 (4-Chloro-11b-(4-(2-(diethylamino) ethoxy)phenyl)-estra-1,3,5(10)-triene-3,17b-diol), PTK787/ZK 222584 (1-44-chloroanilino-4-[4-pyridylmethyl] phthalazine succinate), VX-745 (neflamapimod), rapamycin, 40-O-(2-hydroxyethy)-rapamycin, temsirolimus, AP-23573 (ridaforolimus), ABT-578 (zotarolimus), LY294002 (2-(4-Morpholinyl)-8-phenyl-4H-1-benzopyran-4-one), LY292223 ((2S,4R)-4-Mercapto-2-(2,4,5-trifluorobenzyloxymethyl)-pyrolidine-1-carboxylic acid 2-methoxycarbonyl-phenyl ester), LY292696 (2;-Thiomorpholinyl)-4H-1-benzopyran-4-one), LY293684 (3-(4 Morpholinyl)-1H-naphtho[2,1-b]pyran-1-one), LY293646 (2-(4 Morpholinyl)-4H-naphtho[1.2-b]pyran-4-one), wortmannin, ZM336372 (3-(Dimethylamino)-N-13-1(4-hydroxybenzoyl)aminol-4-methylphenyl]benzamide), L-779,450 (2-chloro-5-(2-phenyl-5-(pyridin-4-yl)-1H-imidazol-4-yl) phenol), PEG-filgrastim, darbepoetin, erythropoietin, granulocyte colony-stimulating factor, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, etidronate, mitotane, cyclosporine, liposomal daunorubicin, Edwina-asparaginase, strontium 89, casopitant, netupitant, a NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochiorperazine, granisetron, ondansetron, dolasetron, tropisetron, pegfilgrastim, erythropotetin, epoetin alfa, and darbepoetin alfa, among others.

The terms "cell penetration peptide", "fusogenic peptide" and "endosomolytic peptide" are used to describe a peptide which aids particle or protocell translocation across a lipid bilayer, such as a cellular membrane or endosome lipid bilayer and is optionally crosslinked onto a lipid bilayer surface of the particles or protocells. Endosomolytic peptides are a sub-species of fusogenic peptides as described herein. In both the multilamellar and single layer particle or protocell embodiments, the nonendosomolytic fusogenic peptides (e.g., electrostatic cell penetrating peptide such as R8 octaarginine) are incorporated onto the particles or protocells at the surface of the particle or protocell in order to facilitate the introduction of particles or protocells into targeted cells (APCs) to effect an intended result (to instill an immunogenic and/or therapeutic response as described herein). The endosomolytic peptides (often referred to in the art as a subset of fusogenic peptides) may be incorporated in the surface lipid bilayer of the particle or protocell or in a lipid sublayer of the multilamellar in order to facilitate or assist in the escape of the particle or protocell from endosomal bodies. Representative and exemplary electrostatic cell penetration (fusogenic) peptides for use in particles or protocells include an 8-mer polyarginine ($H_2N$-RRRRRRRR-COOH, SEQ ID NO: 1), among others known in the art, which are included in particles or protocells in order to enhance the penetration of the particle or protocell into cells. Representative endosomolytic fusogenic peptides ("endosomolytic peptides") include H5WYG peptide, $H_2N$-GLFHAIAHFIHGGWHGLIHGWYGGC-COOH (SEQ ID NO:2) or $H_2N$-GLFHAIAHFIHGGWHGLIHGWYGGGC-COOH (SEQ ID NO:7), or a portion thereof, e.g., GLFHAIAHFIHGGWHGLIHGWY (SEQ ID NO:8), RALA peptide ($NH_2$-WEARLARALARALARHLARALARALRAGEA-COOH, SEQ ID NO:3), KALA peptide ($NH_2$-WEAK-LAKALAKALAKHLAKALAKALKAGEA-COOH), SEQ ID NO:4), GALA, (NH2-WEAALAEALAEALAEH-LAEALAEALEALAA-COOH, SEQ ID NO:5) and INF7 (NH2-GLFEAIEGFIENGWEGMIDGWYG-COOH, SEQ ID NO:6), among others. At least one endosomolytic peptide is included in particles or protocells in combination with a viral antigen (often pre-ubiquitinylated) and/or a viral plasmid (which expresses viral protein or antigen) in order to produce CD8+ cytotoxic T cells pursuant to a MHC class I pathway (see FIG. 4 or 6).

In order to covalently link any of the fusogenic peptides or endosomolytic peptides to components of the lipid bilayer, various approaches, well known in the art may be used. For example, the peptides listed above could have a C-terminal poly-His tag, which would be amenable to Ni-NTA conjugation (lipids commercially available from Avanti). In addition, these peptides could be terminated with a C-terminal cysteine for which heterobifunctional crosslinker chemistry (EDC, SMPH, etc. . . . ) to link to aminated lipids would be useful. Another approach is to modify lipid constituents with thiol or carboxylic acid to use the same crosslinking strategy. All known crosslinking approaches to crosslinking peptides to lipids or other components of a lipid layer could be used. In addition we could use click chemistry to modify the peptides with azide or alkyne for Cu-catalyzed crosslinking, and one could also use a cu-free click chemistry reaction.

The term "crosslinking agent" is used to describe a bifunctional compound of varying length containing two different functional groups which may be used to covalently link various components to each other. Crosslinking agents may contain two electrophilic groups (to react with nucleophilic groups on peptides of oligonucleotides, one electrophilic group and one nucleophilic group or two nucleophilic groups). The crosslinking agents may vary in length depending upon the components to be linked and the relative flexibility required. Crosslinking agents are used to anchor targeting and/or fusogenic peptides to the phospholipid bilayer, to link nuclear localization sequences to histone proteins for packaging supercoiled plasmid DNA and in certain instances, to crosslink lipids in the lipid bilayer of the particles or protocells. There are a large number of crosslinking agents which may be used, many commercially available or available in the literature. Exemplary crosslinking agents include, for example, I-Ethyl-3-(3-dimethylaminopropylicarbodiimide hydrochloride (EDC), succinimidyl 4-[N-maleimidomethyl] cyclohexane-1-carboxylate (SMCC), Succinimidyl 6-[β-Maleimidopropionamido] hexanoate (SMPH), N-(β-Maleimidopropionic acid] hydrazide (BMPH), NHS-$(PEG)_n$-maleimide, succinimidyl-[(N-maleimidopropionamido)tetracosaethyleneglycol] ester (SM$(PEG)_{24}$), succinimidyl 6-[3'-(2-pyridyldithio)-propionamido] hexanoate (LC-SPDP), N-α-maleimidoacet-oxysuccinimide ester (AMAS), dibenzocyclooctyne-N-hydroxysuccinimidyl ester (DBCO-NHS) among others.

As discussed in detail herein, the porous nanoparticle core can include porous nanoparticles having at least one dimension, for example, a width or a diameter of about 3000 nm or less, about 1000 nm or less, about 500 nm or less, about 200 nm or less. For example, the nanoparticle core is spherical with a diameter of about 500 nm or less, or about 8-10 nm to about 200 nm. In embodiments, the porous particle core can have various cross-sectional shapes including a circular, rectangular, square, or any other shape. In certain embodiments, the porous particle core can have pores with a mean pore size ranging from about 2 nm to about 30 nm, although the mean pore size and other properties (e.g., porosity of the porous particle core) are not limited in accordance with various embodiments of the present teachings.

Nanoparticles

Porous nanoparticulates include mesoporous silica nanoparticles and core-shell nanoparticles. The porous nanoparticulates can be biodegradable polymer nanoparticulates comprising one or more compositions selected from the group consisting of aliphatic polyesters, poly (lactic acid) (PLA), poly (glycolic acid) (PGA), co-polymers of lactic acid and glycolic acid (PLGA), polycaprolactone (PCL), polyanhydrides, poly(ortho)esters, polyurethanes, poly(butyric acid), poly(valeric acid), poly(lactide-co-caprolactone), alginate and other polysaccharides, collagen, and chemical derivatives thereof, albumin a hydrophilic protein, zein, a prolamine, a hydrophobic protein, and copolymers and mixtures thereof.

A porous spherical silica nanoparticle in one embodiment is used for particles or protocells and is surrounded by a supported lipid or polymer bilayer or multilayer. Various embodiments provide nanostructures and methods for constructing and using the nanostructures and providing particles or protocells. Many of the particles or protocells in their most elemental form are known in the art. Porous silica particles of varying sizes ranging in size (diameter) from less than 5 nm to 200 nm or 500 nm or more are readily available in the art or can be readily prepared using methods known in the art or alternatively, can be purchased from SkySpring Nanomaterials, Inc., Houston, Tex., USA or from Discovery Scientific, Inc., Vancouver, British Columbia. Multimodal silica nanoparticles may be readily prepared using the procedure of Carroll, et al., *Langmuir*, 25, 13540-13544 (2009). Particles or protocells can be readily obtained using methodologies known in the art. The examples section of the present application provides certain methodology for obtaining particles or protocells. Particles or protocells may be readily prepared, including particles or protocells comprising lipids which are fused to the surface of the silica nanoparticle. See, for example, Liu et al. (2009), Liu et al. (2009), Liu et al. (2009) Lu et al. (1999), Exemplary particles or protocells are prepared according to the procedures which are presented in Ashley et al. (2011), Lu et al. (1999), Carroll et al. (2009), and as otherwise presented in the experimental section which follows.

A nanoparticle may have a variety of shapes and cross-sectional geometries that may depend, in part, upon the process used to produce the particles. In one embodiment, a nanoparticle may have a shape that is a sphere, a rod, a tube, a flake, a fiber, a plate, a wire, a cube, or a whisker. A nanoparticle may include particles having two or more of the aforementioned shapes. In one embodiment, a cross-sectional geometry of the particle may be one or more of circular, ellipsoidal, triangular, rectangular, or polygonal. In one embodiment, a nanoparticle may consist essentially of non-spherical particles. For example, such particles may have the form of ellipsoids, which may have all three principal axes of differing lengths, or may be oblate or prelate ellipsoids of revolution. Non-spherical nanoparticles alternatively may be laminar in form, wherein laminar refers to particles in which the maximum dimension along one axis is substantially less than the maximum dimension along each of the other two axes. Non-spherical nanoparticles may also have the shape of frusta of pyramids or cones, or of elongated rods. In one embodiment, the nanoparticles may be irregular in shape. In one embodiment, a plurality of nanoparticles may consist essentially of spherical nanoparticles.

In certain embodiments, the porous nanoparticulates are comprised of one or more compositions selected from the group consisting of silica, a biodegradable polymer, a solgel, a metal and a metal oxide.

In an embodiment, the nanostructures include a core-shell structure which comprises a porous particle core optionally surrounded by a shell of lipid, e.g., a bilayer, but possibly a monolayer or multilayer (see Liu, et al., *JACS*, 2009, Id). The porous particle core can include, for example, a porous nanoparticle made of an inorganic and/or organic material as set forth above surrounded by a lipid bilayer. In one embodiment, these lipid bilayer surrounded nanostructures are referred to as "protocells" or "functional protocells," since they have a supported lipid bilayer membrane structure. In some embodiments, the porous particle core of the protocells can be loaded with various desired species ("cargo"), including small molecules (e.g. anticancer agents as otherwise described herein), large molecules (e.g. including macromolecules such as RNA, including small interfering RNA or siRNA or small hairpin RNA or shRNA or a polypeptide which may include a polypeptide toxin such as a ricin toxin A-chain or other toxic polypeptide such as diphtheria toxin A-chain DTx, among others) or a reporter polypeptide (e.g., fluorescent green protein, among others) or semiconductor quantum dots, or metallic nanoparticles, or metal oxide nanoparticles or combinations thereof. In certain aspects, the particles or protocells are loaded with super-coiled plasmid DNA, which can be used to deliver a therapeutic and/or diagnostic peptide(s) or a small hairpin RNA/shRNA or small interfering RNA/siRNA which can be used to inhibit expression of proteins (such as, for example growth factor receptors or other receptors which are responsible for or assist in the growth of a cell especially a cancer cell, including epithelial growth factor/EGFR, vascular endothelial growth factor recepto/VEGFR-2 or platelet derived growth factor receptor/PDGFR-a, among numerous others, and induce growth arrest and apoptosis of cancer cells).

In certain embodiments, the cargo components can include, but are not limited to, chemical small molecules (especially anticancer agents, nucleic acids (DNA and RNA, including siRNA and shRNA and plasmids which, after delivery to a cell, express one or more polypeptides or RNA molecules), such as for a particular purpose, such as a therapeutic application or a diagnostic application as otherwise disclosed herein.

In some embodiments, the lipid bilayer of protocells can provide biocompatibility and can be modified to possess targeting species including, for example, targeting peptides including antibodies, aptamers, and PEG (polyethylene glycol) to allow, for example, further stability of the protocells and/or a targeted delivery into a bioactive cell.

The particle size distribution, depending on the application, may be monodisperse or polydisperse. The silica cores can be rather monodisperse (i.e., a uniform sized population varying no more than about 5% in diameter, e.g., ±10-nm for a 200 nm diameter particle especially if they are prepared using solution techniques) or rather polydisperse (i.e., a polydisperse population can vary widely from a mean or medium diameter, e.g., up to ±200-nm or more if prepared by aerosol. Polydisperse populations can be sized into monodisperse populations. All of these are suitable for particle or protocell formation. In one embodiment, particles or protocells are no more than about 500 nm in diameter, or no more than about 200 run in diameter in order to afford delivery to a patient or subject and produce an intended therapeutic effect.

In certain embodiments, particles or protocells generally range in size from greater than about 8-10 nm to about 5 μm in diameter, about 20-nm to about 3 μm in diameter, about 10 nm to about 500 nm, or about 20-200-nm (including about 150 nm, which may be a mean or median diameter). As discussed above, the particle or protocell population may be considered monodisperse or polydisperse based upon the mean or median diameter of the population. Size is very important to therapeutic and diagnostic aspects as particles smaller than about 8-nm diameter are excreted through kidneys, and those particles larger than about 200 nm are trapped by the liver and spleen. Thus, an embodiment focuses in smaller sized particles or protocells for drug delivery and diagnostics in the patient or subject.

In certain embodiments, protocells having particles are characterized by containing mesopores, pores which are found in the nanostructure material. These pores (at least one, but often a large plurality) may be found intersecting the surface of the nanoparticle (by having one or both ends of the pore appearing on the surface of the nanoparticle) or internal to the nanostructure with at least one or more mesopore interconnecting with the surface mesopores of the nanoparticle. Interconnecting pores of smaller size are often found internal to the surface mesopores. The overall range of pore size of the mesopores can be 0.03-50-nm in diameter. Pore sizes of mesopores may range from about 2-30 nm; they can be monosized or bimodal or graded—they can be ordered or disordered (essentially randomly disposed or worm-like).

Mesopores (IUPAC definition 2-50-nm in diameter) are 'molded' by templating agents including surfactants, block copolymers, molecules, macromolecules, emulsions, latex beads, or nanoparticles. In addition, processes could also lead to micropores (IUPAC definition less than 2-nm in diameter) all the way down to about 0.03-nm, e.g., if a templating moiety in the aerosol process is not used. They could also be enlarged to macropores, i.e., 50-nm in diameter.

Pore surface chemistry of the nanoparticle material can be very diverse—all organosilanes yielding cationic, anionic, hydrophilic, hydrophobic, reactive groups—pore surface chemistry, especially charge and hydrophobicity, affect loading capacity. Attractive electrostatic interactions or hydrophobic interactions control/enhance loading capacity and control release rates. Higher surface areas can lead to higher loadings of drugs/cargos through these attractive interactions. See below.

In certain embodiments, the surface area of nanoparticles, as measured by the N2 BET method, ranges from about 100 m2/g to >about 1200 m2/g. In general, the larger the pore size, the smaller the surface area. The surface area theoretically could be reduced to essentially zero, if one does not remove the templating agent or if the pores are sub-0.5-nm and therefore not measurable by N2 sorption at 77K due to kinetic effects. However, in this case, they could be measured by $CO_2$ or water sorption, but would probably be considered non-porous. This would apply if biomolecules are encapsulated directly in the silica cores prepared without templates, in which case particles (internal cargo) would be released by dissolution of the silica matrix after delivery to the cell.

Typically the particles or protocells are loaded with cargo to a capacity up to over 100 weight %; defined as (cargo weight/weight of particle or protocell)×100. The optimal loading of cargo is often about 0.01 to 30% but this depends on the drug or drug combination which is incorporated as cargo into the particle or protocell. This is generally expressed in μM per $10^{10}$ particles where we have values ranging from 2000-100 μM per $10^{10}$ particles. Particles or protocells may exhibit release of cargo at pH about 5.5, which is that of the endosome, but are stable at physiological pH of 7 or higher (e.g., 7.4).

The surface area of the internal space for loading is the pore volume whose optimal value ranges from about 1.1 to 0.5 cubic centimeters per gram (cc/g). Note that in the particles or protocells according to one embodiment, the surface area is mainly internal as opposed to the external geometric surface area of the nanoparticle.

The lipid bilayer if present supported on the porous particle according to one embodiment has a lower melting transition temperature, e.g., is more fluid than a lipid bilayer supported on a non-porous support or the lipid bilayer in a liposome. This is sometimes important in achieving high affinity binding of targeting ligands at low peptide densities, as it is the bilayer fluidity that allows lateral diffusion and recruitment of peptides by target cell surface receptors. One embodiment provides for peptides to cluster, which facilitates binding to a complementary target. Lipid bilayers may be prepared using any method known in the art, but often the bilayers are fused onto MSNPs. In this approach, MSNPs are mixed with liposomes in aqueous buffer and washed to remove free liposomes in solution.

In the present disclosure, the lipid bilayer may vary significantly in composition. Ordinarily, any lipid or polymer which is may be used in liposomes may also be used in protocells. In one embodiment, lipid bilayers for use in protocells comprise a mixtures of lipids (as otherwise described herein) at a weight percent of 5% DOPE, 5% PEG, 30% cholesterol, 60% DOPC or DPPC. Additional lipid bilayers comprise a mixture of lipids 60% DSPC, 30% DOPE, 10% Cholesterol (weight percent.); 60% DSPC, 15% DOPE, 15% Cholesterol and 10% DSPE-PEG 2000 (weight percent) and 60% DSPC, 15% DSPE, 15% Cholesterol and 10% DSPE-PEG 2000 (weight percent).

The charge of the MSNP core as measured by the Zeta potential may be varied monotonically from −50 to +50 mV by modification with the amine-containing silane, for example, 2-(aminoethyl) propyltrimethoxy-silane (AE-PTMS) or other organosilanes, as disclosed herein. This charge modification, in turn, varies the loading of the drug within the cargo of the particle or protocell. Generally, after fusion of the supported lipid bilayer, the zeta-potential is reduced to between about −I0 mV and +5 mV, which is important for maximizing circulation time in the blood and avoiding non-specific interactions.

Depending on how the surfactant template is removed, e.g., calcination at high temperature (500° C.) versus extraction in acidic ethanol, and on the amount of AEPTMS or other amine-containing silane incorporated in the silica: framework, the silica dissolution rates can be varied widely. This in turn controls the release rate of the internal cargo. This occurs because molecules that are strongly attracted to the internal surface area of the pores diffuse slowly out of the particle cores, so dissolution of the particle cores controls in part the release rate.

Further characteristics of particles or protocells according to an embodiment are that they are stable at pH 7, i.e., they don't leak their cargo, but at pH 5.5, which is that of the endosome lipid or polymer coating becomes destabilized initiating cargo release. This pH-triggered release is important for maintaining stability of the particle or protocell up until the point that it is internalized in the cell by endocytosis, whereupon several pH triggered events cause release into the endosome and consequently, the cytosol of the cell. The protocell core particle and surface can also be modified to provide non-specific release of cargo over a specified, prolonged period of time, as well as be reformulated to release cargo upon other biophysical changes, such as the increased presence of reactive oxygen species and other factors in locally inflamed areas. Quantitative experimental evidence has shown that targeted particles or protocells elicit only a weak immune response, because they do not support T-Cell help required for higher affinity IgG, a favorable result.

The surface area of the internal space for loading is the pore volume whose optimal value ranges from about 1.1 to 0.5 cubic centimeters per gram (cc/g). Note that in the case of nanoparticles the surface area is mainly external, but can also be highly internal, depending on the nature of the mesopores in the nanoparticles.

Mesoporous silica nanoparticles can be, e.g., from around 5 nm to around 500 nm in size, including all integers and ranges there between. The size is measured as the longest axis of the particle. In various embodiments, the particles are from around 10 nm to around 500 nm and from around 10 nm to around 100 nm in size. The mesoporous silica nanoparticles have a porous structure. The pores can be from around 1 to around 20 nm in diameter, including all integers and ranges there between. In one embodiment, the pores are from around 1 to around 10 nm in diameter. In one embodiment, around 90% of the pores are from around 1 to around 20 nm in diameter. In another embodiment, around 95% of the pores are around 1 to around 20 nm in diameter.

The mesoporous nanoparticles can be synthesized according to methods known in the art. In one embodiment, the nanoparticles are synthesized using sol-gel methodology where a silica precursor or silica precursors and a silica precursor or silica precursors conjugated (i.e., covalently bound) to absorber molecules are hydrolyzed in the presence of templates in the form of micelles. The templates are formed using a surfactant such as, for example, hexadecyltrimethylammonium bromide (CTAB). It is expected that any surfactant which can form micelles can be used.

The core-shell nanoparticles comprise a core and shell. The core comprises silica and an absorber molecule. The absorber molecule is incorporated in to the silica network via a covalent bond or bonds between the molecule and silica network. The shell comprises silica.

In one embodiment, the core is independently synthesized using known sol-gel chemistry, e.g., by hydrolysis of a silica precursor or precursors. The silica precursors are present as a mixture of a silica precursor and a silica precursor conjugated, e.g., linked by a covalent bond, to an absorber molecule (referred to herein as a "conjugated silica precursor"). Hydrolysis can be carried out under alkaline (basic) conditions to form a silica core and/or silica shell. For example, the hydrolysis can be carried out by addition of ammonium hydroxide to the mixture comprising silica precursor(s) and conjugated silica precursor(s).

Silica precursors are compounds which under hydrolysis conditions can form silica. Examples of silica precursors include, but are not limited to, organosilanes such as, for example, tetraethoxysilane (TEOS), tetramethoxysilane (TMOS), and the like.

The silica precursor used to form the conjugated silica precursor has a functional group or groups which can react with the absorbing molecule or molecules to form a covalent bond or bonds. Examples of such silica precursors include, but is not limited to, isocyanatopropyltriethoxysilane (ICPTS), (3-glycolyl oxypropyl) trimethoxysilane, aminopropyltrimethoxysilane (APTS), mercaptopropyltrimethoxysilane (MPTS), APTES (3-aminopropyl)triethoxysilane), APMDES (3-aminopropylmethyl diethoxysilane, APDMES (3-aminopropyl)-dimethyl-ethoxysilane, APMS (3-amino propyl)-trimethtoxysilane, and the like.

In one embodiment, an organosilane (conjugatable silica precursor) used for forming the core has the general formula $R_{4n}SiX_n$, where X is a hydrolyzable group such as ethoxy, methoxy, or 2-methoxy-ethoxy; R can be a monovalent organic group of from 1 to 12 carbon atoms which can optionally contain, but is not limited to, a functional organic group such as mercapto, epoxy, acrylyl, methacrylyl, or amino; and n is an integer of from 0 to 4. The conjugatable silica precursor is conjugated to an absorber molecule and subsequently co-condensed for forming the core with silica precursors such as, for example, TEOS and TMOS. A silane used for forming the silica shell has n equal to 4. The use of functional mono-, bis- and tris-alkoxysilanes for coupling and modification of co-reactive functional groups or hydroxy-functional surfaces, including glass surfaces, is also known, see Kirk-Othmer, Encyclopedia of Chemical Technology, Vol. 20, 3rd Ed., J. Wiley, N.Y.; see also E. Pluedemann, Silane Coupling Agents, Plenum Press, N. Y. 1982. The organo-silane can cause gels, so it may be desirable to employ an alcohol or other known stabilizers. Processes to synthesize core-shell nanoparticles using modified Stober processes can be found in U.S. patent applications Ser. Nos. 10/306,614 and 10/536,569, the disclosure of such processes therein are incorporated herein by reference.

Exemplary Biphosphonates to Treat Bone Metastasis

Bone metastasis can cause pain and broken bones. With rare exceptions, cancer that has spread to the bones can't be cured. Treatments can help reduce pain and other symptoms of bone metastases. Bone metastasis often causes no signs and symptoms, but when symptoms do occur, these symptoms can include bone pain, broken bones, urinary incontinence, bowel incontinence, weakness in the legs or arms and hypercalcemia, which can cause vomiting constipation and confusion.

The term "bisphosphonate" is used to describe a compound according to the chemical structure:

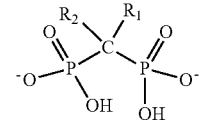

or a salt or an ionic form thereof,

Where $R_1$ is H, OH or halogen (e.g., F or Cl) and $R_2$ is halogen (e.g., F or Cl, more often Cl), $C_1$-$C_6$ alkyl (e.g., methyl, ethyl, n-propyl, isopropyl, etc.), amino (e.g., —$NR^{N1}R^{N2}$, where each of $R^{N1}$ and $R^{N2}$ is, independently, H, optionally substituted $C_1$-$C_{12}$ alkyl, or optionally substituted $C_3$-$C_8$ cycloalkyl, or $R^{N1}$ and $R^{N2}$, taken together with the nitrogen atom to which each are attached, form a heterocyclyl group), $C_1$-$C_6$ alkylene amine or a $C_1$-$C_6$ alkylene mono- or dialkyl amine (e.g., ethyl amine, propyl amine or pentyl amine, such as —Alk-$NR^{N1}R^{N2}$, where Alk is optionally substituted $C_1$-$C_6$ alkylene, and each of $R^{N1}$ and $R^{N2}$ is, independently, H, optionally substituted $C_1$-$C_{12}$ alkyl, or optionally substituted $C_3$-$C_8$, cycloalkyl, or $R^{N1}$ and $R^{N2}$, taken together with the nitrogen atom to which each are attached, form a heterocyclyl group), an optionally substituted thiophenyl group (e.g., the phenyl group may be substituted with a parachloro group), an alkylene heteroaryl (e.g., a pyridyl or imidazole group, such as —Alk-Het, where Alk is optionally substituted $C_1$-$C_6$ alkylene and Het is an optionally substituted heteroaryl) or a $C_0$-$C_6$ alkylene carboxylic acid group (where the carboxylic acid group is substituted anywhere along the alkylene chain, but may be at the distal end of the alkylene chain).

Exemplary bisphosphonates which may be readily utilized include pamidronate, neridronate or alendronate (e.g., alendronate) because these bisphosphonates may be easily conjugated to a carboxylic acid group on the surface of the MSNP or bisphosphonates which contain a carboxylic acid group which can be readily conjugated to an amine containing phospholipid in the phospholipid bilayer of the particle or protocell. It is noted that all of the bisphosphonates which contain a hydroxyl group as R1 may be conjugated through an isocyanate group to form a urethane group on the surface of the MSNP or the phospholipid bilayer. Exemplary common bisphosphonates which may be used are presented below, with pamidronate, neridronate or alendronate being specific embodiment because of the ease with which these bisphosphonates may be conjugated with a carboxylic acid group.

| Agent | $R_1$ side chain | $R_2$ side chain |
|---|---|---|
| Etidronate | —OH | —$CH_3$ |
| Clodronate | —Cl | —Cl |
| Tiludronate | —H | —S—C$_6$H$_4$—Cl |
| Pamidronate | —OH | —$CH_2$—$CH_2$—$NH_2$ |
| Neridronate | —OH | —$(CH_2)_5$—$NH_2$ |
| Olpadronate | —OH | —$(CH_2)_2N(CH_3)_2$ |
| Alendronate | —OH | —$(CH_2)_3$—$NH_2$ |
| Ibandronate | —OH | —$CH_2$—$CH_2$N(CH$_3$)((CH$_2$)$_4$—CH$_3$) |
| Risedronate | —OH | (3-pyridylethyl) |
| Zoledronate | —OH | (imidazolylmethyl) |

Protocells

In general, protocells are biocompatible. Drugs and other cargo components are often loaded by adsorption and/or capillary filling of the pores of the particle core up to approximately 50% by weight of the final protocell (containing all components). In certain embodiments, the loaded cargo can be released from the porous surface of the particle core (mesopores), wherein the release profile can be determined or adjusted by, for example, the pore size, the surface chemistry of the porous particle core, the pH value of the system, and/or the interaction of the porous particle core with the surrounding lipid bilayer(s) as generally described herein.

In the present disclosure, the porous nanoparticle core used to prepare the protocells can be tuned in to be hydrophilic or progressively more hydrophobic as otherwise described herein and can be further treated to provide a more hydrophilic surface. For example, mesoporous silica particles can be further treated with ammonium hydroxide and hydrogen peroxide to provide a higher hydrophilicity. In some aspects, the lipid bilayer is fused onto the porous particle core to form the protocell. Protocells can include various lipids in various weight ratios, e.g., including 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), I,2-dioleoyl-sn-glycero-3-(phosphor-L-serine] (DOPS), I,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 12-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzaxadiazol-4-yl)amino]lauroyl]-sn-Glycero-3-Phosphocholine (18: 1-12:0 NBD PC), I-palmitoyl-2-{12-[(7-nitro-2-1,3-benzoxadiazol-4-yl)amino]lauroyl}-sn-glycero-3-phosphocholine (16:0-12:0 NBD PC), cholesterol and mixtures/combinations thereof.

Pegylated phospholipids may be included in lipid bilayers in protocells. These pegylated phospholipids include for example, pegylated 1,2-distearoyl-sn-glycero-3-phosphoethanolamine (PEG-DSPE), pegylated 1,2-dialeoyl-sn-glycero-3-phosphoethanolamine (PEG-DOPE), pegylated 1,2-dipalmitoyl-sn-glycero-3-phosphoethanolamine (PEG-DPPE), and pegylated 1,2-dimyristoyl-sn-glycero-3-phosphoethanolamine (PEG-DMPE), among others, including a pegylated ceramide (e.g. Noctanoyl-sphingosine-1-succinylmethoxy-PEG or N-palmitoyl-sphingosine-1-succinylmethoxy-PEG, among others). The PEG generally ranges in size (average molecular weight for the PEG group) from about 350-7500, about 350-5000, about 500-2500, about 1000-2000. Pegylated phospholipids may comprise the entire phospholipid monolayer of hybrid phospholipid protocells, or alternatively they may comprise a minor component of the lipid monolayer or be absent. Accordingly, the percent by weight of a pegylated phospholipid in phospholipid monolayers which make up ranges from 0% to 100%, 0.01% to 99%, about 5%, 10%, 15%, 20%, 25%, 30%, 35%, 40%, 50%, 55%, 60% and the remaining portion of the phospholipid monolayer comprising at least one additional lipid (such as cholesterol, usually in amounts less than about 50% by weight), including a phospholipid.

Certain lipid combinations are often used. These include, for example, DSPC/DOPE/Cholesterol (60/30/10 mass %), DSPC/DOPE/Cholesterol/DSPE-PEG 2000 (60/15/15/10 mass %), and DSPC/DSPE/Cholesterol/DSPE-PEG 2000 (60/15/15/10), among other combinations. The inclusion of a PEG moiety for purposes of increasing residence time and/or bioavailability of the protocells after administration is envisioned.

The lipid bilayer which is used to prepare protocells can be prepared, for example, by extrusion of hydrated lipid films through a filter with pore size of, for example, about 100 run, using standard protocols known in the art or as otherwise described herein. The filtered lipid bilayer films can then be fused with the porous particle cores, for example, by pipette mixing. In certain embodiments, excess amount of lipid bilayer or lipid bilayer films can be used to form the protocell in order to improve the protocell colloidal stability.

In certain diagnostic embodiments, various dyes or fluorescent (reporter) molecules can be included in the protocell cargo (as expressed by as plasmid DNA) or attached to the porous particle core and/or the lipid bilayer for diagnostic purposes. For example, the porous particle core can be a silica core or the lipid bilayer and can be covalently labeled with FITC (green fluorescence), while the lipid bilayer or the particle core can be covalently labeled with FITC Texas red (red fluorescence). The porous particle core, the lipid bilayer and the formed protocell can then be observed by, for example, confocal fluorescence for use in diagnostic applications. In addition, as discussed herein, plasmid DNA can be used as cargo in protocells such that the plasmid may express one or more fluorescent proteins such as fluorescent green protein or fluorescent red protein which may be used in diagnostic applications.

In various embodiments, the protocell is used in a synergistic system where the lipid bilayer fusion or liposome fusion (i.e., on the porous particle core) is loaded and sealed with various cargo components with the pores (mesopores) of the particle core, thus creating a loaded protocell useful for cargo delivery across the cell membrane of the lipid bilayer or through dissolution of the porous nano particle, if applicable. In certain embodiments, in addition to fusing a single lipid (e.g., phospholipids) bilayer, multiple bilayers with opposite charges can be successively fused onto the porous particle core to further influence cargo loading and/or sealing as well as the release characteristics of the final protocell.

A fusion and synergistic loading mechanism can be included for cargo delivery. For example, cargo can be loaded, encapsulated, or sealed, synergistically through liposome fusion on the porous particles. The cargo can include, for example, small molecule drugs (e.g. especially including anticancer drugs and/or antiviral drugs such as anti-HBV or anti-HCV drugs), peptides, proteins, antibodies, DNA (especially plasmid DNA, including the histone-packaged super coiled plasmid DNA), RNAs (including shRNA and siRNA (which may also be expressed by the plasmid DNA incorporated as cargo within the protocells) fluorescent dyes, including fluorescent dye peptides which may be expressed by the plasmid DNA incorporated within the protocell.

In some embodiments, the cargo can be loaded into the pores (mesopores) of the porous particle cores to form the loaded protocell. In various embodiments, any conventional technology that is developed for liposome-based drug delivery, for example, targeted delivery using PEGylation, can be transferred and applied to the protocells.

As discussed above, electrostatics and pore size can play a role in cargo loading. For example, porous silica nanoparticles can carry a negative charge and the pore size can be tunable from about 2 nm to about 10 nm or more. Negatively charged nanoparticles can have a natural tendency to adsorb positively charged molecules and positively charged nanoparticles can have a natural tendency to adsorb negatively charged molecules. In various embodiments, other properties such as surface wettability (e.g., hydrophobicity) can also affect loading cargo with different hydrophobicity.

In various embodiments, the cargo loading can be a synergistic lipid-assisted loading by tuning the lipid composition. For example, if the cargo component is a negatively charged molecule, the cargo loading into a negatively charged silica can be achieved by the lipid-assisted loading. In certain embodiments, for example, a negatively species can be loaded as cargo into the pores of a negatively charged silica particle when the lipid bilayer is fused onto the silica surface showing a fusion and synergistic loading mechanism. In this manner, fusion of a non-negatively charged (i.e., positively charged or neutral) lipid bilayer or liposome on a negatively charged mesoporous particle can serve to load the particle core with negatively charged cargo components. The negatively charged cargo components can be concentrated in the loaded protocell having a concentration exceed about 100 times as compared with the charged cargo components in a solution. In other embodiments, by varying the charge of the mesoporous particle and the lipid bilayer, positively charged cargo components can be readily loaded into protocells.

Once produced, the loaded protocells can have a cellular uptake for cargo delivery into a desirable site after administration. For example, the cargo-loaded protocells can be administered to a patient or subject and the protocell comprising a targeting peptide can bind to a target cell and be internalized or uptaken by the target cell, for example, a cancer cell in a subject or patient. Due to the internalization of the cargo-loaded protocells in the target cell, cargo components can then be delivered into the target cells. In certain embodiments the cargo is a small molecule, which can be delivered directly into the target cell for therapy. In other embodiments, negatively charged DNA or RNA (including shRNA or siRNA), especially including a DNA plasmid which may be formulated as histone-packaged supercoiled plasmid DNA, e.g., modified with a nuclear localization sequence, can be directly delivered or internalized by the targeted cells. Thus, the DNA or RNA can be loaded first into a protocell and then into then through the target cells through the internalization of the loaded protocells.

As discussed, the cargo loaded into and delivered by the protocell to targeted cells includes small molecules or drugs (especially anti-cancer and optionally, antiviral or other bioactive agents), bioactive macromolecules (bioactive polypeptides such as ricin toxin A-chain or diphtheria toxin A-chain or RNA molecules such as shRNA and/or shRNA as otherwise described herein) or histone-packaged supercoiled plasmid DNA which can express a therapeutic or diagnostic peptide or a therapeutic RNA molecule such as shRNA or siRNA, wherein the histone-packaged supercoiled plasmid DNA is optionally modified with a nuclear localization sequence which can localize and concentrate the delivered plasmid DNA into the nucleus of the target cell. As such, loaded protocells can deliver their cargo into targeted cells for therapy or diagnostics.

In various embodiments, the protocells and/or the loaded protocells can provide a targeted delivery methodology for selectively delivering the protocells or the cargo components to targeted cells (e.g., cancer cells). For example, a surface of the lipid bilayer can be modified by a targeting active species that corresponds to the targeted cell. The targeting active species may be a targeting peptide as otherwise described herein, a polypeptide including an antibody or antibody fragment, an aptamer, a carbohydrate or other moiety which binds to a targeted cell. In some aspects, the targeting active species is a targeting peptide as otherwise described herein. In certain embodiments, exemplary peptide targeting species include a MET binding peptide as otherwise described herein.

For example, by providing a targeting active species (e.g., a targeting peptide) on the surface of the loaded protocell, the protocell selectively binds to the targeted cell in accordance with the present teachings. In one embodiment, by conjugating an exemplary targeting peptide SP94 or analog or a MET binding peptide as otherwise described herein that targets cancer cells, including cancer liver cells to the lipid bilayer, a large number of the cargo-loaded protocells can be recognized and internalized by this specific cancer cells due to the specific targeting of the exemplary SP94 or MET binding peptide with the cancer (including liver) cells. In most instances, if the protocells are conjugated with the targeting peptide, the protocells will selectively bind to the cancer cells and no appreciable binding to the non-cancerous cells occurs.

Once bound and taken up by the target cells, the loaded protocells can release cargo components from the porous particle and transport the released cargo components into the target cell. For example, sealed within the protocell by the liposome fused bilayer on the porous particle core, the cargo components can be released from the pores of the lipid bilayer, transported across the protocell membrane of the lipid bilayer and delivered within the targeted cell. In embodiments, the release profile of cargo components in protocells can be more controllable as compared with when only using liposomes as known in the prior art. The cargo release can be determined by, for example, interactions between the porous core and the lipid bilayer and/or other parameters such as pH value of the system. For example, the release of cargo can be achieved through the lipid bilayer, through dissolution of the porous silica; while the release of the cargo from the protocells can be pH-dependent.

In certain embodiments, the pH value for cargo is often less than 7, or about 4.5 to about 6.0, but can be about pH 14 or less. Lower pHs tend to facilitate the release of the cargo components significantly more than compared with high pHs. Lower pHs tend to be advantageous because the endosomal compartments inside most cells are at low pHs, (about 5.5), but the rate of delivery of cargo at the cell can be influenced by the pH of the cargo. Depending upon the cargo and the pH at which the cargo is released from the protocell, the release of cargo can be relative short (a few hours to a day or so) or span for several days to about 20-30 days or longer. Thus, immediate release and/or sustained release applications from the protocells themselves are envisioned.

In certain embodiments, the inclusion of surfactants can be provided to rapidly rupture the lipid bilayer, transporting the cargo components across the lipid bilayer of the protocell as well as the targeted cell. In certain embodiments, the phospholipid bilayer of the protocells can be ruptured by the application/release of a surfactant such as sodium dodecyl sulfate (SDS), among others to facilitate a rapid release of cargo from the protocell into the targeted cell. Other than surfactants, other materials can be included to rapidly rupture the bilayer. One example would be gold or magnetic nanoparticles that could use light or heat to generate heat thereby rupturing the bilayer. Additionally, the bilayer can be tuned to rupture in the presence of discrete biophysical phenomena, such as during inflammation in response to increased reactive oxygen species production. In certain embodiments, the rupture of the lipid bilayer can in turn induce immediate and complete release of the cargo components from the pores of the particle core of the protocells. In this manner, the protocell platform can provide an increasingly versatile delivery system as compared with other delivery systems in the art. For example, when compared to delivery systems using nanoparticles only, the disclosed protocell platform can provide a simple system and can take advantage of the low toxicity and immunogenicity of liposomes or lipid bilayers along with their ability to be PEGylated or to be conjugated to extend circulation time and effect targeting. In another example, when compared to delivery systems using liposome only, the protocell platform can provide a more stable system and can take advantage of the mesoporous core to control the loading and/or release profile and provide increased cargo capacity.

In addition, the lipid bilayer and its fusion on porous particle core can be fine-tuned to control the loading, release, and targeting profiles and can further comprise fusogenic peptides and related peptides to facilitate delivery of the protocells for greater therapeutic and/or diagnostic effect. Further, the lipid bilayer of the protocells can provide a fluidic interface for ligand display and multivalent targeting, which allows specific targeting with relatively low surface ligand density due to the capability of ligand reorganization on the fluidic lipid interface. Furthermore, the disclosed protocells can readily enter targeted cells while empty liposomes without the support of porous particles cannot be internalized by the cells.

Pharmaceutical Compositions and Formulations

Pharmaceutical compositions comprise an effective population of protocells as otherwise described herein formulated to effect an intended result (e.g. therapeutic result and/or diagnostic analysis, including the monitoring of therapy) formulated in combination with a pharmaceutically acceptable carrier, additive or excipient. The protocells within the population of the composition may be the same or different depending upon the desired result to be obtained. Pharmaceutical compositions may also comprise an addition bioactive agent or drug, such as an anticancer agent or an antiviral agent, for example, an anti-HIV, anti-HBV or an anti-HCV agent.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, intrathecal or intramuscular injection, among others, including buccal, rectal and transdermal administration. Subjects contemplated for treatment include humans, companion animals, laboratory animals, and the like. Also contemplated is the immediate and/or sustained/controlled release compositions, including compositions which comprise both immediate and sustained release formulations. This is particularly true when different populations of protocells are used in the pharmaceutical compositions or when additional bioactive agent(s) are used in combination with one or more populations of protocells as otherwise described herein.

Formulations containing compounds may take the form of liquid, solid, semi-solid or lyophilized powder forms, such as, for example, solutions, suspensions, emulsions, sustained-release formulations, tablets, capsules, powders, suppositories, creams, ointments, lotions, aerosols, patches or the like, e.g., in unit dosage forms suitable for simple administration of precise dosages.

Pharmaceutical compositions typically include a conventional pharmaceutical carrier or excipient and may additionally include other medicinal agents, carriers, adjuvants, additives and the like. In one embodiment, the composition is about 0.1% to about 85%, about 0.5% to about 75% by weight of a compound or compounds, with the remainder consisting essentially of suitable pharmaceutical excipients.

An injectable composition for parenteral administration (e.g. intravenous, intramuscular or intrathecal) will typically contain the compound in a suitable i.v. solution, such as sterile physiological salt solution. The composition may also be formulated as a suspension in an aqueous emulsion.

Liquid compositions can be prepared by dissolving or dispersing the population of protocells (about 0.5% to about 20% by weight or more), and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline.

For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

Methods for preparing such dosage forms are known or is apparent to those skilled in the art; for example, see Remington's Pharmaceutical Sciences (17th Ed., Mack Pub. Co., 1985). The composition to be administered will contain a quantity of the selected compound in a pharmaceutically effective amount for therapeutic use in a biological system, including a patient or subject.

Methods of treating patients or subjects in need for a particular disease state or infection (especially including cancer and/or a HBV, HCV or HIV infection) comprise administration an effective amount of a pharmaceutical composition comprising therapeutic protocells and optionally at least one additional bioactive (e.g. antiviral) agent.

Diagnostic methods comprise administering to a patient in need (a patient suspected of having cancer) an effective amount of a population of diagnostic protocells (e.g., protocells which comprise a target species, such as a targeting peptide which binds selectively to cancer cells and a reporter component to indicate the binding of the protocells to cancer cells if the cancer cells are present) whereupon the binding of protocells to cancer cells as evidenced by the reporter component (moiety) will enable a diagnosis of the existence of cancer in the patient.

An alternative of the diagnostic method can be used to monitor the therapy of cancer or other disease state in a patient, the method comprising administering an effective population of diagnostic protocells (e.g., protocells which comprise a target species, such as a targeting peptide which binds selectively to cancer cells or other target cells and a reporter component to indicate the binding of the protocells to cancer cells if the cancer cells are present) to a patient or subject prior to treatment, determining the level of binding of diagnostic protocells to target cells in said patient and during and/or after therapy, determining the level of binding of diagnostic protocells to target cells in said patient, whereupon the difference in binding before the start of therapy in the patient and during and/or after therapy will evidence the effectiveness of therapy in the patient, including whether the patient has completed therapy or whether the disease state has been inhibited or eliminated (including remission of a cancer).

The following non-limiting examples are illustrative, and are not to be taken as limiting the disclosure or claims in any way. In the examples, as well as elsewhere in this application, all parts and percentages are by weight unless otherwise indicated.

Example 1

Exemplary Synthesis
MSNP Synthesis

Prismatic hexagonal structured MSNP are synthesized using techniques described in the literature (see Lin, Y.-S.; Haynes, C. L. Impacts of Mesoporous Silica Nanoparticle Size, Pore Ordering, and Pore Integrity on Hemolytic Activity. Journal of the American Chemical Society 2010, 132, 4834-4842 and Lin, Y.-S.; Abadeer, N.; Hurley, K. R.; Haynes, C. L. Ultrastable, Redispersible, Small, and Highly Organomodified Mesoporous Silica Nanotherapeutics. Journal of the American Chemical Society 2011, 133, 20444-20457.).

Pore Size

To make large pore spherical MSNPs, one follows the synthesis procedure described in the literature (see, Wang, J.; Sugawara-Narutaki, A.; Shimojima, A.; Okubo, T. Biphasic synthesis of colloidal mesoporous silica nanoparticles using primary amine catalysts. Journal of Colloid and Interface Science 2012, 385, 41-47 and Shen, D.; Yang, J.; Li, X.; Zhou, L.; Zhang, R.; Li, W.; Chen, L.; Wang, R.; Zhang, F.; Zhao, D. Biphase Stratification Approach to Three-Dimensional Dendritic Biodegradable Mesoporous Silica Nanospheres. Nano Letters 2014, 14, 923-932)(Moeller, Karin, et al. "Highly Efficient siRNA Delivery from Core-Shell Mesoporous Si lica Nanoparticles with Multifunctional Polymer Caps."*Nanoscale* (2015).). Purification process was the same as described by Yu-Shen's papers. (Lin, Y,-S.; Abadeer, N.; Hurley, K. R.; Haynes, C. L. Ultrastable, Redispersible, Small, and Highly Organomodified Mesoporous Silica Nanotherapeutics. *Journal of the American Chemical Society* 2011, 133, 20444-20457.)

Carboxylation of MSNP Surface—For Conjugation of Bisphosphonates and Other Moieties The MSNP after formation (about a 12 hour synthesis using standard methods of preparation, as described above) may be first carboxylated (using a silyl carboxyl agent such as 3-(triethoxysilyl)propylsuccinic anhydride at approximately 0.5% to about 20%, often about 1% to about 15%, often about 1% to about 5%, about 1-1.5% of the TEOS utilized) to form a carboxylic acid group on the surface of the MSN linked to the MSN through Si—O—Si bonds formed when the 3-(triethoxysilyl)propylsuccinic acid and the SiOH groups on the surface of the MSN react. This takes about an hour or so. The carboxylated MSN is then subjected to a hydrothermal step (generally about 12-36 hours, such as about 24 hours at an elevated temperature ranging from about 60° C. to about 120° C.) to form a final carboxylated MSN which can be reacted with a crosslinker such as EDC or other crosslinker (the amine portion of the crosslinker forms an amide or other stable bond with the carboxyl group) and the carboxylic/electrophilic end of the linker is reacted with an amine containing phospholipid such as DOPE, DMPE, DPPE or DSPE to form the hydrocarbon coated MSN.

Conjugation of Carboxylic Group with Bisphosphonate through Crosslinker

After carboxylation, the carboxylic acid modified MSNPs can be conjugated to the primary amine on the bisphosphonate molecule to form an amide bond. This is straight forward chemistry. For example, heterobifunctional carboxyl-to-amine crosslinker 1-ethyl-3-(3 dimethylaminopropyl)carbodiimide hydrochloride (EDC) or dicyclohexylcarbodiimide (DCC), among others, depending on the functional group chemistry, can be added to the bisphosphonate molecule, or to the COOH-modified MSNPs, or all three components can be added together simultaneously. In general, the bisphosphonate to crosslinker mole ratio may be approximately 2:1, although this ratio may be increased) and mass ratio of bisphosphonate to MSNP is approximately 1:2. This should provide a complete covering of the MSNP (at least about 75%, at least about 80%, at least about 85%, at least about 90%, at least about 95%, at least about 98-99% and up to about 100% of the surface area of the MSNP. In one embodiment, the MSNP is covered as completely as possible. Pursuant to this conjugation process, crosslinker reaction time 30 min to 4 hours at room temperature, or 8-16 hours at 4° C. After reaction, MSNPs are washed twice in $H_2O$ and stored in $H_2O$.

Conjugation of Bisphosphonate to MSNP Surface Using Click Chemistry

Click chemistry—Copper free click chemistry modified MSNPs using either Azide (N3) modified or dibenzocyclooctyne (DBCO) modified MSNP cores. Standard azide/acetylenic group formation of triazole through reaction of azide with acetylenic group on carbon-carbon triple bond moiety.

Click modified silane—DBCO-NHS ester or N3-NHS ester is reacted with (3-Aminopropyl)triethoxysilane (APTES) (or other aminated silane, for example, as described herein) in dimethylformamide (DMF), dimethylsulfoxide (DMSO) or other polar solvent for 30 to 60 minutes at room temperature. NHS-ester to amine reaction forms an amide bond. In synthesis scheme 1 (hex MSNP, see above) click modified silane is added at the same time as TEOS and synthesized and purified using standard method described in the literature. This forms an NHS-ester on the surface of the MSNP which can be subsequently conjugated to the bisphosphonate.

In synthesis scheme 2 (large pore MSNP, see above) click modified silane is added to the aqueous phase 10 minutes prior to TEOS addition in the organic phase and particles are synthesized and purified as described in the literature.

Bisphosphonate molecule modification is performed using the same technique described above DBCO- or N3-NHS ester to synhesize DBCO- or a N3-Bisphosphonate molecule. To prepare bisphosphonate modified MSNPs, N3-Bisphosphonate molecules are reacted with DBCO-MSNPs or DBCO-Bisphosphonate molecules are reacted with N3-MSNPs in $H_2O$ for 2 hours to 24 hours at room temperature. The reaction product obtained is then washed several times in $H_2O$ to remove unreacted bisphosphonate molecules.

Conjugation of Bisphosphonate to MSNP Surface Using Isocyanate Chemistry

Bisphosphonate modified silanes may be prepared using 3-(Triethoxysilyl)propyl isocyanate reacted with bisophosphonate in DMF or DMSO for 30 minutes to 2 hours at room temperature. In synthesis scheme 1 (hex MSNP, see above) bisphosphonate-silane is added at the same time as TEOS and synthesized and purified using standard methods which are described in the literature. In synthesis scheme 2 (large pore MSNP) bisphosphonate silane is added to the aqueous phase 10 minutes prior or TEOS addition in the organic phase and particles are synthesized and purified as described in the literature.

Results

MSNPs were loaded with various cargo types, such as chemotherapy drugs (Docetaxel, Cisplatin), biologics (anti-EGFR peptides), DOTA for chelation of Gallium-68, and siRNA. MSNPs offer greater therapeutic potential and human compatibility for multi-functional drug delivery over other nanoparticle types because of three main properties: increased cargo capacity, well established chemistries for silica modification, and superior stability during modification and loading of MSNPs. These qualities result in MSNPs exhibiting the highest payload to nanoparticle mass ratio known (about 3-6% as opposed to about 0.2% in liposomes), and excellent in vivo stability. MSNPs are comprised of a highly rigid pore structure that results in a very large surface for adsorption and entrapment of payload (about 1.0 $m^2$/mg of MSNP) for slow controlled release of payload in vivo. Due to its ubiquitous use for electronics fabrication, silica modification chemistry is well understood, enabling reproducible conjugation of targeting moieties and chelation agents such as DOTA to MSNPs in a straightforward manner. Silicon dioxide is non-toxic in vitro or in vivo and due to its silica-based composition, it is highly stable after several modifications to MSNPs, resulting in high yields of complex, multifunctional nanoparticles. Certain surface chemistries can minimize MSNP uptake by endothelial cells, leukocytes, and binding to serum proteins. This is an important advance because a higher proportion of osteotropic MSNPs will remain in the circulation, enhancing bone targeting. When compared to polymer-based nanoparticle formulations, MSNPs exhibit minimal polydispersity, which is important for minimizing non-specific uptake by immune cells.

Figure 2:
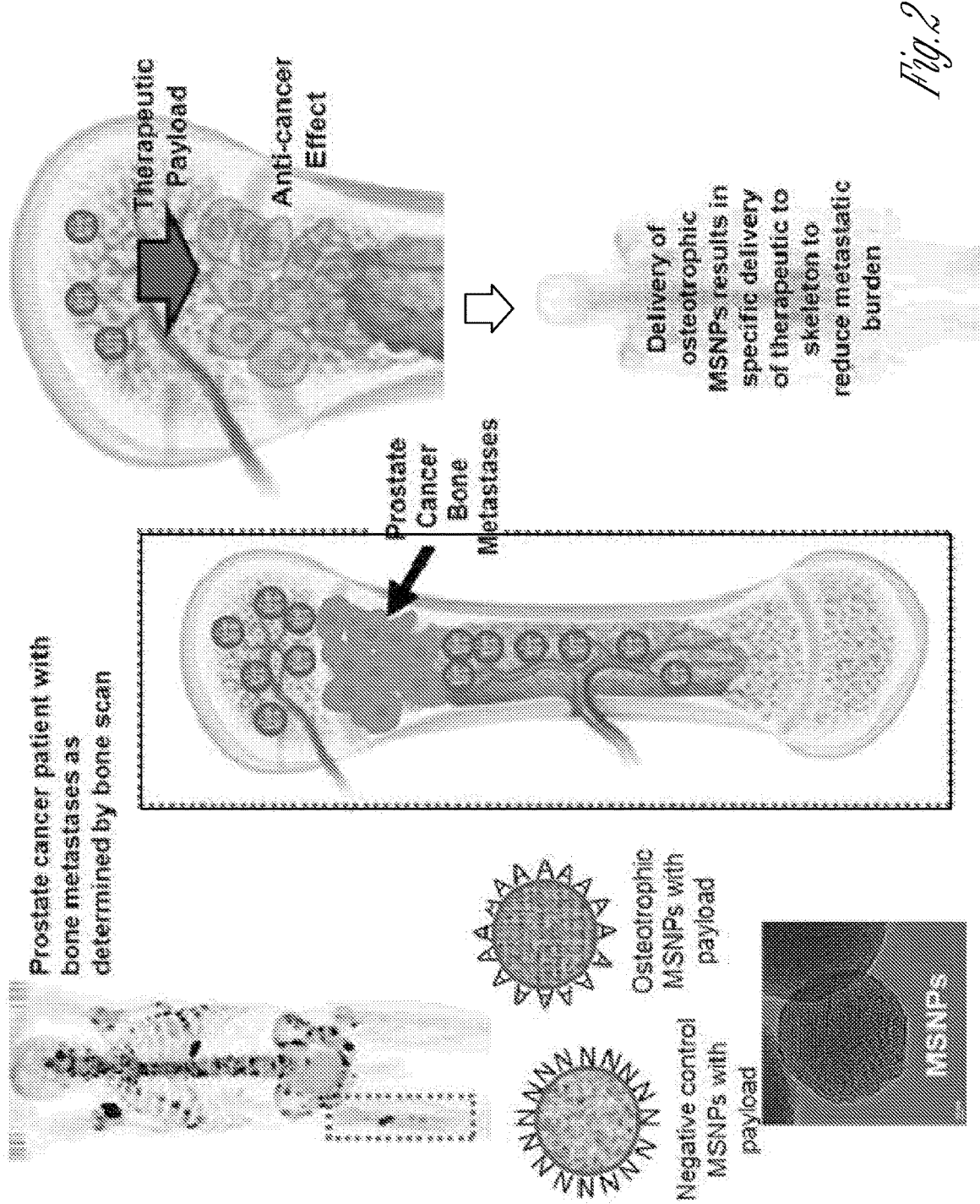
FIG. 2. Mechanism of action for osteotrophic mesoporous silica Nanoparticles (MSNPs). Osteotrophic MSNPs when intravenously injected will preferentially accumulate within the osteoblastic regions of bone marrow where metastatic prostate cancers reside. After deposition to bone, osteotrophic MSNPs will release their therapeutic payload in a slow controlled manner. Payload will induce an anti-cancer effect while minimizing drug levels in the systemic circulation.
Figure 5A:
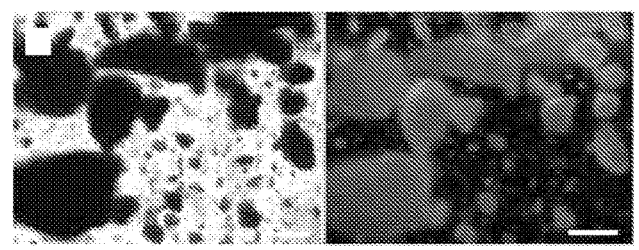
FIGS. 5A-F. Binding affinity of Fluorescently Labelled Alendronate to hydroxyapatite and mouse bone sections. A) Brightfield (left) and fluorescent (right) images of Alendronate-FITC bound to hydroxyapatite particles. Scale bar is 0.2 mm. B) Brightfield (left) and fluorescent images of NOTdronate-FITC bound to hydroxyapatite particles. Scale bar is 0.2 mm. C) Half of mouse long bone sections stained with NOTdronate-FITC. Scale bar is 0.2 mm. D) Half of mouse long bone sections stained with Alendronate-FITC. Scale bar is 0.2 mm. E) Mouse bone sections were stained with Alendronate-FITC and NOTdronate-FITC. Scale bar is 250 μm. F) Mouse bone sections were stained with AlendronateCy5 and NOTdronate-Cy5. Scale bar is 250 μm.
Figure 5B:
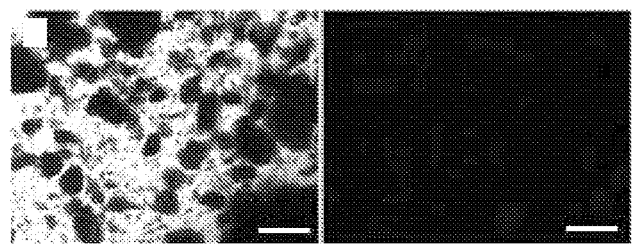
Figure 5C:
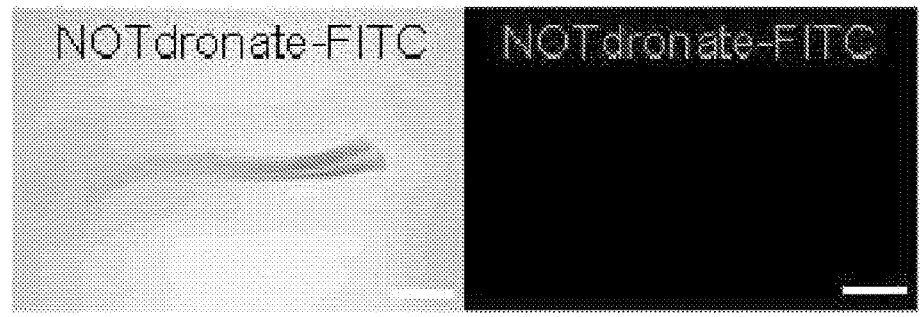
Figure 5D:
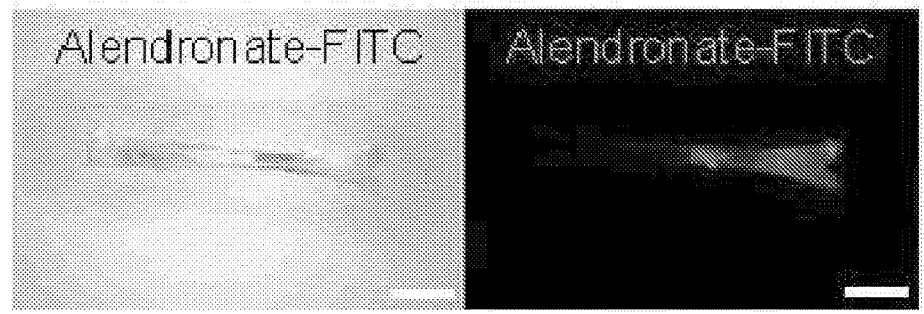
Figure 5E:
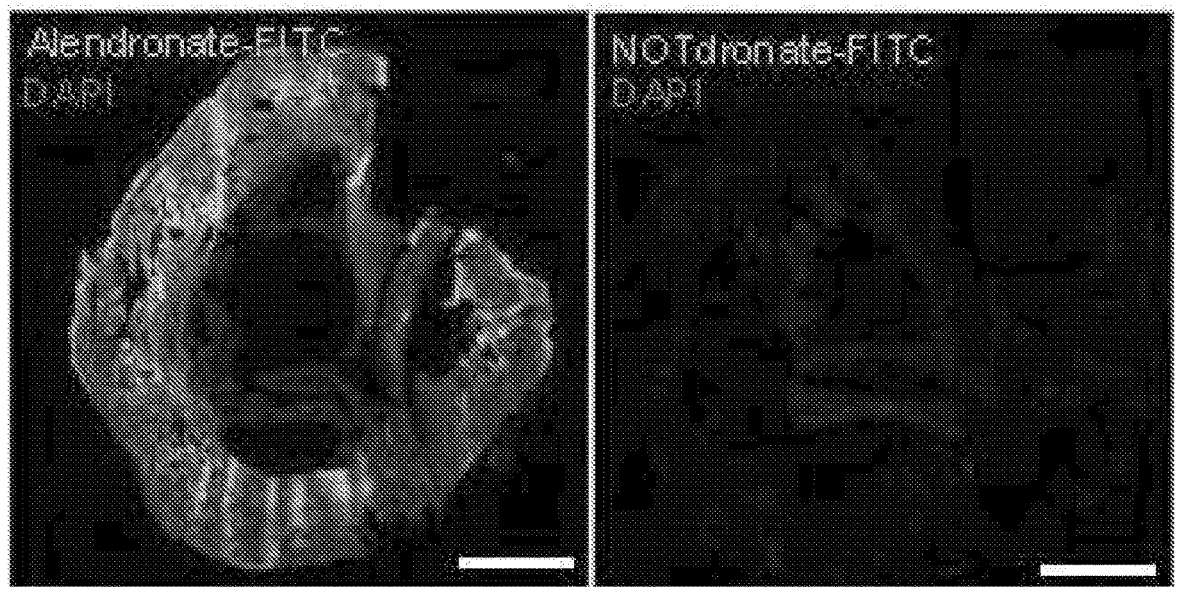
Figure 5F:
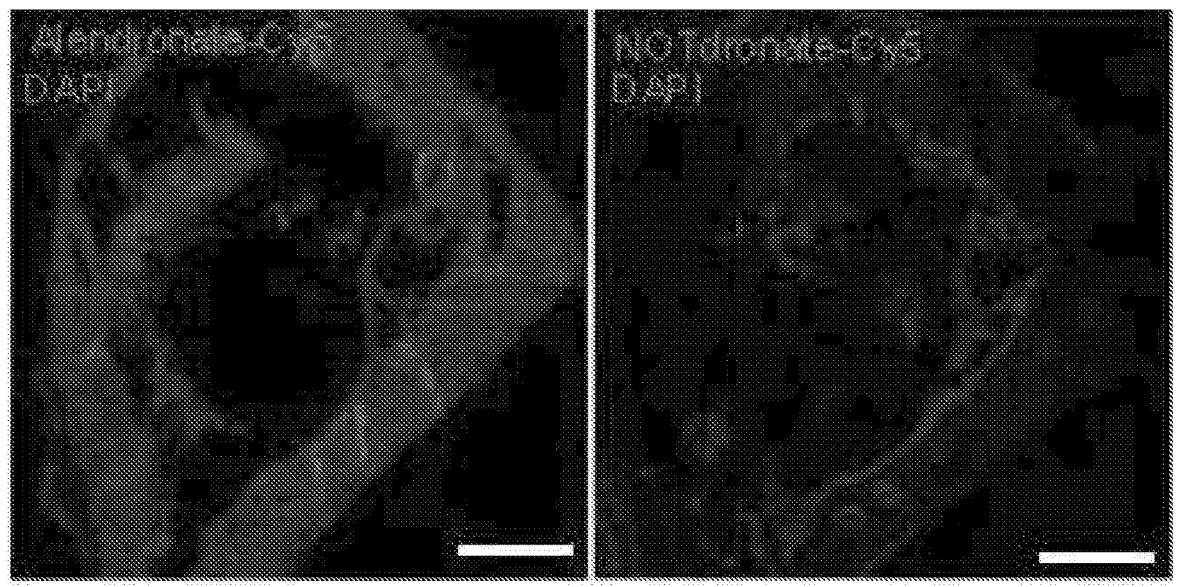
Figure 6C:
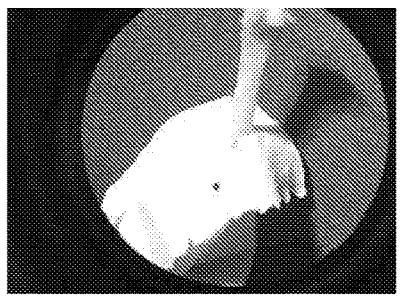
FIGS. 6A-F. A-C) images of bone. A) Negative control. B) P2-A treatment. C) P2-C treatment. D-E) Fluorescent images of bone, D) Negative control. E) P2-A treatment. F) P2-C treatment.
Figure 6F:
Figure 6B:
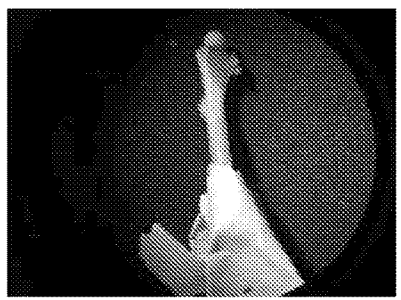
Figure 6E:
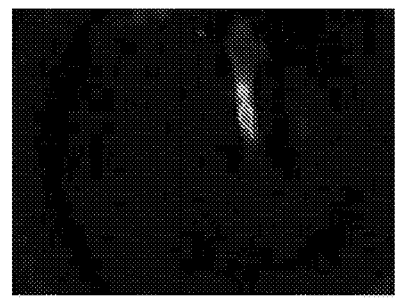
Figure 6A:
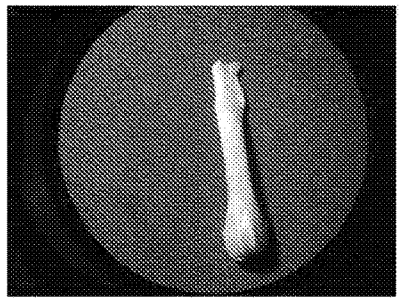
Figure 6D:
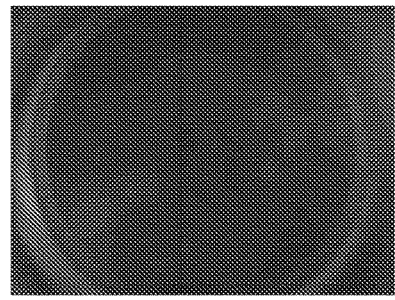
Figure 8A:
FIGS. 8A-B. Deposition of Osteotrophic Mesoporous Nanoparticles (MSNPs) to Osseous Sites. A) Increased deposition of Alendronate-MSNPs (red) in the osseous space of a mouse long bone (blue). B) Minimal deposition of NOTdronate-MSNPs (red) in the osseous space of a mouse long bone (blue).
Figure 8B:
Figure 9A:
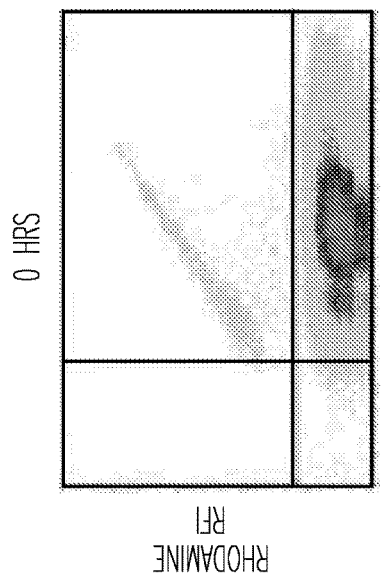
FIGS. 9A-D. Plasma degradation effects on rhodamine-labeled MSNPs over time. Rhodamine-labeled MSNPs were incubated in healthy volunteer plasma at various time points and then nanoscale flow cytometry (A-C) was performed on plasma to enumerate the concentration of MSNPs (D). There was no decrease in MSNPs and they accumulated plasma proteins on their surface, increasing their size.
Figure 9B:
Figure 9C:
Figure 9D:
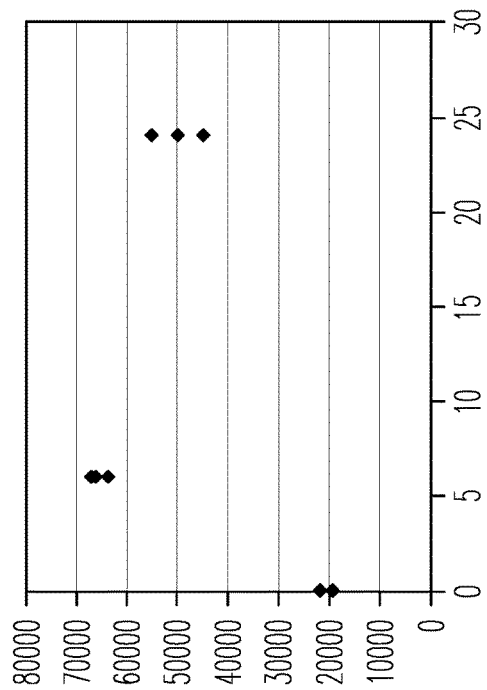
Figure 10A:
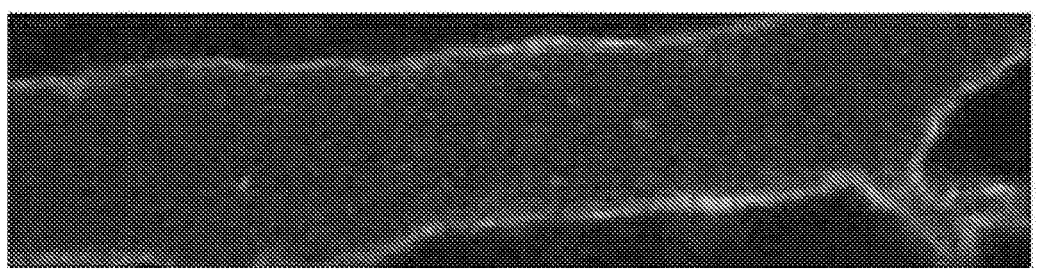
FIGS. 10A-D. Intravital imaging of circulating MSNPs in the chorioallantoic membrane of the avian embryo. Injection of MSNPS (D, red signal), Hoechst (B, blue signal), and lectin (C, green signal) permits the visualization of MSNP microcirculation within the CAM capillary bed (A).
Figure 10B:
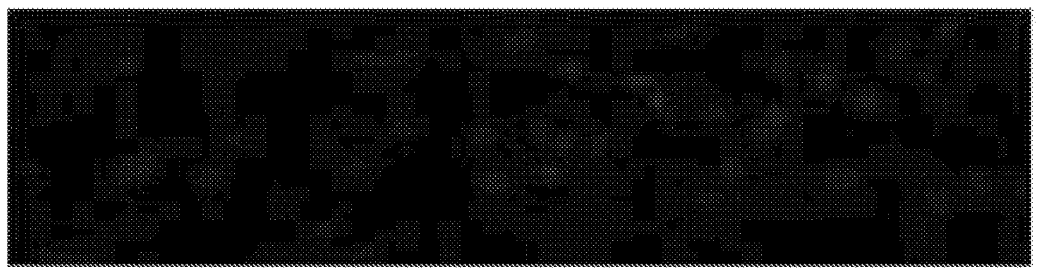
Figure 10C:
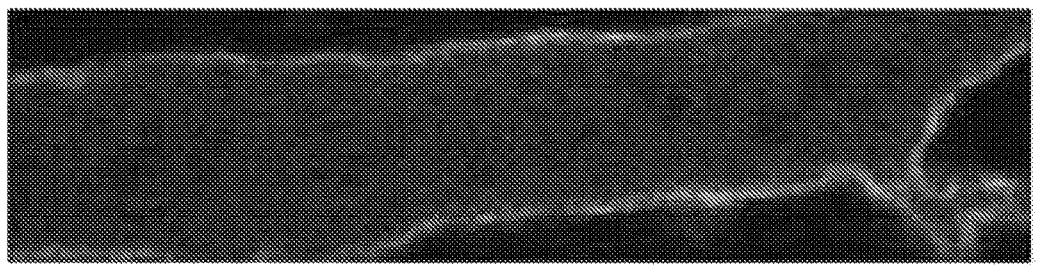
Figure 10D:
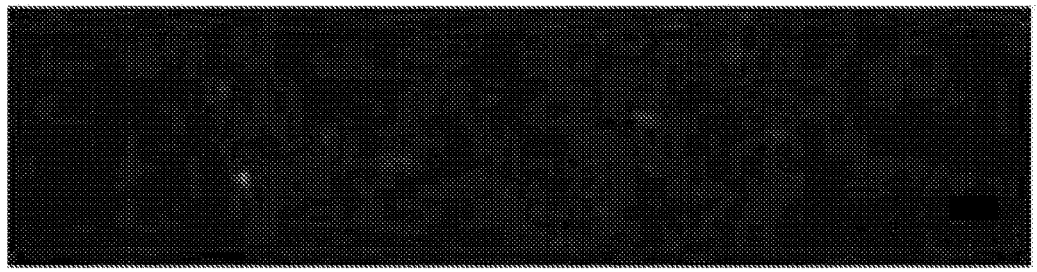

To construct osteotropic MSNPs, the surface of these nanoparticles is decorated with Alendronate, a bisphosphonate molecule that has high affinity for hydroxyapatite, the mineralized component of bone. Several types of bisphosphonates are available for use in alleviating bone pain caused by prostate cancer bone metastases, and therefore utilizing Alendronate as a targeting moiety on MSNPs may impart an anti-osteoblastic therapeutic benefit at sites of prostate cancer bone metastases. Various fluorescent conjugates to Alendronate (FIG. 3A) and a negative binding control, called NOTdronate (US Patent Pending PCT/CA2014/050312), which is unable to bind to calcium or hydroxyapatite (FIG. 3B), were developed. Alendronate conjugates to Fluorescein Isothiocyanate (FITC) or Cyanine5 (Cy5) bind to synthetic hydroxyapatite nanoparticles with high affinity (FIG. 4A) whereas the NOTdronate fluorescent conjugates do not (FIG. 4B). Similar results are observed in sections of mouse bones (FIG. 5) and with mouse long bones when stained ex vivo (FIG. 6), demonstrating the specificity of Alendronate-FITC/Cy5 probe to the hydroxyapatite component of bone. Most importantly, decoration of MSNPs with Alendronate confers high specificity of the modified MSNPs to mouse bone ex vivo (FIG. 6). Finally, when intravenously injected via the tail vein of mice, NOTdronate-coated MSNPs are unable to bind to any bone and are primarily present within the liver, lung and kidney, whereas Alendronate-coated MSNPs are abundant in the hones analyzed by histology (FIG. 8), indicating these MSNPs are osteotropic for bone marrow specific release of cargo (FIG. 2).

Osteotropic MSNPs efficiently target all bone in preclinical models of prostate cancer and then release therapeutic payload in a slow release, controlled manner into the bone microenvironment. This route of delivery will result in maximal bioavailable levels of MSNPs and their cargo in the bone and minimize nontarget exposure, thus minimizing side effects.

Methodology

Example A

A number of MSNPs are used. These include: Vacant Osteotropic MSNPs, Loaded Osteotropic MSNPs with docetaxel or siRNA, vacant non-Osteotropic MSNPs, and loaded non-Osteotropic MSNPs. All MSNPs are conjugated with DOTA-Ga68/Gd, a radioactive tracer for PET/MRJ imaging and are also conjugated with a Cy5 fluorescent dye to permit in vivo whole body imaging and histological analyses. The use of both Ga68 ($^{68}$Gallium) and Gd (gadolinium) will enable us to perform highly-sensitive PET imaging for the first 2 hours of injection and MRI imaging for the remainder of any time course experiment, siRNA-containing MSNPs will be synthesized and packaged. All MSNPs are maximally loaded with payload, with the expectation that 3-6% of MSNP mass will be Docetaxel/siRNA.

To determine the half-life and payload release kinetics of MSNPs, ex vivo plasma based experiments are performed to evaluate the half-life of the MSNPs listed above. Preliminary half-life experiments (See FIGS. 7 and 9) on the MSNPs revealed a plasma half-life of approximately 2 days measured using nanoscale flow cytometry. To assess both the degradation and payload release kinetics, the same kinds of experiments were conducted in plasma. At least 5 time points are taken over, at least, 7 days of incubation in plasma. At each time point, MSNPs are centrifuged to form a pellet such that the plasma supernatant can be used for assessing payload release kinetics. The amount of drug present in this plasma supernatant and remaining in the MSNPs (pellet) is quantified by UHPLC-MS analysis for Docetaxel, and by digital PCR (Leong laboratory) for siRNA. This data is used in for developing the MSNP PBPK model as well as the payload.

PBPK Model.

To determine the dose at which bone accumulation of MSNPs is maximal and exposure in non-target tissues is at a "no observed adverse effect level" (NOAEL), C57BL/6J and immuno-compromised SCID mice are used as preclinical models. The two mouse models assess the pharmacokinetics of the MSNPs in the presence (C57BL/6J) and absence (NOD-SCID) of an adaptive immune response. Differential pharmacokinetics aids in the parameterization of MSNP degradation by the RES system and aids in extrapolation to humans. The mice models are used to assess the systemic and tissue distribution kinetics of the MSNPs as well as toxicity. A dose escalation study is performed to determine relative bone uptake as a function of dose. MSNPs are injected into the tail vein using at least 5 different doses plus appropriate saline control (N=25/dose; 6 doses; n=150 mice of each species; n=300 mice total). At each time point of T=15 min, 1 hr, 6 hrs, 24 hrs, 7 days, 5 mice from each dose undergo non-invasive imaging (MRI, PET-CT animal imaging units, GE HealthCare, Lee Laboratory) to determine MSNP kinetics in bone, liver, lung, spleen and brain (Lee laboratory). Whole body in vivo fluorescence imaging is also performed. These experiments allow for an assessment of differential organ accumulation kinetics and aid in PBPK model parametrization. Based on half-life assessment, it is expected that radioactivity and Cy5 fluorescence in bone at early time points represents intact MSNP bone deposition whereas the 7 day time point signal may result from degradation products and requires careful interpretation. This example produces non-invasive imaging for all nanoparticle types and collection of tissue.

Figure 7:
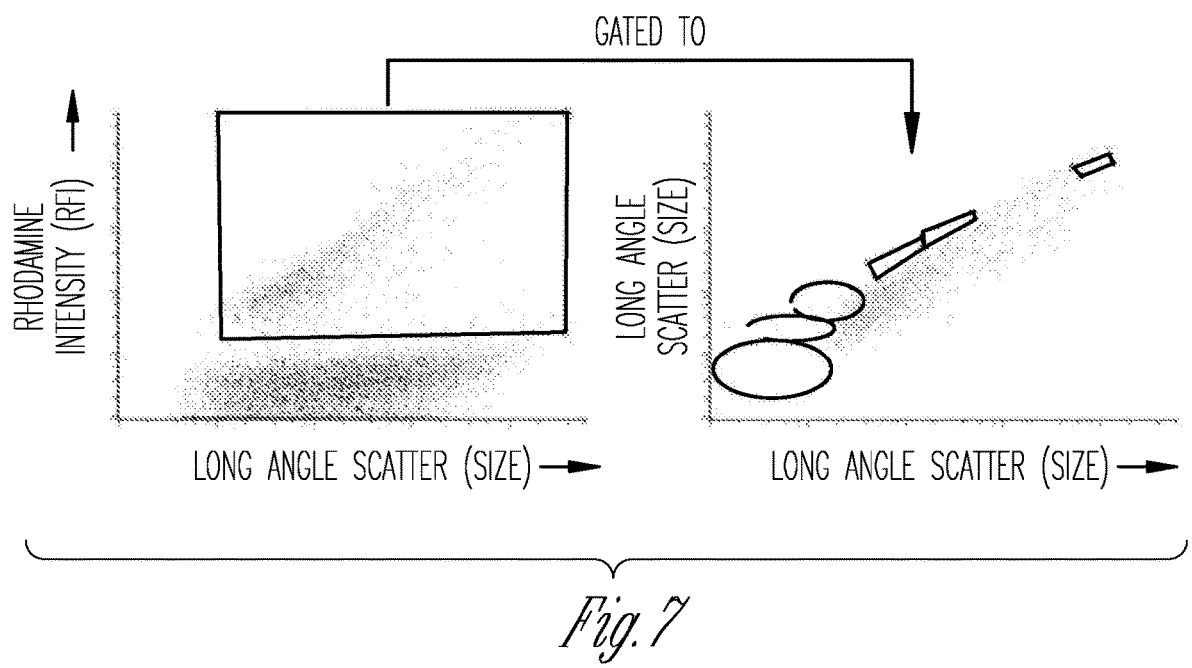
FIG. 7. Detection of Rhodamine-labelled kilesoporous Silica Nanoparticles (MSNPs) in Mouse Blood T=6 hrs Post-Injection. Using nanoscale flow cytometry, Rhodamine labelled MSNPs can be readily enumerated in plasma collected from mice injected with MSNPs. A subpopulation of Rhodamine-positive events are present in plasma (left panel, red gate), which exhibit a size range of 100-250 nm (right panel).

Each mouse at the final time point undergoes cardiac puncture to isolate 0.5 mL of whole blood for systemic kinetic analysis (% blood cell uptake of MSNPs) using conventional flow cytometry. Mice are sacrificed and urine, lung, spleen, brain and liver, kidney, bone and skeletal muscle (as a representative tissue with a continuous vascular endothelium) are isolated. To quantify organ specific accumulation of MSNPs, a sample of tissue with known weight is dried and submitted to radioactive scintillation assessment (Leong Jab). This provides quantifiable tissue kinetics for parameterization of the PBPK model. To confirm results from radioactivity experiments and to assess intra-tissue distribution (endothelial vs. stroma uptake), tissues are processed and stained with endothelial-specific antibodies (anti-CD3 I-Alexa488) and phalloidin-Alexa594 or anti-myosin-Alexa594 to stain tissue or skeletal muscle. To do this, paraffin tissue blocks for each organ are serially sectioned such that every 50th section of the entire organ is analyzed and at least 50 randomly selected regions of interest will be, stained, imaged and analyzed. This imaging provides insight regarding stability of MSNPs that may not have been clear from studies using radioactive material, especially at 7 days. Payload kinetics will be determined in whole blood and each individual tissue through UHPLC-MS analysis for Docetaxel and digital PCR for siRNA. The use of two mice strains differing in immune function will allow for a quantitative assessment, using flow cytometry, of the extent of immune cell phagocytosis and its contribution to MSNP loss systemically. It is also expected that tissue distribution kinetics may be affected by the lack of immune cells, especially in spleen. The tissue kinetics, e.g. dose-exposure relationship, are those of C57BL/6J mice. Urine is analyzed by nanoscale flow cytometry (FIG. 7). Considering the size of the MSNPs, their presence in urine would be indicative of kidney damage. To determine if the osteotropic MSNPs are cytotoxic, a TUNEL stain (FITC) is performed on additional sections to determine the percentage of apoptotic cells that have MSNPs (Cy5 co-localization with FITC). These images are compared with the control mice. The NOAEL of loaded and vacant osteotropic MSNPs will be calculated. This allows for the determination of the toxicity of the MSNPs alone as well as with the addition of payload which is expected to produce higher toxicity. These studies provide valuable information on organ/tissue accumulation, systemic circulation kinetics and elimination potential that will inform the development of a mechanistic PBPK model. These experiments also provide the dose of MSNPs maximally accumulated in bone (dose of saturation) with the least nontarget exposure/toxicity.

Results: Based on preliminary data, there will be insubstantial (and likely no) deposition of negative control MSNPs in the bone, but even if deposition occurs, it is likely that the kinetics will not be significantly different from the osteotropic MSNPs. The experiments using radioactivity do not distinguish between intact and degraded MSNPs. However, the half-life is approximately 2 days and most time points are prior to one half-life suggesting that the majority of radioactivity will be intact MSNP. Histology focusing on the Cy5 fluorescence will also improve result interpretation.

Example B

Two mouse models of PCa bone metastasis are used: 1) NOD-SCID mice that receive an injection of PC-3M-LN4-tdTomato metastatic PCa cells (5,000 cells in 0.1 mL injection volume into right and left tibia of a 3 week old mouse, use at 7 weeks) and 2) NOD-SCID mice that also receive intratibial injections of LnCAP-tdTomato metastatic PCa cells (similar concentration and injection sites into 3 week old mice). To confirm the presence of bone metastases in all animals prior to experimentation, bone scans after injection of technetium-99m are performed and are visualized using the FX-Pro whole body in vivo imager (Carestream Health Inc.) which is capable of radiographic scans (Lee lab). A confirmed model has between 4-15 bone metastases in both tibias.

Example C

To demonstrate loaded osteotropic MSNP bone deposition following injection in a disease model, intratibial PCa mouse models (N=15/treatment) undergo one of four treatments: A) loaded Osteoptrophic MSNPs—Docetaxel or siRNA (MSNP dose from Example A administered twice per week), B) loaded non-Osteotropic MSNPs—Docetaxel or siRNA (MSNP dose as determined above), C) free circulating Docetaxel (20 mg/kg, 6 cycles over 28 days) or siRNA (200 pmol/injection, 10 cycles over 20 days (25)), and D) vehicle control (saline twice per week). Pairs of mice are housed in a barrier mediated facility at the vivarium at St. Joseph's Hospital. All injections are subcutaneous in the flank region. Tail tipping is done weekly to monitor the following: i) PSA serum levels, performed by the core laboratories by the Hospital (ELISA)—a standard blood based clinical follow-up tool. PSA is released by LnCAP not PC-3M-LN4 cells, so the expectation is that PSA levels will be minimal in the latter. ii) Blood for flow cytometry to enumerate erythrocyte and platelet counts to determine if the treatments used cause myelosuppression of the bone marrow; iii) blood for nanoscale flow cytometry to enumerate circulating MSNPs, UHPLC-MS for Docetaxel levels and digital PCR for siRNA. At the end of the treatment cycle (Docetaxel=28 days, siRNA=21 days), bone scans (Tc98-biphosphonate) are performed to determine metastatic load and then animals will be sacrificed and all long shaft bones are extracted for histological assessment as in Objective #1. Histological analysis also relies on tdTomato signal, human mitochondria and human Ki-67 immunostains to quantitate metastatic load in the bones. This provides determination of differential tumor burden between treatments.

Demonstration of Therapeutic Efficacy of Loaded Osteotropic MSNPs Compared to Nontargeted Traditional Therapy The intratibial PCa mouse models (N=I5/treatment) undergo one of four treatments over 28 days: E) loaded Osteoptrophic MSNPs Docetaxel and siRNA (MSNP dose from Example A administered 4× per week, different payloads on alternating days), F) loaded non-Osteotropic MSNPs—Docetaxel and siRNA (both MSNP doses from Example A administered 4× per week, different payloads on alternating days), G) free circulating Docetaxel (20 mg/kg, 6 cycles over 4 weeks) and siRNA (200 pmol/injection, 10 cycles over 20 days (25)), and H) vehicle control (saline 4× per week).

Applicants hypothesize a synergistic impact when using osteotropic MSNPs compared to single payload delivery via osteotropic MSNPs and when compared to circulating Docetaxel and siRNA combination therapy. Although the MSNP dosing schedule is doubled in this Aim, injections are done on different days as opposed to injection of both different kinds of payloads on the same day.

Results

PET/MRI imaging is not required. However, PET imaging at early time points (within 2 hours of injection) and MRI imaging (after 2 days of injection) may be performed in a fraction of animals to ensure bone-specificity for all batches of animal experiments. It is expected that osteotropic MSNPs loaded with Docetaxel/siRNA will rapidly home to the bone metastases post-injection. Furthermore, we anticipate significantly lower metastatic burden with loaded osteotropic MSNPs compared to controls in all mouse models. As a negative control, mice with PC-3M-LN4 bone metastases will respond poorly to siRNA to AR because these are cells that lack AR expression. Most importantly, since the total amount of drug used via osteotropic MSNPs is lower than circulating Docetaxel/siRNA, equivalent therapeutic efficacy is likely on bone metastatic burden. Osteotrophic MSNPs that have a mix of both Docetaxel and siRNA specific for AR mRNA are co-injected. When compared to MSNP formulations with the homogenous payload (Docetaxel or siRNA), this will inform our group of the therapeutic efficacy of combination payloads in our preclinical models of advanced prostate cancer.

Example D

Figure 11:
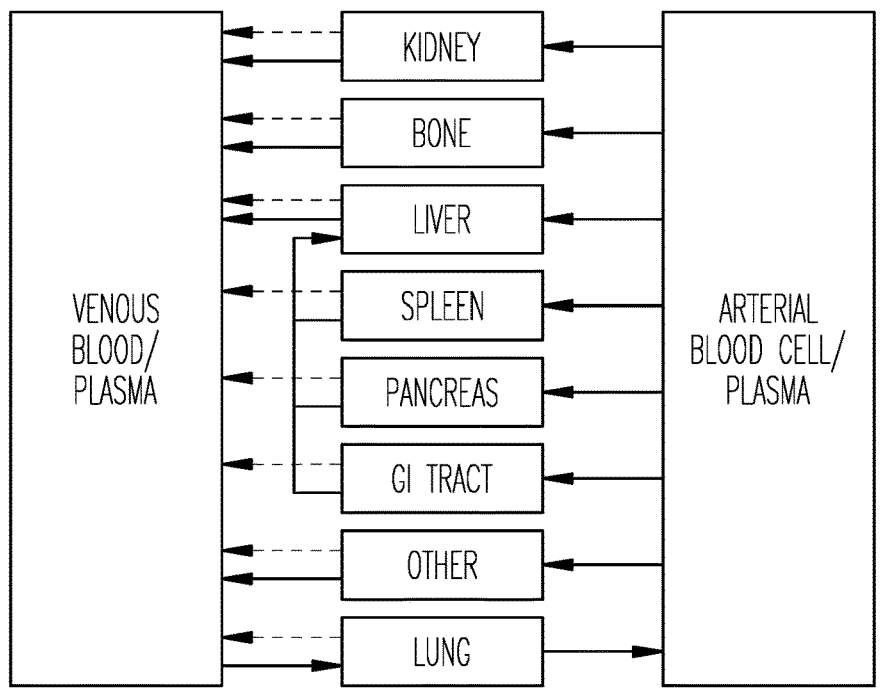
FIG. 11. Proposed whole-body structure of the PBPK model for MSNP deposition. Organs/tissue/blood pools are connected in an anatomical manner with blood (solid lines) and lymph (dashed lines) flows. Organ sub-compartmentalization is shown in FIG. 12. Central blood pools are separated into blood cell and plasma space FIG. 12. Organ level PBPK model structure for MSNPs. Additional processes may be included based on data from avian embryos on uptake in blood and tissue cells. O—organ blood flow; L—lymph flow; ov—vascular reflection coefficient (representative of organ specific vascular permeability); ai—interstitial reflection coefficient (representative of particle movement in the extracellular matrix); Kon & Koff—association and dissociation constants for the MSNP-hydroxyapatite coordinate covalent binding process; kdeg—rate of degradation of MSNPs in plasma (assumed similar in interstitial space); kdes—rate of phagocytic uptake due to the reticuloendothelial system (RES) included in lung, liver and spleen.
Figure 12:
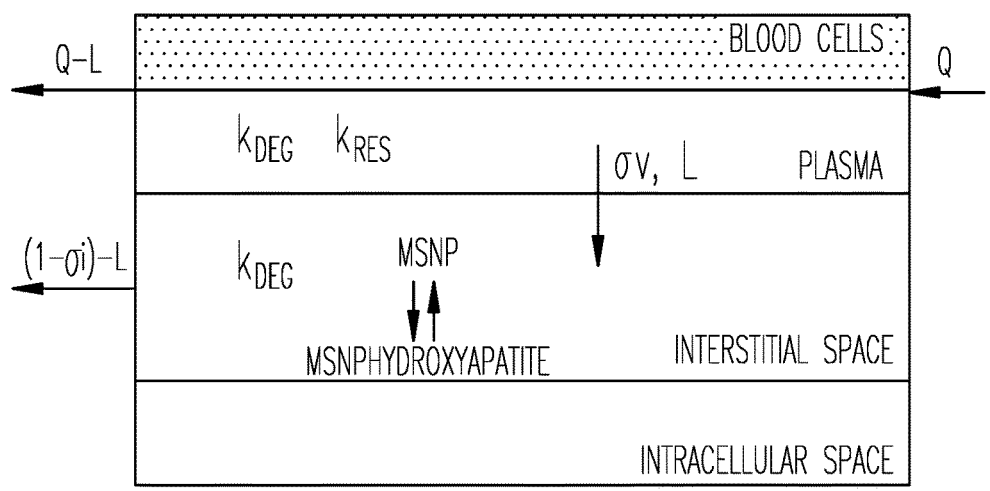
Figure 13A:
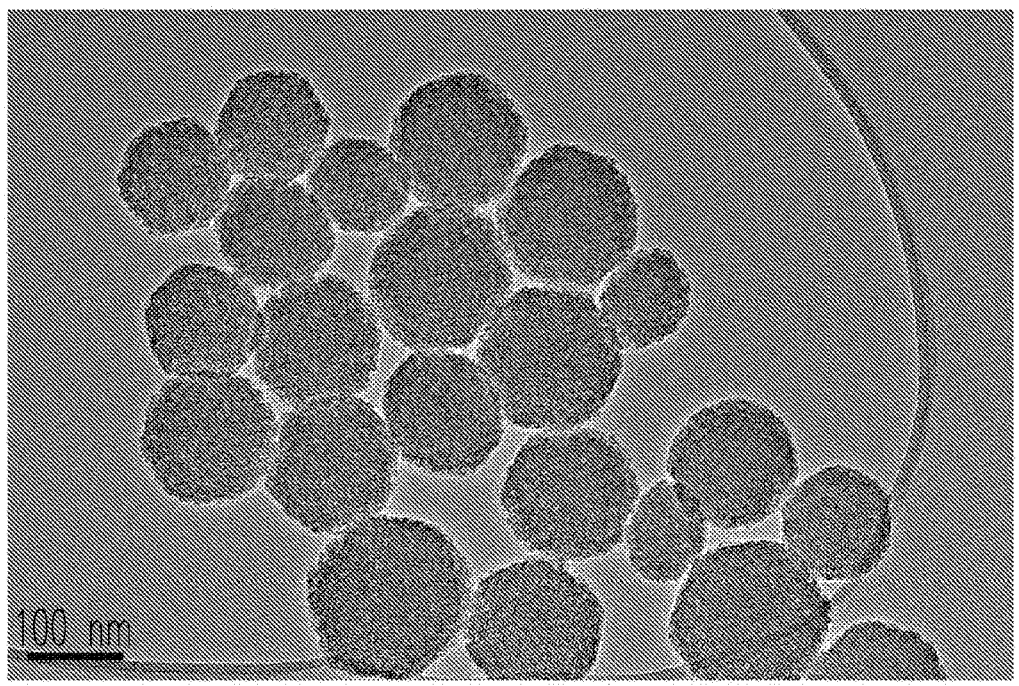
FIGS. 13A-B. Transmission electron microscopy (TEM) image of MSNPs treated with LaC13 solution. MSNPs with COOH-modification (A) do not have electron dense Lanthanum crystal formation, however, MSNPs with Bisphosphonate modification (B) show crystal formation on the majority of particles imaged. Lanthanum crystal growth on the bisphosphonate modified MSNPs supports successful MSNP conjugation process.
Figure 13B:
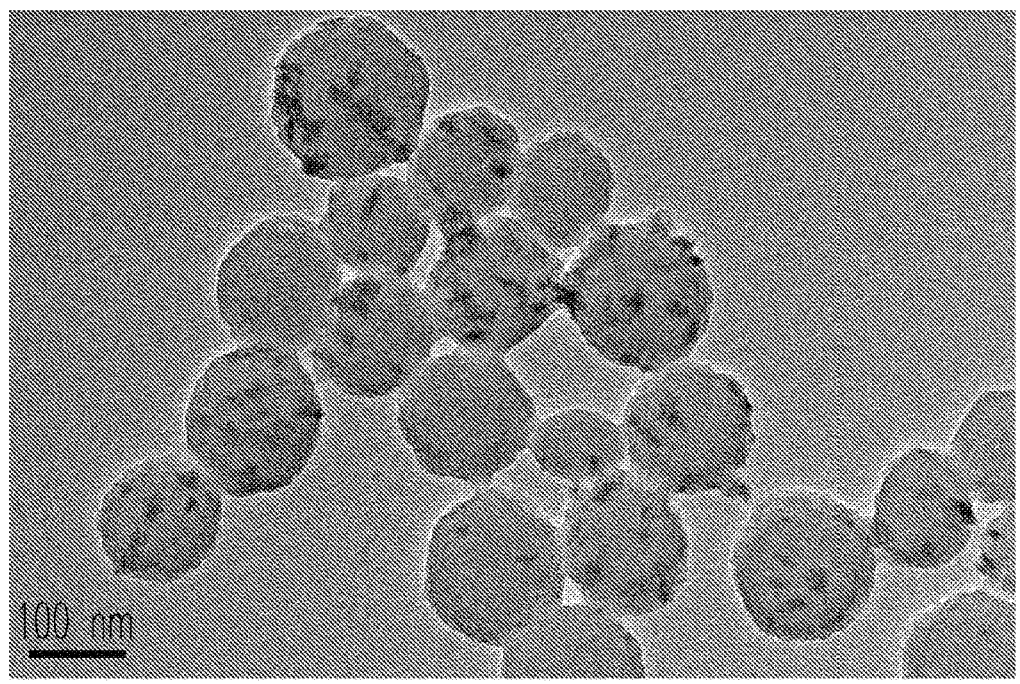
Figure 14:
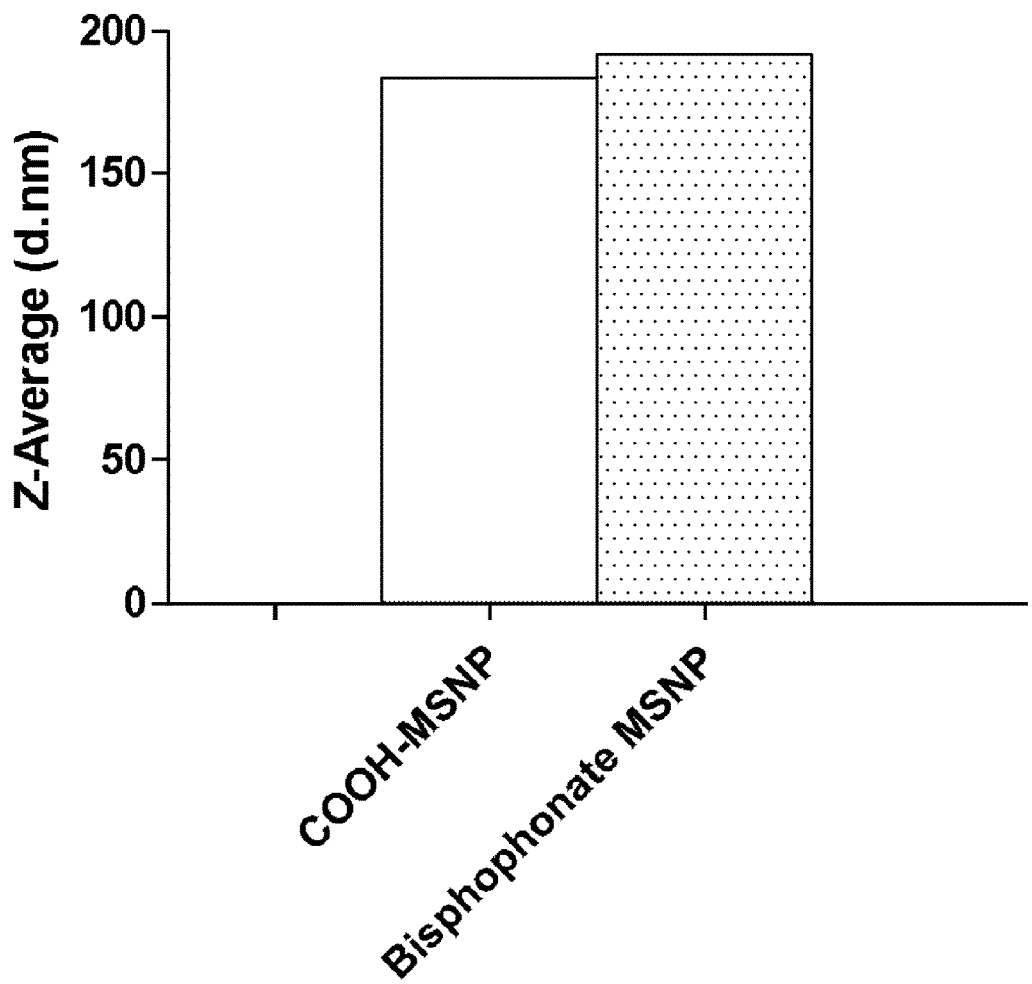
FIG. 14. Hydrodynamic size analysis of COOH modified MSNPs and bisphosphonate modified MSNPs in $H_2O$. Pre and post-modified MSNPs are colloidally stable with a low PdI value. Z-average size (n=6) COOH-MSNP=183.5±3.2 nm (PdI=0.034). Bisphosphonate-MSNP=191.8±1.8 nm (PdI=0.010).
Figure 15:
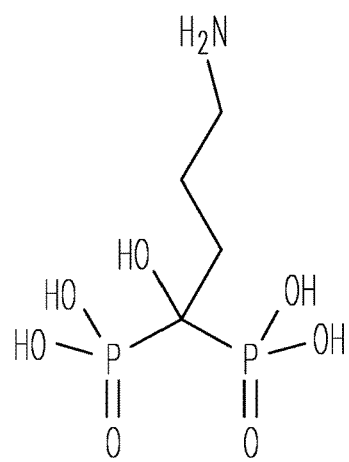
FIG. 15. MSNPs functionalized with a bisphosphonate molecule, e.g., Alendronate (alendronate treatment slows bone loss) using post-modification or co-condensation methods. The use of surface modified MSNPs may reduce or eliminate non-specific interactions with healthy tissues.
Figure 16A:
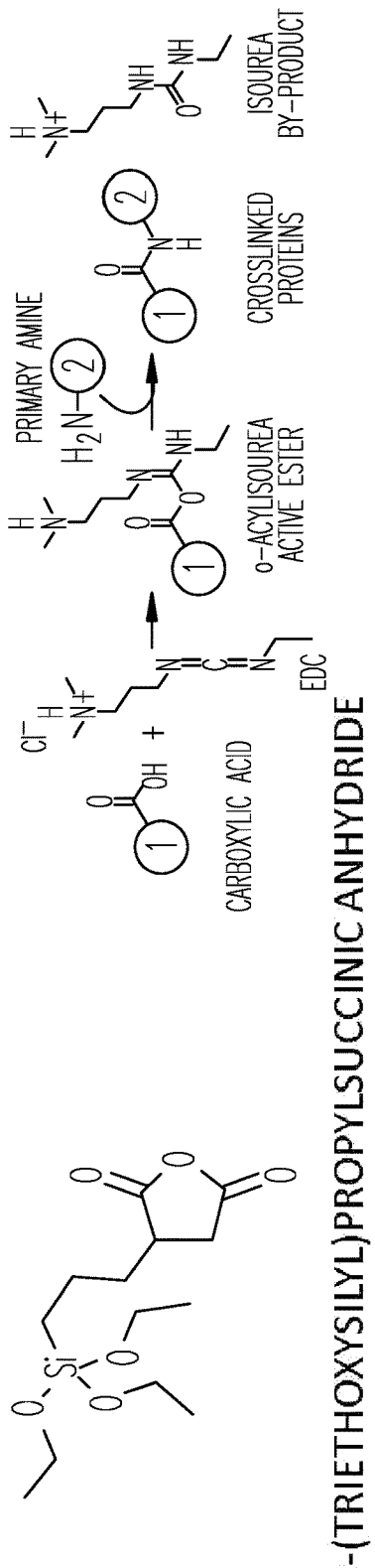
FIGS. 16A-C. A) Post-modification of MSNPs using heterobifunctional crosslinkers or click chemistry. B) TEM of COOH-modified (top) or DBCO-modified (bottom) MSNP cores. Hexagonal prism synthesis was used for COOH modified cores (PD2). 1 hour after TEOS addition, 50 μL of COOH-silane was added and stirred for about 1 hour. Standard methods were used for purification. For DBCO modified cores (PD42), biphase synthesis was used. DBCO-NHS was dissolved in DMF and three different aminated silanes (APTES (3 ethoxide groups), APDMES (2 ethoxide groups) and APDMES (1 ethoxide group)) were added to the aqueous phase before the organic phase was added, Standard methods for purification were then employed. C) $LaCl_3$ test.
Figure 16B:
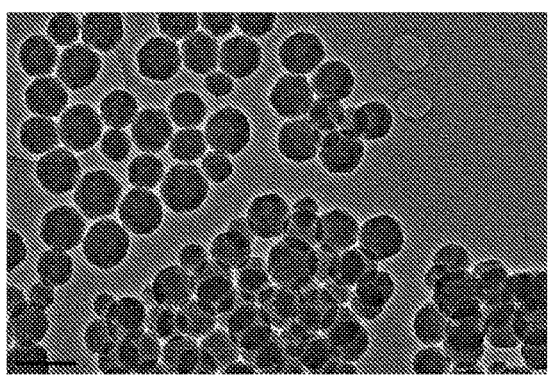
Figure 16C:
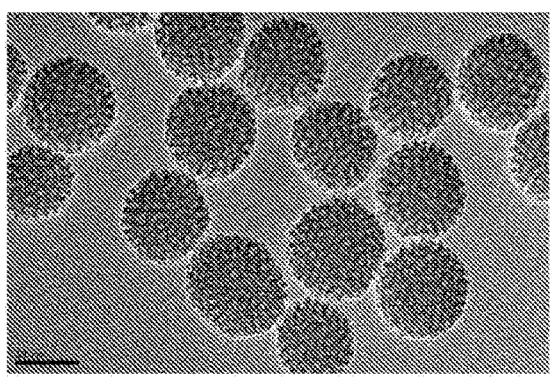
Figure 17A:
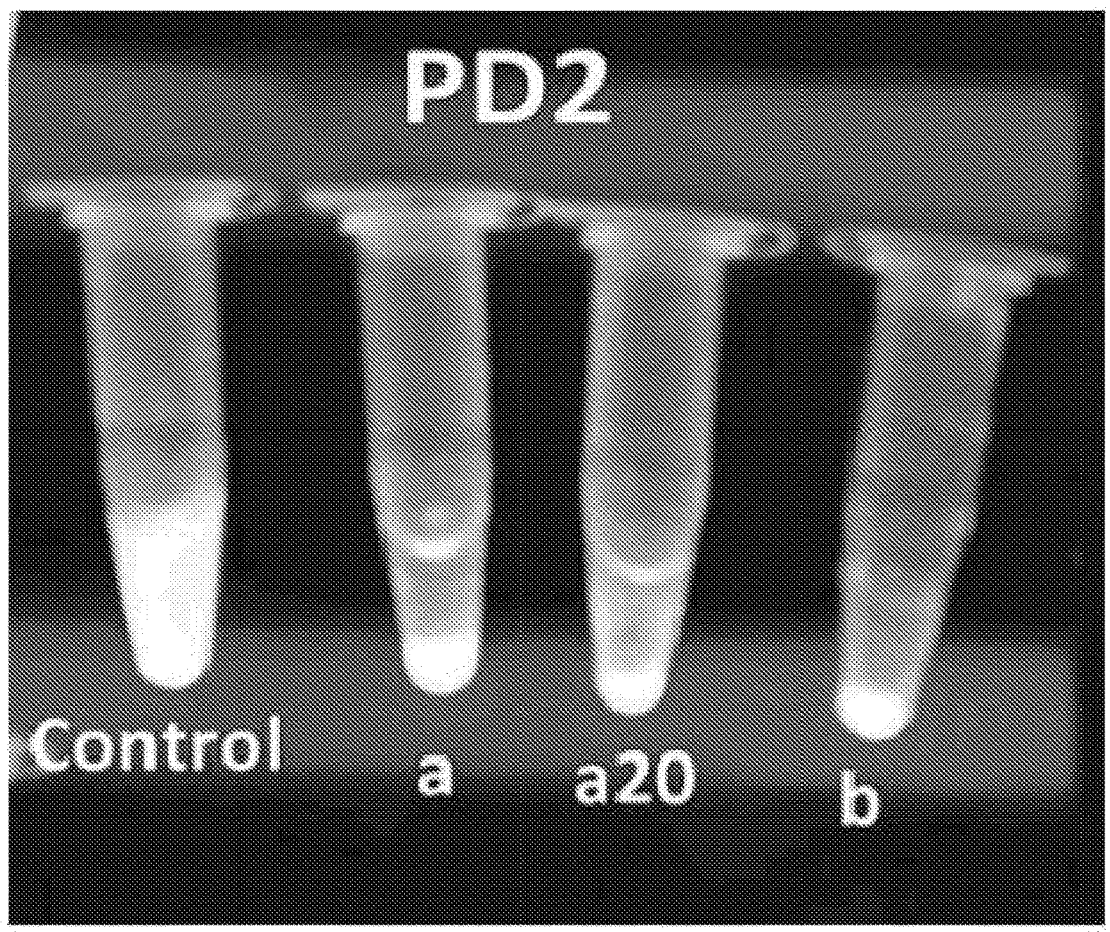
FIGS. 17A-E. A) TEM of COOH-modified MSNPs. B) TEM OF Bisphosphonate modified MSNPs. C) Hydrodynamic size measurements. Z-average size (n=6), COOH-MSNP=183.5±3.2 nm (PdI=0.034); bisphosphonate-MSNP=191.8±1.8 nm (PdI=0.010). D) $LaCl_3$ test. Control—COOH only; "a"=600 μg EDC was added to 2 mg MSNPs (pH 6) and incubated for 15 minutes to which 1.6 mg alendronate (pH 8.7) was then added; "a20"=200 μg EDC was added to 2 mg MSNPs and incubated for 15 minutes before adding 523 μg of alendronate; "b"=200 μg EDC, 2 mg MSN and 1.6 mg alendronate were combined at the same time. E) $LaCl_3$ test. Alendronate modification was 2:1 mol ratio alendronate:azidoacetic acid NHS (pH 6). The MSNPs were core modified by adding 500 μg alendronate azide to 1 mg PD42 (DBCO-modified core).
Figure 17B:
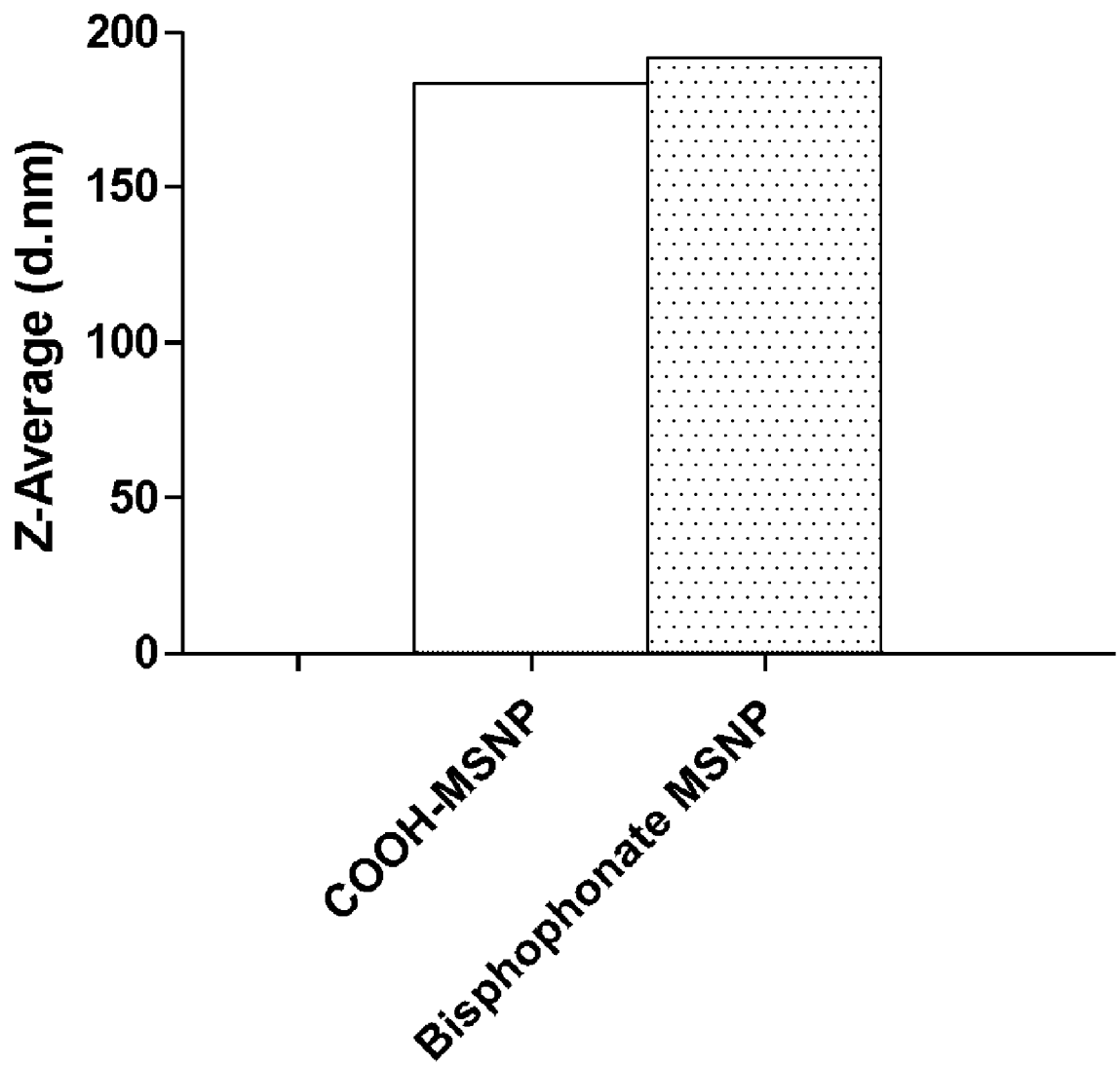
Figure 17C:
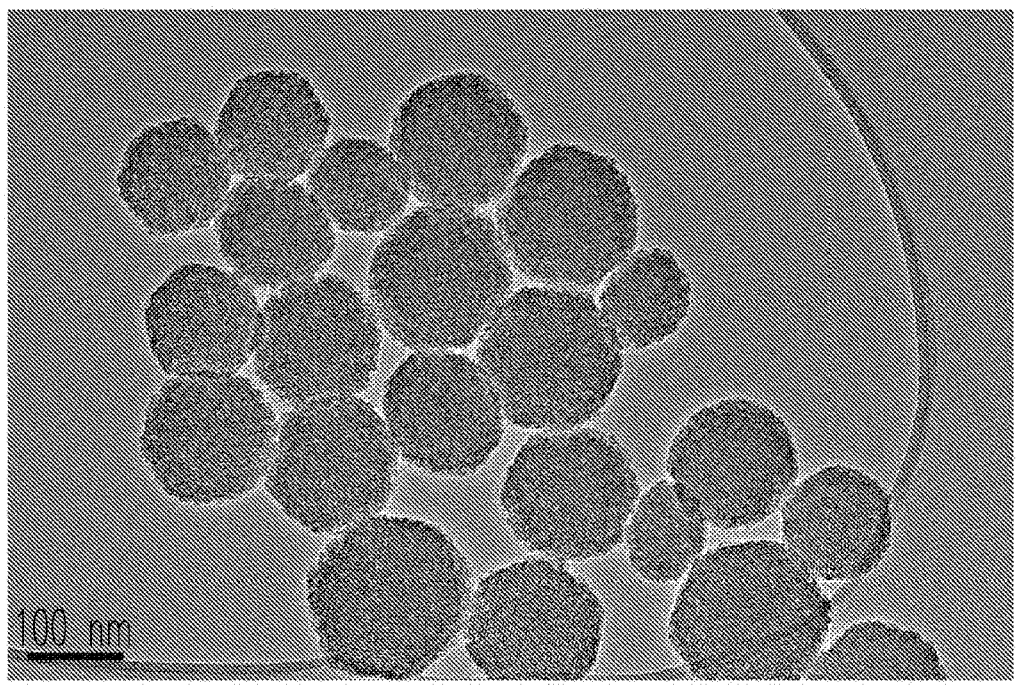
Figure 17D:
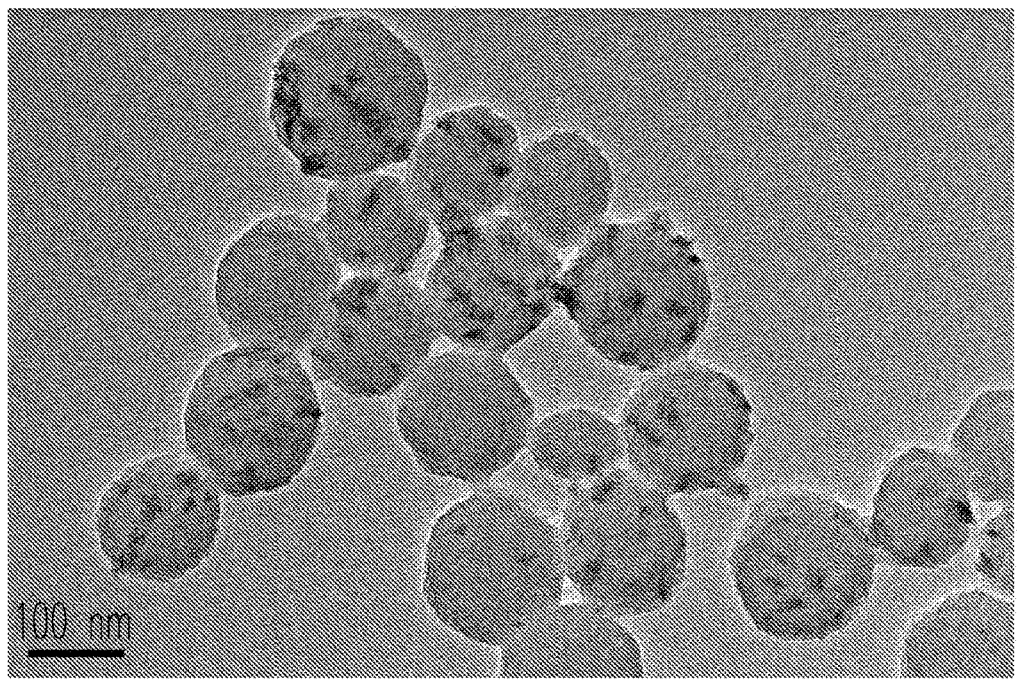
Figure 17E:
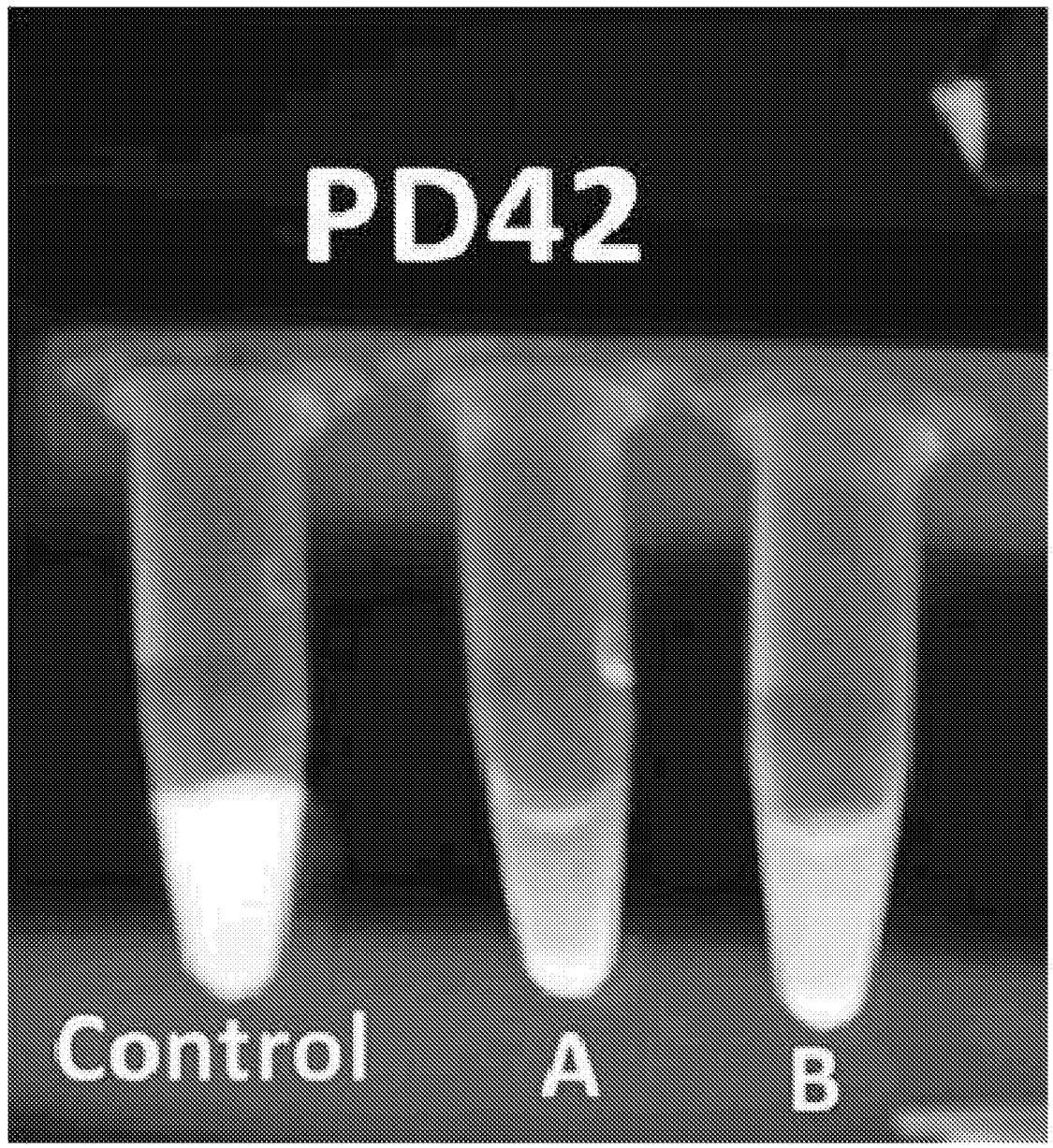

A PBPK mouse model is developed for assimilation of pharmacokinetic data. Once completed, this model will be modified to incorporate human-specific anatomical, physiological and biochemical information. Along with non-target toxicity data and efficacy data, the human model will be used to design a dosing regimen for a first-in-human trial. PBPK models use differential equations to describe mass transport between compartments which represent relevant anatomical and physiological spaces including organs, tissues, and body fluids. The proposed whole-body structure of the PBPK model for our nanoparticle is presented in FIG. 11. Lymph flow, an important distributional conduit for large molecules, and the circulatory system are incorporated. On an organ level (FIG. 12), processes account for vascular kinetics, extravasation and distribution due to lymph. This structure is a hybrid of PBPK models for monoclonal antibodies and silver nanoparticles and incorporates the features deemed required for accurate PK prediction of nanoparticles. PBPK model inputs include organism and nanoparticle-specific values. Organism-specific parameters such as organ volumes, blood flows and hematocrit are well defined for mouse and human. Lymph flow is estimated to be 100-SOOth that of organ blood flow. Organ-specific vascular and interstitial reflection coefficients are presented in Shah et al. Vascular reflection coefficients are used to define endothelial convective transport. The value of this reflection coefficient is a function of the presence of tight junctions (continuous endothelium) or their relative absence (fenestrated endothelium). Once the nanoparticle is in the interstitium, lymphatic flow is a mechanism of biodistribution for nanoparticles between 10 and 100 nm and the interstitial reflection coefficient represents the resistance offered by the extracellular matrix to movement of the nanoparticle to lymph. Degradation of MSNPs in plasma is derived ex vivo. The importance of phagocytosis via the RES to MSNP clearance in lung, liver and spleen, as was included in a PBPK model for silver nanoparticles, is evaluated using PK data from normal and immunocompromised mice. Some inputs will require optimization using observed PK data. Kinetic organ biodistribution data from Objective #1 will allow for optimization of reflection coefficients. Affinity constants, which define the coordinate covalent binding of bisphosphonates with hydroxyapatite (FIG. 11), can be optimized using data on bone biodistribution. The siRNA PBPK model is developed similarly to the MSNPs. Using standard approaches for the PBPK modeling of small molecules, the Docetaxel PBPK model is developed in mice and humans using literature data. Once a PBPK model for each payload is formed, they will be linked to the MSNP PBPK model such that drug release from the MSNPs will form the input to the drug models. This will allow us to examine how MSNP payload release kinetics as well as MSNP kinetics affect drug exposure in bone, plasma and non-target organs. The PBPK model is built in Matlab. PBPK model evaluation is critical. Sensitivity analysis will be employed for both the model structure as well as input parameters. Model evaluation is based on standard assessments of goodness-of-fit in all measured compartments (i.e. observed vs simulated organ PK).

One goal is to extrapolate the mouse model to humans for the planning of a first-in-human trial. PBPK models are well suited to inter-species extrapolation and are widely used in both human health risk assessment and pharmaceutical development for this purpose. The human model will have the same structure as the mouse model but will contain human-specific parameter values. Using toxicity data from non-target organs (e.g. NOAEL) and knowledge of the MSNP dose vs. bone exposure relationship plus PK and MSNP dose vs. tumor reduction relationship (Objective #2), a dosing regimen for human will be developed. Simulations are performed under varying MSNP dosing scenarios where the goal is the identification of a dosing regimen that reduces nontarget deposition while maintaining bone MSNP concentrations that are linked to efficacy. MSNP and payload exposure in plasma, bone and any off-target tissue included in the model can be easily tracked in the simulations.

This targeted drug delivery system will permit maximal delivery of cargo directly to the bone metastases' microenvironment.

Example 2

Exemplary Synthesis
MSNP Synthesis

Prismatic hexagonal structured MSNP are synthesized using techniques described in the literature (see Lin, Y.-S.; Haynes, C. L. impacts of Mesoporous Silica Nanoparticle Size, Pore Ordering, and Pore Integrity on Hemolytic Activity. Journal of the American Chemical Society 2010, 132, 4834-4842 and Lin, Y.-S.; Abadeer, N.; Hurley, K. R.; Haynes, C. L. Ultrastable, Redispersible, Small, and Highly Organomodified Mesoporous Silica Nanotherapeutics. Journal of the American Chemical Society 2011, 133, 20444-20457.).
Pore Size To make large pore spherical MSNPs, one follows the synthesis procedure described in the literature (see, Wang, J.; Sugawara-Narutaki, A.; Shimojirna, A.; Okubo, T. Biphasic synthesis of colloidal mesoporous silica nanoparticles using primary amine catalysts. Journal of Colloid and Interface Science 2012, 385, 41-47 and Shen. D.; Yang, J.; Li, X.; Zho, L.; Zhang, R.; Li, W.; Chen, L.; Wang, R.; Zhang, F.; Zhao, D. Biphase Stratification Approach to Three-Dimensional Dendritic Biodegradable Mesoporous Silica Nanospheres. Nano Letters 2014, 14, 923-932) (Moeller, Karin, et al. "Highly Efficient siRNA Delivery from Core-Shell Mesoporous Silica Nanoparticles with Multifunctional Polymer Caps." *Nanoscale* (2015). Purification process was the same as described by Yu-Shen's papers. (Lin, Y.-S.; Abadeer, N.; Hurley, K. R.; Haynes, C. L. Ultrastable, Redispersible, Small, and Highly Organomodified Mesoporous Silica Nanotherapeutics. Journal of the American Chemical Society 2011, 133, 20444-20457.) *Conjugation of Bisphosphonate to Lipid Bilayer of Protocells*

The bisphosphonates may be conjugated to the phospholipid bilayer of the protocell by forming a thiol group from an amine of an amine-containing phospholipid (using Traut's reagent) and then reacting the incipient thiol group with an NHS-Maleimide crosslinker (Including AMAS, BMPS, GMBS, Sulfo-GMBS, MBS, Sulfo-MBS, SMCC, Sulfo-SMCC, EMCS, Sulfo-EMCS, SMPB, Sulfo-SMPB, SMPH, LC-SMCC, and Sulfo-KMUS) as crosslinking agent to link the thiol group of the lipid with an amine of bisphosphonate.

Protocells are prepared using standard methods. Briefly, MSNPs are mixed with liposomes in aqueous buffer and washed to remove free liposomes in solution.

Liposome preparations used include 1. DSPC/DOPE/ Cholesterol (60/30/10 mass %). 2. DSPC/DOPE/Cholesterol/DSPE-PEG 2000 (60115115110 mass %), and 3. DSPC/DSPE/Cholesterol/DSPE-PEG 2000 (60/15/15/10). Basically, the lipid bilayer can comprise a large of different formulations, but in conjugating the bisphosphonate to the lipid bilayer, the approach should include a significant amount of lipids with head groups which contain a primary amine for use in the bisphosphonate conjugation.
Bisphosphonate Modification to Supported Lipid Bilayer Bisphosphonate protocells can be prepared by converting primary amine terminated lipid head groups to sulfhydryl terminated head groups using Traut's reagent. N-amaleimidoacetoxysuccinimide ester (AMAS) crosslinks the sulfhydryl group on the lipid head group to the amine on the bisphosphonate molecule (added in molar excess) upon incubation at room temperature for 30 minutes to 2 hours. This reaction can be performed in reverse as well, with Traut's modification to the bisphosphonate and reaction with aminated lipid head groups, however it would require a purification step to eliminate bisphosphonate molecules that have not reacted.

The conjugation of bisphosphonate to protocells may be performed 3 ways. In a first method, AMAS is reacted with protocells first, then bisphosphonate added second. In a second method, AMAS is reacted with bisphosphonate first, then added to protocells. In a third method, AMAS is reacted with protocells and bisphosphonate simultaneously.

In the protocells up to at least about 50% or more of the surface of the protocell e may be covered with bisphosphonates. This estimate is theoretical. Post-modification of COOH-modified MSNPs, or click-modified MSNPs will occur both within the pores and on the exterior surface of the MSNPs. Since the methods used to incorporate the reactive groups with result in distribution throughout the entire MSNP framework. The size of the molecule is small enough that it will react within the pores and on the particle exterior. Based upon experiments, there should be a significant portion of the exterior surface area available for surface modification. Accordingly, the surface covering by the bisphosphonates tends to be high—up to about 50% of the protocell (at least about 2%, about 5%, about 10%, about 15%, about 20%, about 25%, about 30%, about 35%, about 40%, about 45%, about 46%, about 47%, about 48%, about 49%, about 50% of the surface of the lipid bilayer of the protocell and often from about 50% up to about 100% of the surface of the MSNP.
Protocelis An osteotropic (bone-specific) silica supported lipid bilayer nanoparticle (protocell) for drug delivery system was developed that when administered preferentially accumulates in bone first. After targeting to bone, protocells will then elute a multiplatform therapeutic payload (small molecules, siRNA) into the tumor microenvironment that will maximize the anti-cancer effect and minimize exposure to tissues outside of bone. The core nanoparticle, composed of mesoporous silica, which provides an immense internal surface area and can be loaded with therapeutic cargo by surface adsorption via electrostatic interactions, chemical conjugation, hydrogen bonding, and/or hydrophobic interactions. After cargo is adsorbed to the core nanoparticle, it is enveloped in a lipid bilayer to seal and protect the therapeutic cargo. The lipid bilayer is modified to display bisphosphonate molecules which will result in preferential accumulation of the osteotropic protocell drug delivery system in bone. Cargo release can be dictated by silica dissolution (if chemically conjugated to the MSNP architecture) or upon rupture of the lipid bilayer coating.

Therapeutic cargo loading is achieved using methods unique to each drug. For example, doxorubicin loading is largely driven by electrostatic interaction of positively charged drug with negatively charged MSNP surface. Docetaxel, likewise, requires hydrophobic modification of the MSNP and loading occurs through solvent evaporation and the fusion of a lipid cap to make the particles soluble in aqueous buffer. Finally, nucleic acid loading requires increased pore size and chemical conjugation techniques to tether the cargo to the MSNP surface. Drug release will occur as the silica framework dissolves through hydrolysis, and the majority of the adsorbed, encapsulated, and/or anchored drug within the nanoparticle will be released in a slow, and controlled manner related to the dissolution rate of the framework. This passive release of cargo will remain localized near the original site of MSNP arrest and will be released into the surrounding area.

Packaging of cargo into protocells protects serum-sensitive cargo such as siRNA/peptides, and restrict their systemic circulation by targeting a mineralized substrate (hydroxyapatite) that is abundant within prostate cancer bone metastases. This bone-specific drug delivery system will also deliver drugs previously unsuitable for patients with advanced stages of cancer, opening up the door for many other treatments that were previously too cytotoxic due to a systemic route of delivery. The use of mesoporous silica as the core of the nanoparticles is another important feature of this technology because it is capable of self-hydrolysis resulting in safe catabolization in the human body, is non-toxic even when administered at high levels, can readily adsorb a significant amount of therapeutic payload into its core, and is inexpensive to synthesize.

Advanced prostate cancer specifically spreads to the bone marrow, eventually colonizing the rib cage and all major bones. It remains unclear why bone marrow is the exclusive "soil" for the "seed" of prostate cancer but few treatments exploit this fact. In the bone, prostate cancer "seeds" eventually grow into metastatic colonies, releasing more prostate cancer "seed" while building more bone at these sites. To combat metastatic colonies, we have developed a bone-specific drug delivery system using specialized nanoparticles that perform multiple actions. First, these protocells will bind to normal and newly formed bone, subsequently preventing further bone damage by the metastatic colonies. Secondly, these protocells will then release a payload of anti-cancer drugs for tunable controlled release into nearby metastatic colonies. Lastly, as the drug is released, the protocells will eventually degrade and be readily excreted via urine posing no toxicity to the patient. The advantages of this drug delivery system are that various imaging agents and drug combinations can be incorporated into these bone targeting nanoparticles, thereby improving the half-life of these drugs and improving therapeutic efficacy—ideal qualities of a next generation theranostic. A wide range of payloads such as chemotherapy, anti-cancer proteins/peptides, and gene targeting RNA can be incorporated as well, improving delivery to metastatic colonies while minimizing their toxic effects in the general blood circulation. More importantly, gene-targeting RNA drugs can be developed for specific mutations or cell processes to interfere with the tumor cell's ability to spread away from the metastatic colony, restricting its ability to form more colonies in the bone.

The ability to deliver cytotoxic agents to bone metastases while minimizing their systemic effects is a key quality of this technology and will allow many researchers and companies to revisit therapies for use in targeting bone metastases. The majority of cancer deaths in North America are due to prostate and breast cancer bone metastases and there are very few drugs that target bone metastases specifically. This drug delivery system will enable the re-discovery of drugs at higher concentrations to halt the growth of bone metastases and allow pharma to develop novel nanoparticle drug formulations to treat these advanced stage cancers. Due to the highly porous nature of mesoporous nanoparticles, siRNA, peptides, protein, and small molecules regardless of charge can be readily adsorbed into these nanoparticles, offering a highly efficient means of delivering cargo to bone in a protected manner.

The disclosed MSNPs and protocells are likely effective treatments for men with high-risk or metastatic prostate cancer and optimizes the physical health of men with advanced prostate cancer. The drug delivery system minimizes cytotoxicity often associated with systemic administration of drug by delivering drug only to sites of bone metastases. In doing so, lower doses of drug can be administered, thus enhancing the quality of life for men with advanced prostate cancer. This drug delivery system can efficiently store drug/siRNA for specific delivery to bone, which will be released in a slow controlled manner to adjacent bone metastases and bone marrow, whereas systemic delivery often results in the degradation of the siRNA or biologics-based cargo.

The pharmaceutical industry has developed treatments that only alleviate cancer pain (bisphosphonates) caused by bone metastases in prostate cancer, breast cancer, and multiple myeloma patients. None of these treatments directly ablate bone metastases because these are cancers that are protected by the bone and are surgically inaccessible, making bone metastases refractory to most available treatments. Our osteotropic drug delivery system is effective because it can deliver serum-sensitive cargo to the mineralized portion of bone first before releasing the therapeutic payload. It opens the door for using therapeutics that are too toxic for systemic administration but can be therapeutically valuable if released into the bone tumor microenvironment in a slow and controlled manner. Silica-based nanoparticles are not immunogenic compared to polymeric nanoparticles, and offer exquisite ability to synthesis highly uniform and consistently sized porous nanoparticles for adsorption of cargo. The disclosed theranostic platform is also independent of protein/cell based targeting because it relies on bisphosphonates to bind to hydroxyapatite, the mineralized component of bone. This bone-homing quality will waste less drug while delivering more cargo directly at the site of bone metastases within the bone. This technology will revisit the possibility of using drugs that were initially too toxic or too sensitive to serum degradation by direct and protected delivery to bone metastases.

One aspect integrates experimental data for the rational prediction of an optimal human protocell (a MSNP with a lipid bilayer coating) dose that maximizes bone targeting and minimizes plasma circulation. As such, a knowledge integration platform will be developed for assimilation of pre-clinical pharmacokinetic and efficacy data derived in this project with an eye towards its use in inter-species scaling from mouse to human. This translational platform is called a physiologically-based pharmacokinetic/pharmacodynamic model (PBPK/PD). PBPK models are commonly used for small molecule interspecies (e.g. preclinical species to adult human) and intraspecies (e.g., adult to child) scaling of pharmacokinetics. Because PBPK models are mechanistic and thus based on a rational understanding of the system of study (e.g. the organism) and the applied drug/molecule, these models are formed with a biological basis and complex interactions of the system with the drug/molecule can be investigated. PBPK modeling has been recognized as important support tools for nanoparticle hazard assessment by several regulatory bodies. Model structure in this project will be developed specifically for our nanoparticle technology, incorporating salient features of the 1) circulatory system, 2) organ-specific vascular permeability, extracellular matrices and lymphatics, 3) specific binding properties in bone, and 4) excretion via kidney, degradation and/or the reticulendothelial (RES) system. The PD component of the model will link bone exposure to tumor reduction. The Edginton lab has previously developed a large molecule PBPK platform for the planning and execution of a first-in-man trial [termed Model-Based Drug Development (MBDD)] through leveraging knowledge of the drug-preclinical species interaction with further extrapolation to man. This platform will integrate different levels of information and be used to develop a dose and dosing regimen for humans that will ensure efficacy at the site of action while minimizing non-target exposure.

Example 3

MSNPs may be functionalized with drugs, such as a bisphosphonate molecule, using post-modification or co-condensation methods.
Delayed Modification Co-Condensation COOH-modified MSNPs were prepared using hexagonal prism synthesis. CTAB is added to aqueous phase and either COOH-silane, or to DMBO-modified silanes, e.g., modified with one of three different aminated silanes, i.e., APTES (3 ethoxide groups), APMDES (2 ethoxide groups), APDMES (1 ethoxide group), dissolved in DMF, is also added to the aqueous phase and the mixture added to the aqueous phase before addition of the organic phase. TEOS is dissolved in the organic phase. FIGS. 13-18 show results with COOH-modified MSNPs and DBCO-modified MSNPs.

Figure 20A:
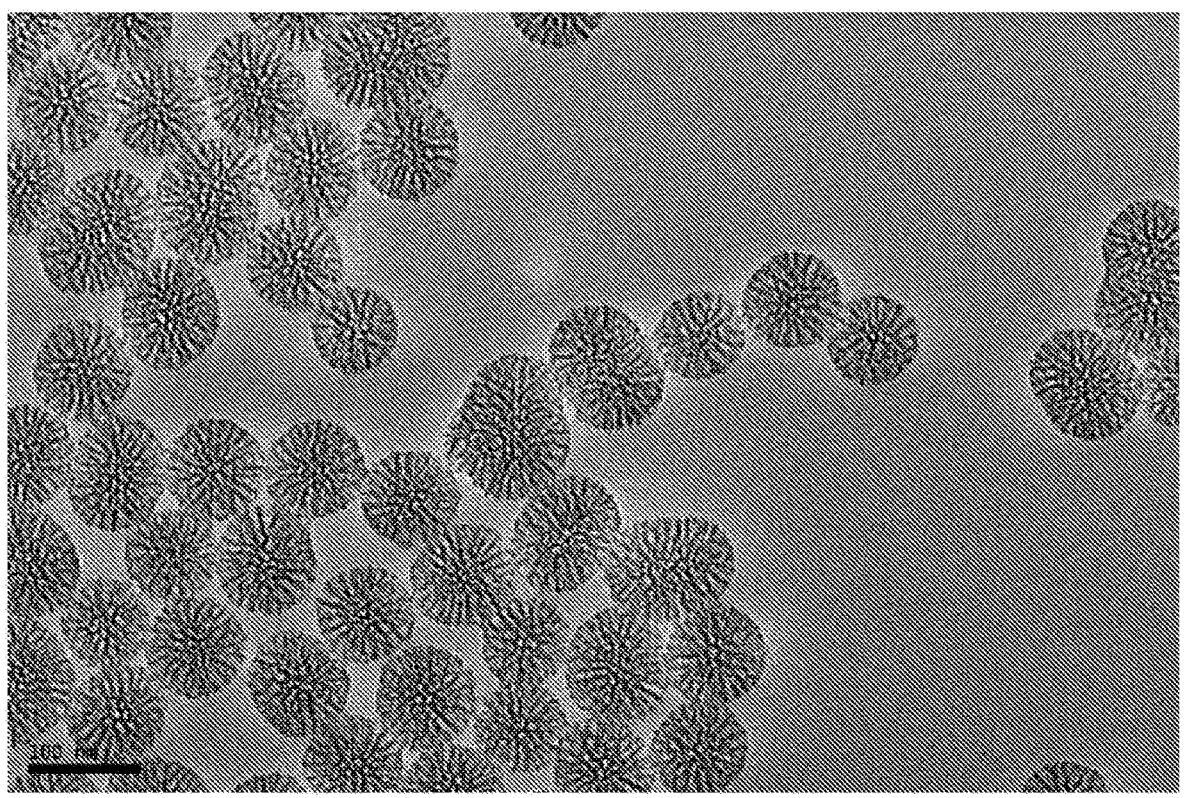
FIGS. 20A-C. Particles with a zwitterionic coating are stable in water. A) TEM of PD47 MSNPs. B) Elemental analysis of PD47 MSNPs. The inset shows the surface modification with zwitterionic silane, and the red circle shows the presence of sulfur. C) Particle pore size. PD47 (alendronate/zwitterionic.)=138.0 nm (0.079), PD48 (zwitterionic)=190.9 nm (0.063). PD47 zeta potential=−23.8±0.907 mV, and PD48 zeta potential=−20.1±0.666 mV.
Figure 20B:
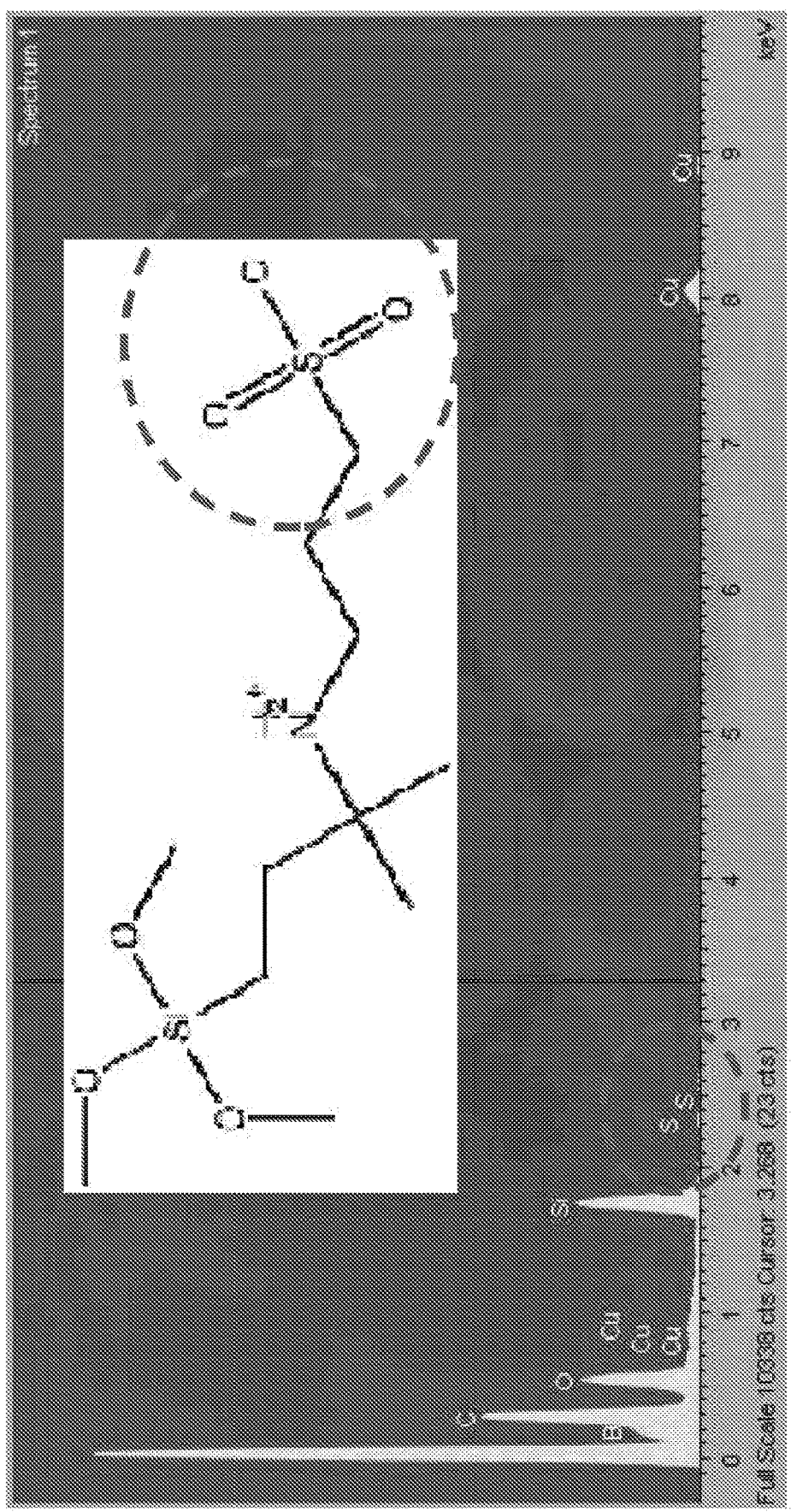
Figure 20C:
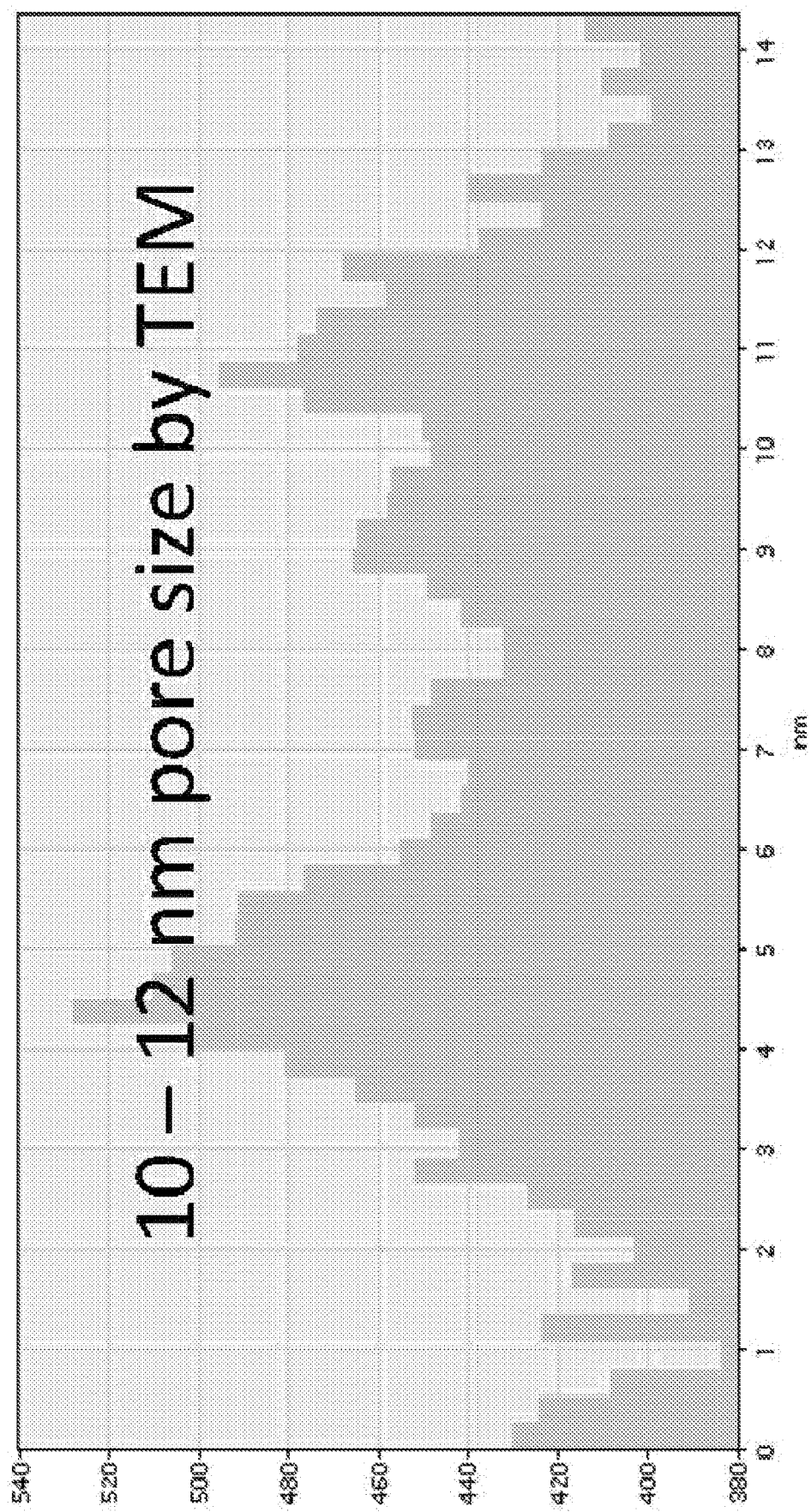
Figure 21A:
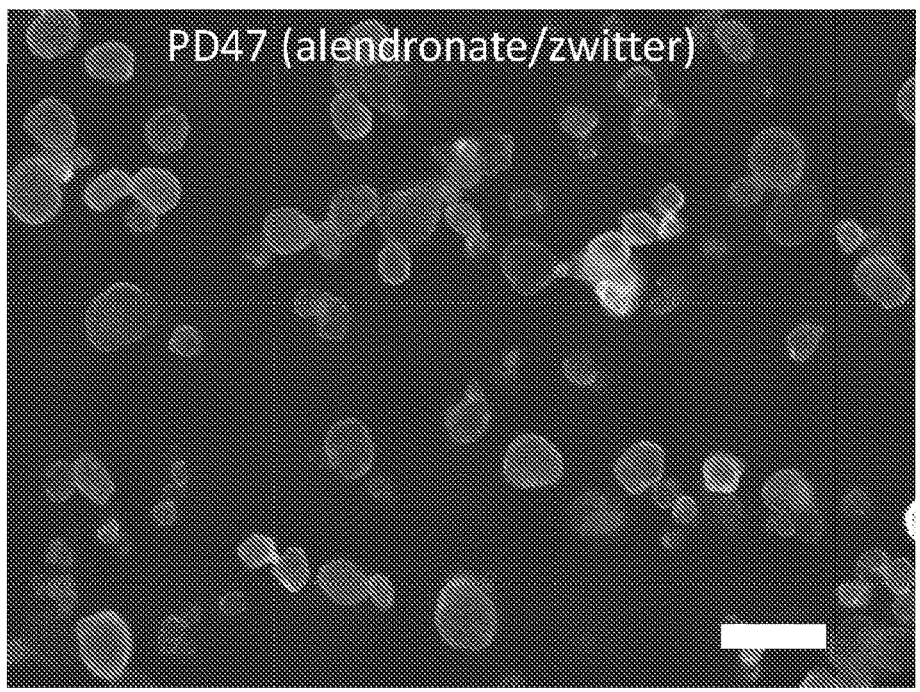
FIGS. 21A-B. Hydroxyapatite test shows increased fluorescence with Alendronate modified MSNPs. About 50 mg of HA was suspended in PBS then 25 μg of MSNPs were added and incubated for 15 minutes. The sample was then washed 3 times in PBS then placed on glass coverslip before imaging (150 ms exposure). Left image shows HA+PD47 (targeted) and right image shows HA+PD48 (non-targeted) (same exposure time).
Figure 21B:
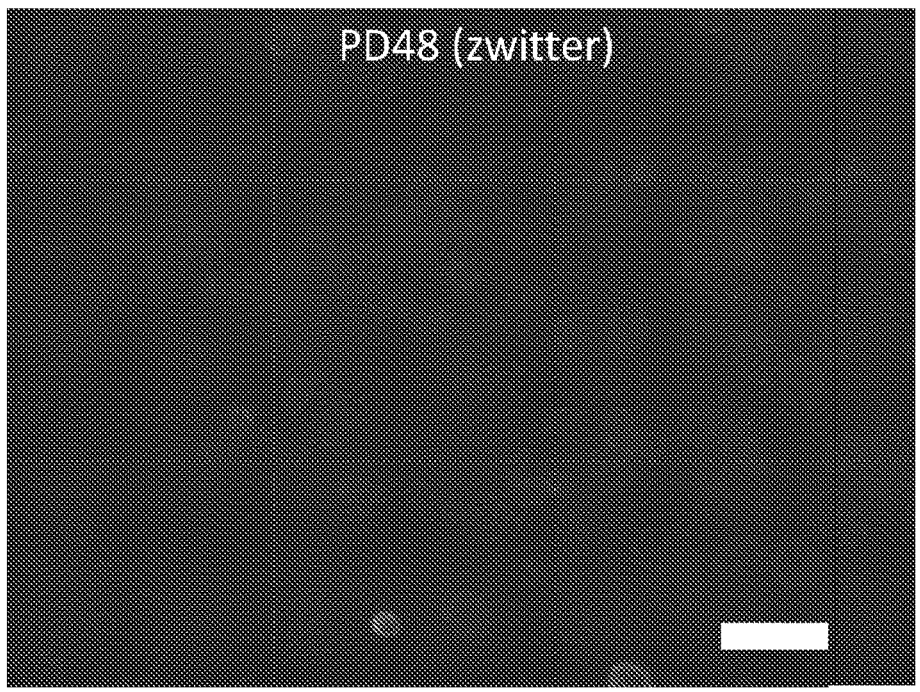
Figure 22A:
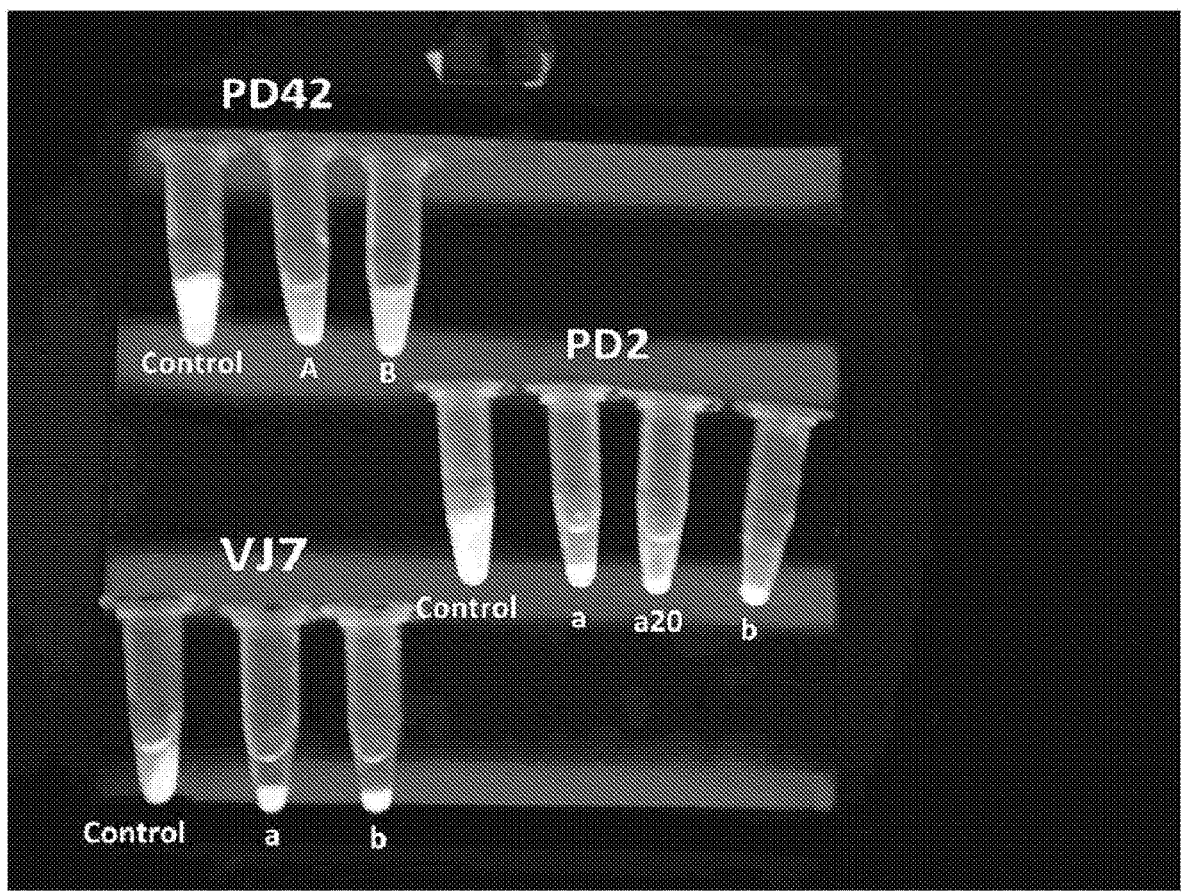
FIGS. 22A-B. A) Summary of LaCl$_3$ tests. B) TEM of PD42-DBCO modified particles.
Figure 22B:
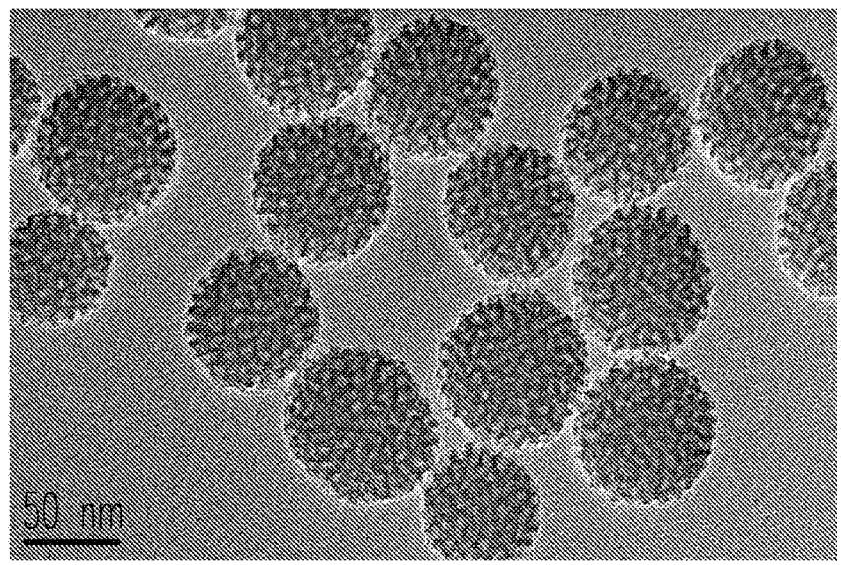
Figure 23A:
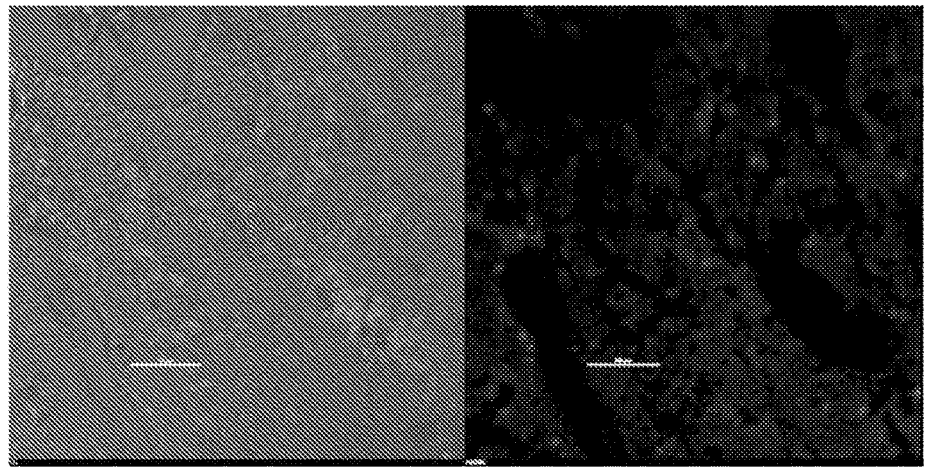
FIGS. 23A-C. Bright field and fluorescent staining of PD47 in tibia (A), liver (B) and heart (C).
Figure 23B:
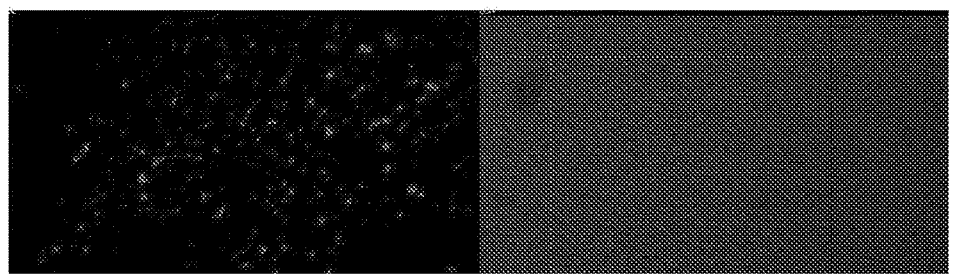
Figure 23C:
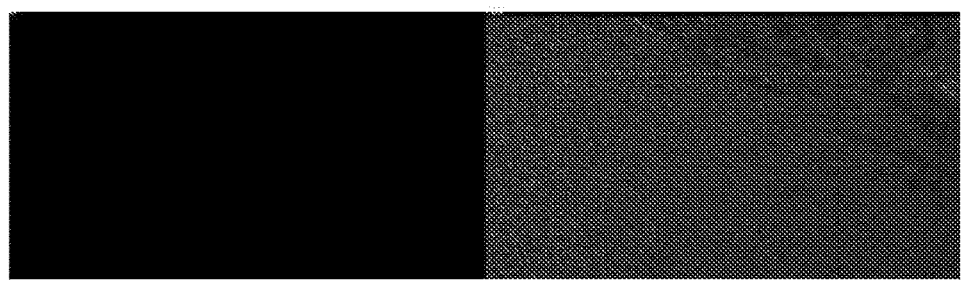
Figure 24A:
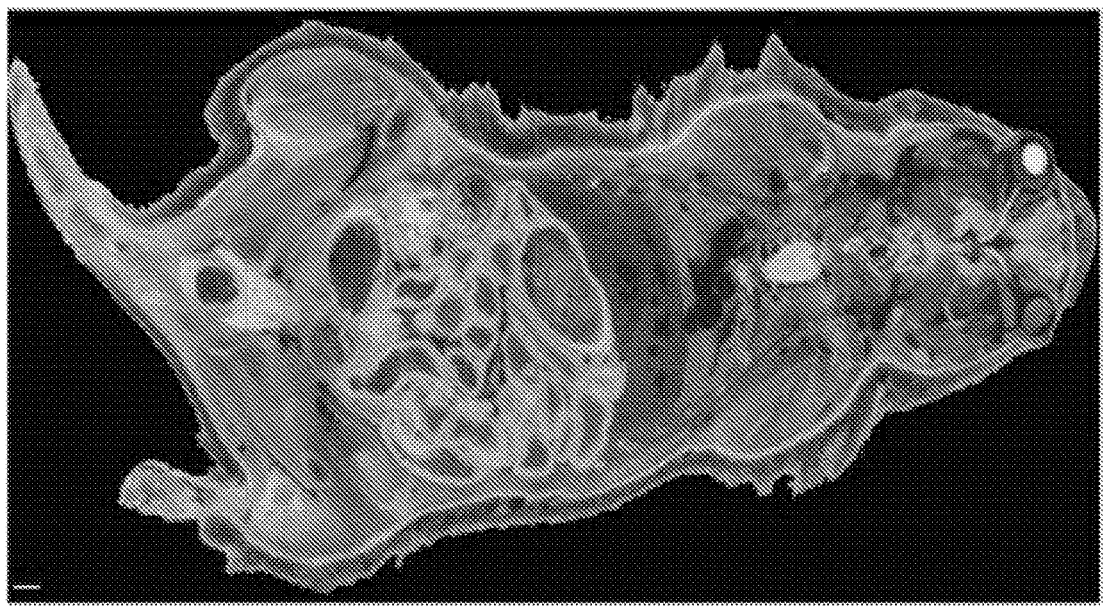
FIGS. 24A-G. A) Cryo-image of a whole adult mouse showing coronal section 448 out of 663 sections. The image was composited from 20 tiled acquisitions and has an original size of 5,300×2,100 pixels at 15.6 μm in-plane pixel size. The image background has been changed to black using automated image processing. Major organs like eyes, heart, lungs, liver, stomach, small intestine, and colon are easily identified. Note this compressed image shows clearly the right and left optic nerves, the rectus muscles of the eyes, the septa in the nose and the ribs. (Bar=2 mm). B-G) 3D visualization of cryo-images. B) Volume visualization of the whole mouse from 2D sections shown in FIG. 24A. A total of 13,260 individual images were used to create this true-color visualization. A cutaway shows views in three orthogonal planes. The coronal section was the cutting plane whereas the axial and sagittal sections have been digitally extracted. C) 3D reconstruction from the manually segmented lungs with vasculature segmented through semi-automatic seeded region growing. D) Segmentation-free volume visualization in which the same lungs (deep red) have been segmented automatically by optimizing the opacity for this tissue type. Skin was digitally removed to reveal organs like the brain, spinal cord and gastro-intestinal system. E) A color feature detector with combinational color and step opacity transfer function was used to automatically segment the stomach and intestines. F) Low-resolution volume visualization of the liver with 3D surface reconstruction of hepatic vessels with a 3D zoom view (G) showing a vessel branch at higher resolution.
Figure 24B:
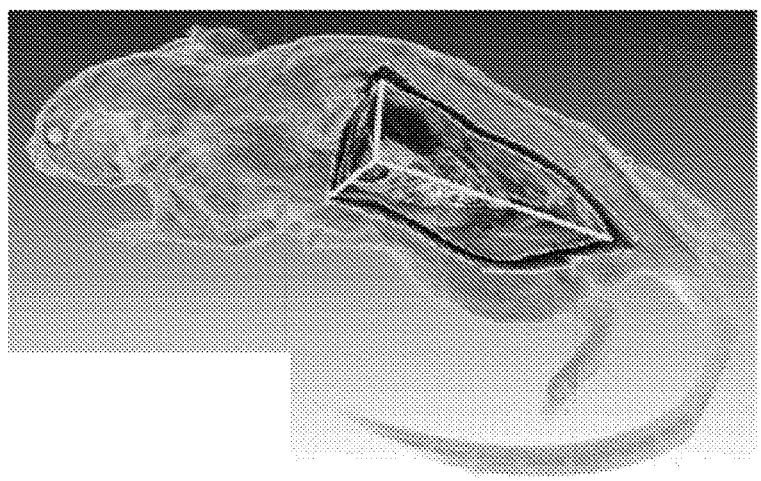
Figure 24C:
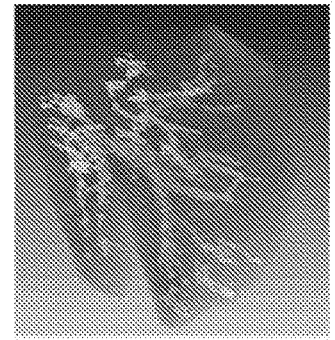
Figure 24D:
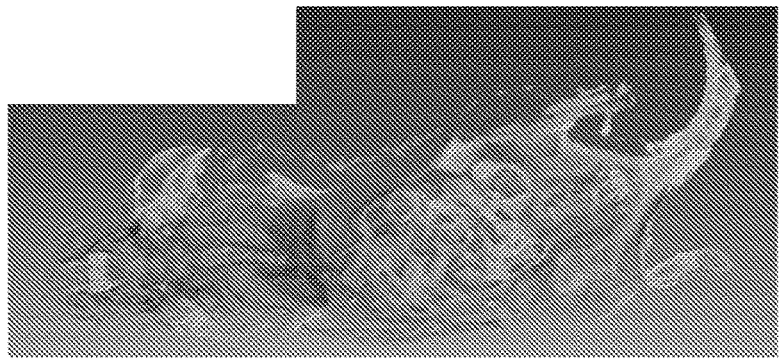
Figure 24E:
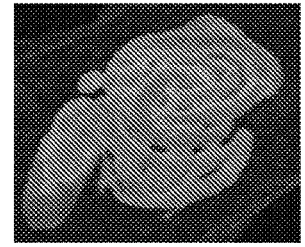
Figure 24F:
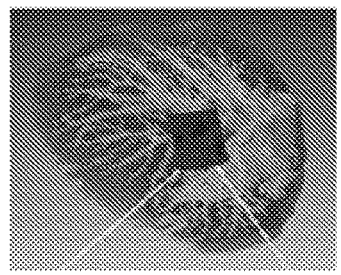
Figure 24G:
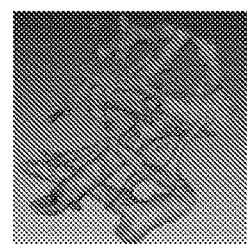

Alendronate is only soluble in water. The zwitterionic silane shown in FIG. 19 is only soluble in water. 1 mg Epoxysilane was added to 11.5 mg alendronate (1 hr), then MSNPs (20 mg) were added, after which 20 mg Zwitter silane powder was added.
DLS
AK4=89.07 nm (0.025)
AK4 (alendronate/zwitter)=87.78 nm (0.014)
AK4 (zwitter)=89.00 nm (0.008)
Zeta Potentials
−19.5±0.929 mV
−19.3±0.416 mV
−23.5±0.586 mV
Co-Condensation Biphase synthesis method (27 hours and 50° C.) was used for PD47 and PD48. For Zwitterionic+Alendronate, 2 mg Epoxysilane+11.5 mg Alendronate (1:5 mol ratio) were mixed for 3.5 hours in water (other buffers might be used DMF, EtOH, cyclohexane, and the like) and then was added to (aq) phase for 30 minutes. 500 mg Zwitterionic silane was dissolved in water and added to (aq) phase. That mixture was continuously stirred for 7 hours. The organic phase was discarded and the (aq) phase treated at 70° C. for 24 hours. Standard purification methods were then employed. For Zwitterionic only, 500 mg Zwitterionic silane was dissolved in water and added to (aq) phase. Continuous stirring was conducted for 7 hours. See FIGS. 20-22.
DLS (EtOH)
PD47 (alendronate/zwitterionic)=1710 nm (0.332)
PD48 (zwitterionic)=1945 nm (0.259)
DLS (Water)
PD47 (alendronate/Zwitterionic)=138.0 nm (0.079), −238±0.907 mV
PD48 (Zwitterionic)=190.9 nm (0.063); −20.1±0.666 mV Example 4

Colloids can be stabilized by two different mechanisms (or a combination thereof): electrostatic stabilization and steric stabilization.

If electrostatic repulsion of the particles is the main contributor then as a rule of thumb a zeta potential stronger than about 30 mV leads to a stable dispersion. For such a situation the colloid is more stable the further away it is formulated from the isoelectric point. It is formulated with a charge close to zero, then the particles are no longer be repelled strongly, and start to aggregate over time. B: If steric stabilization of the particles is the main driving force, then there is no rule of thumb for zeta potential. With these systems, even a formulation of near zero zeta potential can be stable, because it is not the charge of the particles, but rather the excluded volume interaction that keeps particles from sticking to each other. Of course even then, additional charge (e.g., slightly stronger zeta potential) helps contribute to the stability of the dispersion.

There should be no change of the isoelectric point for nanoparticles of different size, provided that all other conditions (surface characteristics, buffer, ionic strength, counter ions, pH, etc.) are the same. The zeta potential is not a parameter of the nanoparticle but rather a parameter describing the system of 'nanoparticle in dispersion'.

Example 5

Other exemplary zwitterionic molecules useful in the particles are shown below. N,N-Dimethyl, N-(2-Ethyl phosphate ethyl)-aminopropyl-trimethyoxysilane (DMPAMS)

Scheme 1. Synthesis Process of DMPAMS

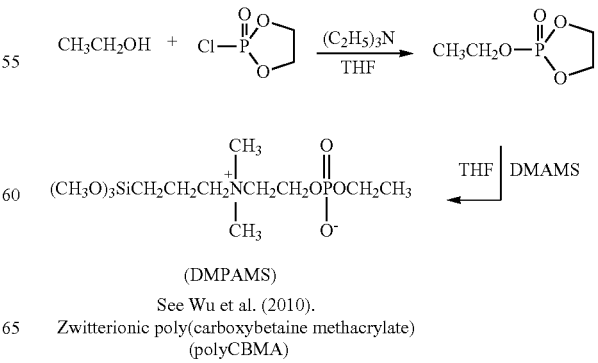

(DMPAMS)
See Wu et al. (2010).
Zwitterionic poly(carboxybetaine methacrylate) (polyCBMA)

Scheme 1

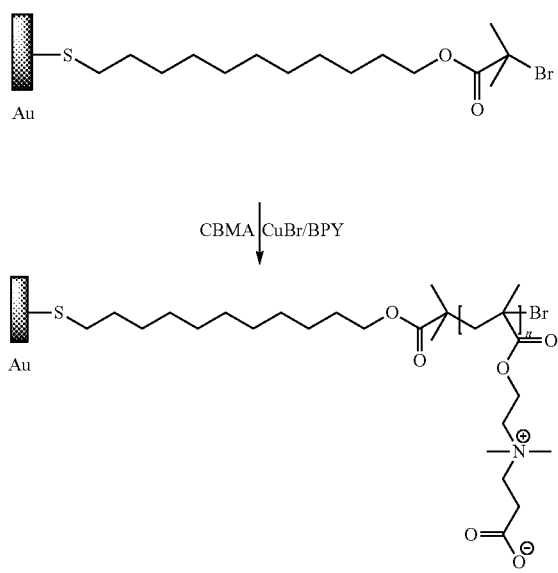

See Zhang et al. (2006)

Other zwitterionic groups that may be incorporated are: ammoniophosphates (phosphobetaines or lecithin analogues) and XIV, ammoniophosphonates (phosphonobetaines) II, IV and XV, ammoniophosphinates (phosphinobetaines) III, ammoniosulfonates (sulfobetaines) V and XVI, ammoniosulfates VI and XVII, ammoniocarboxylates (carbo- or carboxybetaines)VII, X, XI, XVIII and XXI, ammoniosulfonamides VIII, ammoni-sulfon-imides IX, guanidiniocarboxylates (asparagine analogs) X, pyridiniocarboxylates XI, ammonio(alkoxy)dicyanoethenolates XII, ammonioboronates XIII, sulfoniocarboxylates XIX, phosphoniosulfonates XX, phosphoniocarboxylates XXI, squaraine dyes XXII, oxypyridine betaines XXIII and XXIV.

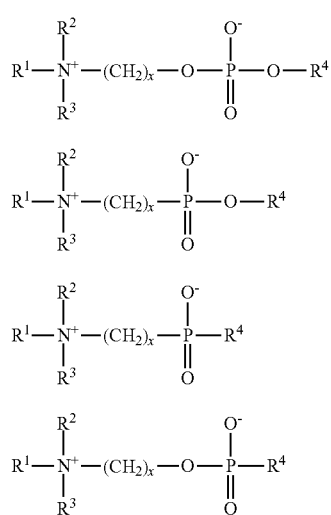

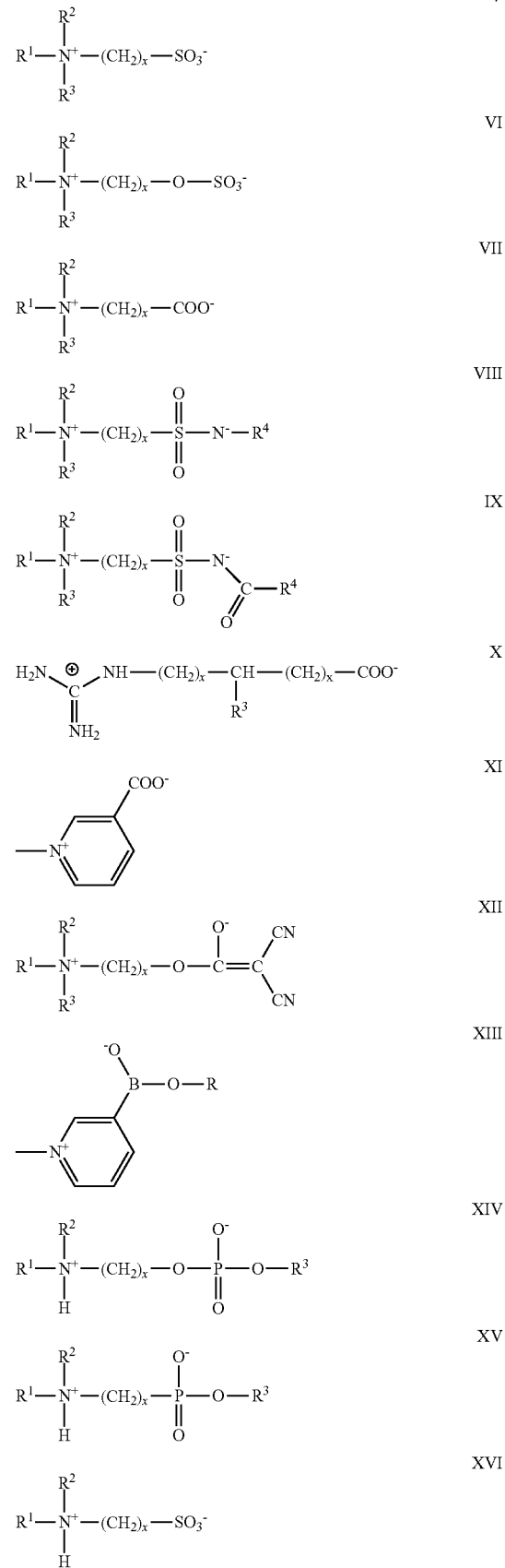

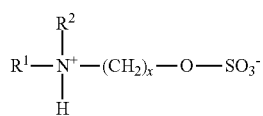 XVII

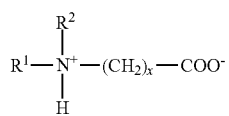 XVIII

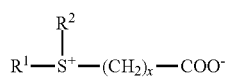 XIX

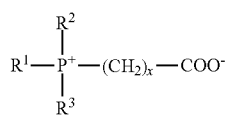 XX

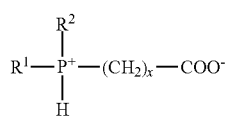 XXI

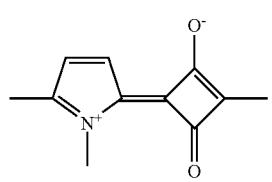 XXII

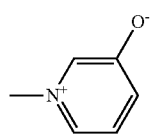 XXIII

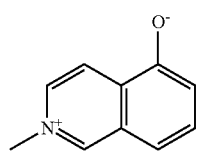 XXIV

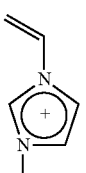 9

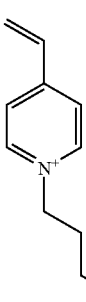 10, 11, 12

Exemplary zwitterionic monomers suited for free radical polymerization are shown above. Top row: sulfobetaines based on vinylimidazol, vinylpyridine, styrene, methacrylate, and isocyanide; Central row: carboxybetaines based on vinylimidazole, acrylamide, methacrylamide, isobutylene, and diallylamine; Bottom row: various polymerizable zwitterions derived from phosphatidylcholine, condensed hydroxypyridines, ammoniosulfonamide, ammoniosulfonimide, alkoxydicyanoethenolates, and sulfoniocarboxylate.

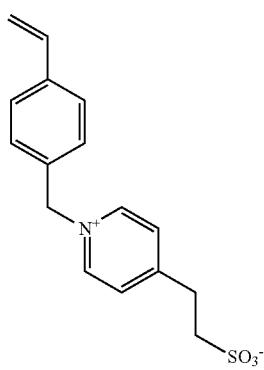
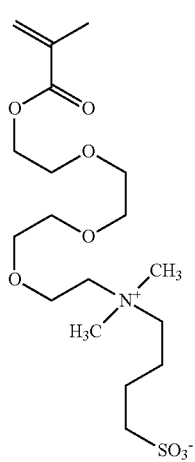
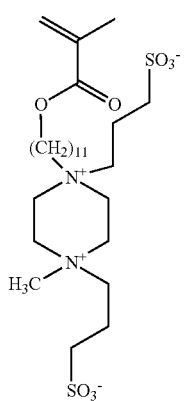
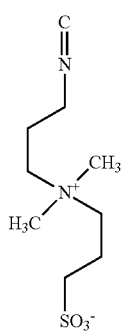
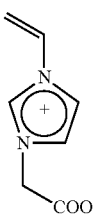
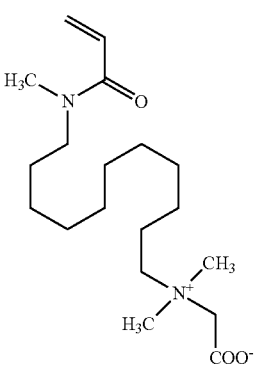
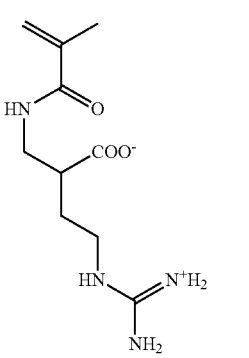
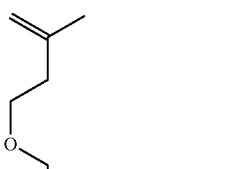

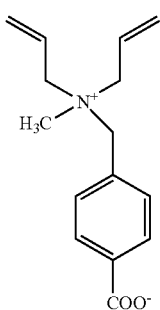
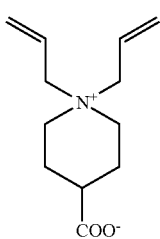
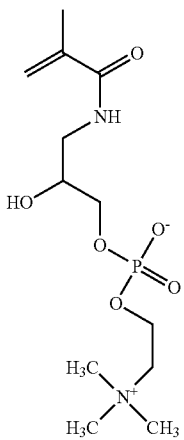
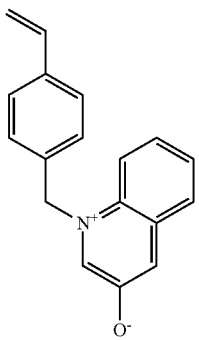
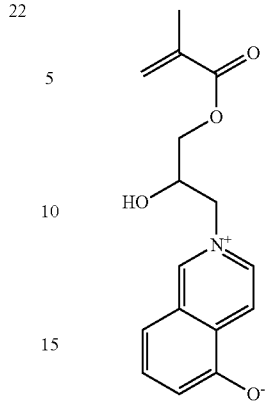
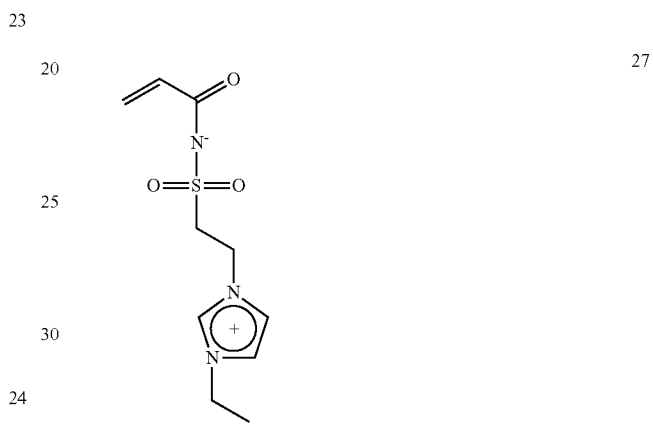
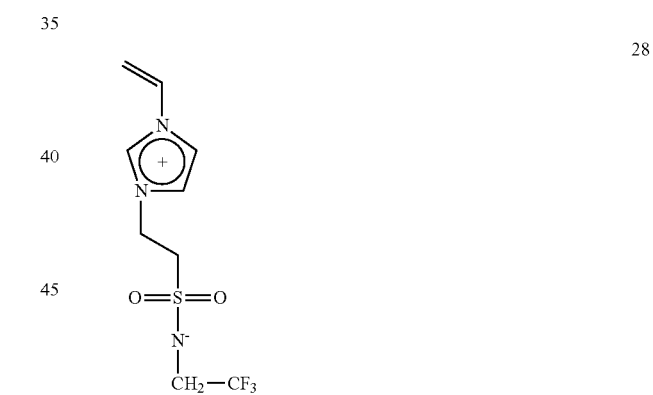
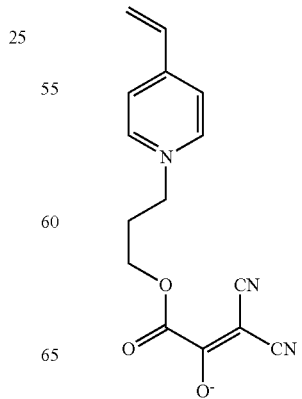

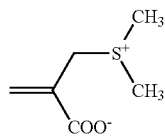

See Laschewsky (2014).

Example 6

Exemplary embodiment include a bone-cell targeting protocell comprising a mesoporous silica nanoparticle (MSNP) with a supported lipid bilayer coating said nanoparticle, at least one bisphosphonate moiety conjugated to the surface of the lipid bilayer and at least one cargo selected from the group consisting of at least one anticancer agent, a DNA or RNA compound that produces an anticancer agent in situ, at least one reporter which binds to cancer cells or tissue and mixtures thereof. In one embodiment, said anticancer agent is an anticancer small molecule, an anticancer RNA molecule, an anticancer peptide or a mixture thereof. In one embodiment, said anticancer RNA molecule is a small interfering RNA (siRNA), a small hairpin RNA (shRNA), a microRNA or a mixture thereof. In one embodiment, said anticancer agent is an anticancer small molecule. In one embodiment, said anticancer agent is a small interfering RNA. In one embodiment, said anticancer agent is an anticancer peptide. In one embodiment, said anticancer agent is a mixture of at least one anticancer small molecule and at least one siRNA. In one embodiment, said anticancer agent further includes at least one anticancer peptide. In one embodiment, said bisphosphonate moiety is obtained from a bisphosphonate molecule according to the chemical structure:

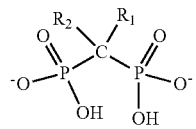

wherein $R_1$ is H, OH or halogen and $R_2$ is halogen, $C_1$-$C_6$ alkyl, $C_1$-$C_6$ alkylene amine, $C_1$-$C_6$ alkylene mono- or dialkyl amine, an optionally substituted thiophenyl group, an alkylene heteroaryl, or a $C_0$-$C_6$ alkylene carboxylic acid group, where the carboxylic acid group is substituted anywhere along the alkylene chain. In one embodiment, said bisphosphonate molecule is selected from the group consisting of etidronate, clodronate, tiladronate, pamidronate, neridronate, olpadronate, alendronate, ibandronate, risedronate and zoledronate. In one embodiment, said bisphosphonate molecule is pamidronate, neridronate or alendronate. In one embodiment, the protocell further comprises at least one cell penetrating peptide, a cell targeting peptide and/or a double stranded linear DNA or a plasmid DNA, wherein one of said DNA cargo components is optionally conjugated further with a nuclear localization sequence. In one embodiment, the bisphosphonate molecule is optionally conjugated to the MSNP. In one embodiment, the bisphosphonate molecule is conjugated solely to the lipid bilayer. In one embodiment, the bisphosphonate molecule is conjugated to the MSNP and to the lipid bilayer. In one embodiment, said cargo is or includes a reporter. In one embodiment, said reporter is an imaging agent. In one embodiment, said imaging agent is a fluorescent peptide. In one embodiment, said imaging agent is a fluorescent dye. In one embodiment, said anticancer agent is an anticancer small molecule. In one embodiment, said anticancer agent is a microtubule-stabilizing agent, microtubule-disruptor agent, an alkylating agent, air antimetabolite, an epidophyliotoxin, an antineoplastic enzyme, a topoisomerase inhibitor, an inhibitor of cell cycle progression or a platinum coordination complex. In one embodiment, said anticancer agent is a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor or a VEGF trap antibody. In one embodiment, said anticancer agent is everolimus, trabectedin, abraxane, TLK 286, AV-299, DN-101, pazopanib, GSK690693, TTA 744, ON 0910,Na, AZD 6244 (ARRY-142886; AMN-107, TK.I-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, dasatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespen, Rta 744, Sdx102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-I H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrozole, exemestane, letrozole, DES (diethylstilbestrol), estradiol, estrogen, conjugated estrogen, bevacizumab, IMC-1C11, CHIR-258,); 3-(5-(methylsulfonylpiperadinemethyl)-indolylj-quinolone, vatalanib, AG-013736, A VE-0005, the acetate salt of [D-Ser(Bu t) 6,Azgly 10] (pyro-Glu-His-Trp-Ser-Tyr-D-Ser(Bu t)-Leu-Arg-Pro-Azgly-NH$_2$ acetate [$C_{59}H_{84}N_{18}Oi_4$-($C_2H_4O_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165,HKI-272, erlotinib, lapatinib, canertinib, ABX-EGF antibody, erbifux, EKB-569, PKI-166, GW-572016, lonafamib, BMS-214662, tibifamib; amifostine, NVP-LAQ824, suberoyl anilide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mercaptopurine, deoxycoformycin, calcitriol, varubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxifene, spironolactone, finasteride, cimetidine, trastuzumab, denileukin diftitox,gefitinib, bortezomib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasoloxifene, idoxilene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD00I, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, etidronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof. In one embodiment, said lipid bilayer comprises at least one lipid selected from the group consisting of 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (D PPE), l,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino)lauroyl]-sn-Glycero-3-Phosphocholine (18: 1-12:0 NBD PC), 1-palmitoyl-2-{12-[(7-nitro-2-1,3-benzoxadiazol-4-yl)amino)lauroyl}-sn-glycero-3-phosphocholine (16:0-12:0 NBD PC), pegylated 1,2-distearoyl-sn-glycero-3-phosphoethanolamine (PEG-DSPE), pegylated 1,2-dioleoyl-sn-glycero-3-phosphoethanolamine (PEG-DOPE), pegylated 1,2-dipalmitoyl-sn-glycero-3-phosphoethanolamine (PEG-DPPE), and pegylated 1,2-dimyristoyl-sn-glycero-3-phosphoethap.olamine (PEG-DMPE), among others, including a pegylated ceramide (e.g. Noctanoyl-sphingosine-1-succinylmethoxy-PEG, N-palmitoyl-sphingosine-1-succinylmethoxy-PEG, cholesterol and mixtures/combinations thereof. In one embodiment, said lipid bilayer comprises a mixture of DSPC, DOPE and Cholesterol; DSPC, DOPE, Cholesterol and DSPE-PEG 2000 or DSPC, DSPE, Cholesterol and DSPE-PEG 2000. In one embodiment, said lipid bilayer is a mixture of DSPC, DOPE and Cholesterol; DSPC, DOPE, Cholesterol and DSPE-PEG 2000; or DSPC, DSPE, Cholesterol and DSPE-PEG 2000.

Further provided is a pharmaceutical composition comprising a population of the protocells in combination with a pharmaceutically acceptable carrier, additive and/or excipient. Also provided is a method of treating cancer in a patient in need comprising administering to said patient a therapeutically effective number of the protocells. In one embodiment, said cancer is bone cancer or metastatic bone cancer.

In addition, a method of diagnosing cancer in a patient suspected of being at risk for bone cancer or metastatic bone cancer is provided. The method includes administering to said patient an effective population of the protocells which contain a reporter as cargo and bind to or are incorporated into cancer cells or tissue in said patient, determining the number or amount of said protocells or said reporters which bind to or are incorporated into bone tissue of said patient and comparing the number or amount of said protocells or said reporters which bind to or are incorporated into said bone tissue in said patient to a standard wherein a level above a standard obtained from one or more healthy patients is indicative of the existence of cancer and a level substantially below a standard obtained from one or more patients having bone cancer is indicative of the absence of bone cancer, including metastatic bone cancer in said patient.

A method of monitoring anticancer therapy in a patient in need is provided. The method comprises administering to said patient at least twice at different times during anticancer therapy of said patient an effective amount of a population of the MSNPs which bind to or are incorporated into bone tissue and which contain a reporter, determining the number or amount of said MSNPs or said reporter which bind to or are incorporated into bone tissue in said patient at said times and comparing the binding of or incorporation of said MSNPs or said diagnostic agent into bone tissue at said different times to determine whether therapy in said patient is treating said cancer. In one embodiment, the patient is administered said MSNPs at about the same time that therapy is commenced and at least one time thereafter, determining the number or amount of said MSNPs or said reporters which bind to or are incorporated into bone tissue in said patient at the start of therapy and after a period of therapy, wherein a reduction in the binding of said MSNPs and/or said reporter after a period of treatment is indicative that the therapy is treating said cancer.

Example 7

Exemplary embodiment include a bone-cell targeting nanoparticle comprising a mesoporous silica nanoparticle (MSNP), at least one bisphosphonate moiety conjugated to the surface of the nanoparticle and at least one cargo selected from the group consisting of at least one anticancer agent, a DNA or RNA compound that produces an anticancer agent in situ, at least one reporter which binds to cancer cells or tissue and mixtures thereof. In one embodiment, said anticancer agent is an anticancer small molecule, an anticancer RNA molecule, an anticancer peptide or a mixture thereof. In one embodiment, said anticancer RNA molecule is a small interfering RNA (siRNA), a small hairpin RNA (shRNA), a microRNA or a mixture thereof. In one embodiment, said anticancer agent is an anticancer small molecule. In one embodiment, said anticancer agent is a small interfering RNA. In one embodiment, said anticancer agent is an anticancer peptide. In one embodiment, said anticancer agent is a mixture of at least one anticancer small molecule and at least one siRNA. In one embodiment, said anticancer agent further includes at least one anticancer peptide. In one embodiment, said bisphosphonate moiety is obtained from a bisphosphonate molecule according to the chemical structure:

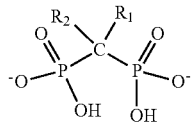

wherein $R_1$ is H, OH or halogen and $R_2$ is halogen, $C_1$-$C_6$ alkyl, $C_1$-$C_6$ alkylene amine, $C_1$-$C_6$ alkylene mono- or dialkyl amine, an optionally substituted thiophenyl group, an alkylene heteroaryl, or a $C_0$-$C_6$ alkylene carboxylic acid group, where the carboxylic acid group is substituted anywhere along the alkylene chain. In one embodiment, said bisphosphonate molecule is selected from the group consisting of etidronate, clodronate, tiladronate, pamidronate, neridronate, olpadronate, alendronate, ibandronate, risedronate and zoledronate. In one embodiment, said bisphosphonate molecule is pamidronate, neridronate or alendronate. In one embodiment, the MSNP further comprises at least one cell penetrating peptide, a cell targeting peptide and/or a double stranded linear DNA or a plasmid DNA, wherein one of said DNA cargo components is optionally conjugated further with a nuclear localization sequence. In one embodiment, said cargo is or includes a reporter. In one embodiment, said reporter is an imaging agent. In one embodiment, said imaging agent is a fluorescent peptide. In one embodiment, said imaging agent is a fluorescent dye. In one embodiment, said anticancer agent is an anticancer small molecule. In one embodiment, said anticancer agent is a microtubule-stabilizing agent, microtubule-disruptor agent, an alkylating agent, an antimetabolite, an epidophyllotoxin, an antineoplastic enzyme, a topoisomerase inhibitor, an inhibitor of cell cycle progression or a platinum coordination complex. In one embodiment, said anticancer agent is a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a local adhesion kinase inhibitor, a Map kinase kinase (mek) inhibitor or a VEGF trap antibody. In one embodiment, said anticancer agent is everolimus, trabectedin, abraxane, TLK 286, AV-299, DN-101, pazopanib, GSK690693, RTA 744, ON 0910.Na, AZD 6244 (ARRY-142886), AMN-107, TK.I-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, dasatanib, panitumumab, amrubicin, oregovomab, Lep-etu, nolatrexed, azd2171, batabulin, ofatumumab, zanolimumab, edotecarin, tetrandrine, rubitecan, tesmililene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_f$ KRX-0402, lucanthone, LY 317615, neuradiab, vitespen, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-I H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrozole, exemestane, letrozole, DES(diethylstilbestrol), estradiol, estrogen, conjugated estrogen, bevacizumab, IMC-1C11, CHIR-258,); 3-(5-(methylsulfonylpiperadinemethyl)-indolylj-quinolone, vatalanib, AG-013736, A VE-0005, the acetate salt of [D-Ser(Bu t) 6,Azgly 10 (pyro-Glu-His-Trp-Ser-Tyr-D-Ser(Bu t)-Leu-Arg-Pro-Azgly-NH$_2$ acetate [$C_{59}H_{84}N_{18}Oi_4$-($C_2H_4O_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatinib, canertinib, ABX-EGF antibody, erbifux, EKB-569, PKI-166, GW-512016, lonafamib, BMS-214662, tipifamib; amifostine, NVP-LAQ824, suberoyl anilide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxifene, spironolactone, finasteride, cimetidine, trastuzumab, denileukin diftitox,gefitinib, bortezomib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD00I, ABT-578, BC-210, LY294002, LY292223, LY292696, LY293684, LY293646, wortmannin, ZM336372, L-779,450, PEGTIgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, etidronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

Further provided is a pharmaceutical composition comprising a population of the MSNPs in combination with a pharmaceutically acceptable carrier, additive and/or excipient. Also provided is a method of treating cancer in a patient in need comprising administering to said patient a therapeutically effective number of the MSNPs. In one embodiment, said cancer is bone cancer or metastatic bone cancer.

In addition, a method of diagnosing cancer in a patient suspected of being at risk for bone cancer or metastatic bone cancer is provided. The method includes administering to said patient an effective population of the MSNPs which contain a reporter as cargo and bind to or are incorporated into cancer cells or tissue in said patient, determining the number or amount of said MSNPs or said reporters which bind to or are incorporated into bone tissue of said patient and comparing the number or amount of said MSNPs or said reporters which bind to or are incorporated into said bone tissue in said patient to a standard wherein a level above a standard obtained from one or more healthy patients is indicative of the existence of cancer and a level substantially below a standard obtained from one or more patients having bone cancer is indicative of the absence of bone cancer, including metastatic bone cancer in said patient.

A method of monitoring anticancer therapy in a patient in need is provided. The method comprises administering to said patient at least twice at different times during anticancer therapy of said patient an effective amount of a population of the MSNPs which bind to or are incorporated into bone tissue and which contain a reporter, determining the number or amount of said MSNPs or said reporter which bind to or are incorporated into bone tissue in said patient at said times and comparing the binding of or incorporation of said MSNPs or said diagnostic agent into bone tissue at said different times to determine whether therapy in said patient is treating said cancer. In one embodiment, the patient is administered said MSNPs at about the same time that therapy is commenced and at least one time thereafter, determining the number or amount of said MSNPs or said reporters which bind to or are incorporated into bone tissue in said patient at the start of therapy and after a period of therapy, wherein a reduction in the binding of said MSNPs and/or said reporter after a period of treatment is indicative that the therapy is treating said cancer.

REFERENCES

Ashley, et al., *Nature Materials,* 10:389 (2011).
Bachler et al., *Int. J. Nanomedicine,* 8:3365 (2013).
Bianco et al., *Urology,* 66:83 (2005).
Bisanz et al., *Mol. Ther.,* 12:634 (2005).
Canadian Cancer Society's Advisory Committee on Cancer Statistics. Canadian Cancer Statistics (2014) (Toronto, ON).
Caroll et al., *Langmuir,* 25:13540 (2009),
Cesta, *Toxicol. Pathol.,* 34:455 (2006).
Chun et al., *World J. Urol.,* 24:273 (2006).
Edginton et al., *Expert Opin. Drug Metab. Toxicol.,* 4:1143 (2008).
Han et al., *Urol. Clin. North Am.,* 28:555 (2001).
Heidenreich et al., *Eur. Urol.,* 65:467 (2014).
Kupelian et al., *Int. J. Radial. Oncol. Biol. Phys.* 37(5): 1043 (1997).
Laschewsky, *Polymers,* 6:1544 (2014).
Li et al., *ACS Nano.,* 4:6303 (2010).
Lin et al., *J. Am. Chem. Soc.,* 133:20444 (2011).
Liu, et al., *Chem. Comm.,* 5100-5102 (2009).
Liu et al., *J. Amer. Chem. Soc.,* 131:1354 (2009).
Liu et al., *J. Amer. Chem. Soc.,* 131:7567 (2009).
Lu, et al., *Nature,* 398:223(1999).
Maharaj et al., *AAPS J.,* 15(2):455 (2013).
McNamara et al., *Nat. Biotechnol.,* 24:1005 (2006).
Moss and Siccardi, *Br. J. Pharmacol.,* doi: 10.IIII/bph.12604 (2014).
Offinan and Edginton, *J. Pharmacokinet. Pharmacodyn.* doi: 10.1007/s10928-015-9406-4 (2015).
Ortiz and Lin, *Recent Results Cancer Res.,* 192:225 (2012).
Parker et al., *N. Engl. J. Med.,* 369:213 (2013).
Parrott et al., *Clin. Pharmacokinet.,* 52:673 (2013).
Pound et al., *JAMA,* 281:1591 (1999).
Roudier et al., *J. Urol.,* 180:1154 (2008).
Russell et al., *Ann. N.Y. Acad. Sci.,* 1117:209 (2007).
Seaton et al., *JR Soc. Interface.* 7:S119 (2010).
Shah and Betts, *J. Pharmacokinet. Pharmacodyn.,* 39:67 (2012).
Shirley and McCormack, *Drugs,* 74:579 (2014).
Suva et al., *Nat. Rev. Endocrinol* 7:208 (2011).
Taxotere Product Monograph (2013) 58.
Townson et al., *J. Am. Chem. Soc.,* 135:16030 (2013).
Tran et al., *Science,* 324:787 (2009).
Wu et al., *ACS Appl. Mat. & Interfaces,* 2.10:2781 (2010).
Zhang et al., *Biomolecules,* 7:3311 (2006).

All publications, patents and patent applications are incorporated herein by reference. While in the foregoing specification, certain embodiments have been described, and many details have been set forth for purposes of illustration, it will be apparent to those skilled in the art that the invention is susceptible to additional embodiments and that certain of the details herein may be varied considerably without departing from the basic principles of the disclosure.

What is claimed is:

1. A bone-cell targeting mesoporous silica nanoparticle (MSNP), the MSNP comprising a silane coating comprising a plurality of water soluble bisphosphonate moieties linked to the coating, and optionally further comprising at least one cargo selected from the group consisting of at least one non-bisphosphonate anticancer agent, a reporter, and a combination thereof, wherein the bone-cell targeting MSNP is prepared by
   (a) contacting a water soluble bisphosphonate and an epoxysilane to provide a water soluble bisphosphonate moiety linked to the silane; and
   (b) combining the water soluble bisphosphonate moiety linked to the silane with MSNPs and a zwitterionic silane to provide for silane coated MSNP comprising a plurality of the water soluble bisphosphonate moieties linked to the coating, wherein the bisphosphonate has the structure

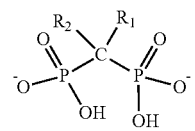

or a salt or ionic form thereof,
wherein $R_1$ is H, OH, or halogen, and $R_2$ is $-NH_2$ or a $C_1$-$C_6$ monoalkyl amine.

2. The nanoparticle of claim 1 wherein the epoxysilane comprises (3-glycidyloxypropyl)trimethoxysilane.

3. The nanoparticle according to claim 1 wherein said non-bisphosphonate anticancer agent is present and Is selected from the group consisting of an anticancer small molecule, an anticancer RNA molecule, a DNA that produces an anti-cancer effect in situ, an anticancer peptide and mixtures thereof.

4. The nanoparticle according to claim 3 wherein said anticancer RNA molecule is a small interfering RNA (siRNA), a small hairpin RNA (shRNA), a microRNA or a mixture thereof, or wherein said non-bisphosphonate anticancer agent comprises a mixture of at least one anticancer small molecule and at least one siRNA.

5. The nanoparticle according to claim 1, wherein said bisphosphonate molecule is selected from the group consisting of pamidronate, neridronate, alendronate, and combinations thereof.

6. The nanoparticle according to claim 1 wherein said cargo is present and includes a reporter.

7. The nanoparticle according to claim 6 wherein said reporter is an imaging agent, a fluorescent peptide or fluorescent dye.

8. The nanoparticle according to claim 1 wherein said non-bisphosphonate anticancer agent Is present and is a microtubule-stabilizing agent, a microtubule-disruptor agent, an alkylating agent, an antimetabolite, an epipodophylotoxin, an antineoplastic enzyme, a topoisomerase inhibitor, an inhibitor of cell cycle progression, a platinum coordination complex, a FLT-3 inhibitor, a VEGFR inhibitor, an EGFR TK inhibitor, an aurora kinase inhibitor, a PK-1 modulator, a Bel-2 inhibitor, an HDAC inhibitor, a c-MET inhibitor, a PARP inhibitor, a Cdk inhibitor, an EGFR TK inhibitor, an IGFR-TK inhibitor, an anti-HOF antibody, a PB kinase inhibitors, an AKT inhibitor, a SAK/STAT inhibitor, a checkpoint-I or 2 inhibitor, a focal adhesion kinase inhibitor, a Map kinase (mek) inhbitor, a VEGF trap antibody, everolimus, trabectedin, abraxane, TLK 286 (canfosfamide), AV-299 (ficlatuzumab), DN-101 (calcitriol), pazopanib, GSK690693 (442-(4-amino-1,2,5-oxadiazol-3-yl)-1-ethyl-7-4(3S)-3-piperidinylmethoxy]-1H-imidazo[4,5-c]pyridin-4-yl]-2-methyl-3-butyn-2-ol), RTA 744 (berubicin), AZD 6244 (selumetinib), ANN-107 (nilotinib), TKI-258 (dovitinib), GSK461364 ((R)-5-[6[(4-methyl-1-piperazinyl)methyl]-1H-benzimidazol-1-yl]-3-[(1r)-1-42-(trifluoromethyl)phenyl]ethoxy]-2-thiophenecarboxamide), AZD 1152 (barasertib), enzastaurin, vandetanib, ARQ-197 (tivantinib), MK-0457 (tozasertib), MLN8054 (4-9 Chloro-7-(2,6-difluorophenyl)-5H-pyrimido[5,4-d][2]benzazepin-2-yl]amino]benzoic acid), PHA-739338 (danusertib), R-763 (cenisertib), [[AT-9263,]] pemetrexed, erlotinib, panitumumab, amrubicin, oregovomab, Lep-etu (liposomal paclitaxel), nolatrexed, azd2171, batabulin, ofatumumab, zanclimumab, edotecarin, tetrandrine, rubitecan, tesmilifene, oblimersen, ticilimumab, ipilimumab, gossypol, 131-1-TM-601 (Iodine-131 substituted chlorotoxin), CC 8490 (custirsen), cilengitide, gimatecan, IL13-PE38QOR (human IL-13 conjugated with a truncated *Pseudomonas* exotoxin), INO 1001 (N-[3-(4-Morpholinyl)propyl]-5-oxo-6,11-dihydro-5H-indeno[1,2-c]is oquinoline-9-sulfonamide), lucanthone, LY 317615 (enzastaurin), neuradiab, vitespen, Sdx 102 (L-Alanosine), talampanel, atrasentan, romidepsin, sunitinib, 5-flucrouracil, vorinostat, etoposide, gemcitabine, doxorubicin, liposomal doxorubicin, 5'-deoxy-5-fluorouridine, vincristine, temozolomide, ZK-304709 ((S)-4-((5-bromo-4-((1-hydroxypropan-2-yl)amino)pyrimidin-2 yl)amino)benzenesulfonamide), selici- clib; PD0325901 (mirdametinib), capecitabine, L-Glutamic acid, N-[4-[2-(2-amino-4,7-dihydro-4-oxo-1 H-pyrrolo[2,3-d]pyrimidin-5-yl]ethyl]benzoyl]-disodium salt hepahydrate, camptothecin, PEG-labeled irinotecan, tamoxifen, toremifene citrate, anastrozole, exemestane, letrozole, DES (diethylstilbestrol), estradiol, estrogen, conjugated estrogen, bevacizumab, NC-1C11 (antibody against human vascular endothelial growth factor 2), 3-[5-(methylsulfonylpiperadinemethyl)-indolyl]-quinolone, vatalanib, AG-013736 (axitinib), AVE-0005, (pyro-Glu-His-Trp-Ser-Tyr-D-Ser(Bu t)-Leu-Arg-Pro-Azgly-NH2 (SEQ D NO: 9) acetate $[C_{59}H_{84}N_{18}O_{14}\text{-}C_2H_4O_2]_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714 (2-Methoxy-N-[((2E)-3-[4-[[3-methyl-4-[((6-methyl-3-pyridinyl)oxy]phenyl]amino]-6-quinazolinyl]-2-propen-1-yl]acetamide), TAK-165 (mubritinib), HKI-272 (neratinib), erlotinib, lapatinib, canertinib, ABX-EGF antibody (panitumumab), cetuximab, lonafamib, BMS-214662 ((3R)-2,3,4,5-Tetrahydro-1-(1H-Imidazol-4-ylmethyl)-3-(phenylmethyl)-4-(2-thienylsulfonyl)-1H-1,4-benzodiazepine-7-carbonitrile), tipifarnib, amifostine, NVP-LAQ824 (dacinostat), suberoyl anilide hydroxamic acid, valproic acid, trichostatin A, FK-228 (romidepsin), sorafenib, KRN951 (tivozanib), aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbesirol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, aracil mustard, estramustine, altretamine, floxuridine, 5-deoxyuridine, cytosine arabinoside, 6-mercaptopurine, deoxycoformycin, calcitriol, valrubicin, mithramycin, vinblastine, vinorelbine, topotecan, razoxin, marimastat, COL-3 (incyclinide), neovastat, BMS-275291 (rebimastat), squalamine, endostatin, SU5416 (semaxanib),EMD121974 (cilengitide), interleukin-12, IM862 (glufanide disodium), angiostatin, vitaxin, droloxifene, idoxifene, spironolactone, finasteride, cimetidine, trastuzumab, denileukin diftitox, gefitinib, bortezomib, paclitaxel, cremophor-free paclitaxel, docetaxel, epithilone B, BMS-247550 (ixabepilone), BMS-310705 (21-aminoepothilone B), droloxifene, 4-hydroxytamoxifen, pipendoxifene, ERA-923 (pipendoxifene), arzoxifene, fulvestrant, acolbifene, lasofoxifene, idoxifene, TSE-424 (bazedoxifene), HMR-3339 (4-Chloro-11b-(4-(2-(diethylamino)ethoxyphenyl)-estra-1,3,5(10)-triene-3,17b-diol), PTK787/ZK 222584 (1-[4-chloroanilino]-4-14-pyridylmethyl] phthalazine succinate), VX-745 (neflamapimod), rapamycin, 40-O-(2-hydroxyethy)-rapamycin, temsirolimus, AP-23573 (ridaforolimus), ABT-578 (zotarolimus), LY294002 (2-(4-Morpholinyl)-8-phenyl-4H-1-benzopyran-4-one), LY292223 ((2S,4R)-4-Mercapto-2-(2,4,5-trifluoro-benzyloxymethyl)-pyrolidine-1-carboxylic acid 2-methoxycarbonyl-phenyl ester), LY292696 (2-(4-Thiomorpholinyl)-4H-1-benzopyran-4-one), LY293684 & Morpholinyl)-1H-naphtho[2,1-b]pyran-1-one), LY293646 (2-(4-Morpholinyl)-4H-naphtho[1,2-b]

pyran-4-one), wortmannin, ZM336372 (3-(Dimethylamino)-N-13-l(4-hydroxybenzoyl)aminol-4-methylphenyl]benzamide), L-779,450 (2-chloro-5-(2-phenyl-5-(pyridin-4-yl)-1H-Imidazol-4-yl)phenol), PEG-filgrastim, darbepoetin, erythropoietin, granulocyte colony-stimulating factor, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, etidronate, mitotane, cyclosporine, liposomal daunorubicin, Edwina-asparaginase, strontium 89, casopitant, netupitant, a NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochiorperazine, granisetron, ondansetron, dolasetron, tropisetron, pegfilgrastim, erythropotetin, epoetin alfa, darbepoetin alfa and mixtures thereof.

9. The nanoparticle of claim 1 wherein the zwitterionic silane comprises 3-{[dimethyl(3-trimethoxysilyl)propyl]ammonio}propane-1-sulfonate.

10. A method comprising administering an effective number of nanoparticles according to claim 1 to a Patient.

11. The method according to claim 10 wherein said patient has a cancer which is bone cancer or metastatic bone cancer.

* * * * *

UNITED STATES PATENT AND TRADEMARK OFFICE
CERTIFICATE OF CORRECTION

PATENT NO. : 11,672,866 B2
APPLICATION NO. : 16/068235
DATED : June 13, 2023
INVENTOR(S) : Durfee et al.

It is certified that error appears in the above-identified patent and that said Letters Patent is hereby corrected as shown below:

On the Title Page

On page 5, in Column 1, under item (56) "Other Publications", Line 41, delete "Responsed" and insert --Response-- therefor On page 5, in Column 2, under item (56) "Other Publications", Line 9, delete "t" and insert --to-- therefor On page 6, in Column 1, under item (56) "Other Publications", Line 11, delete "17/264,452," and insert --16/828,137,-- therefor On page 6, in Column 1, under item (56) "Other Publications", Line 13, delete "17/264,452," and insert --16/976,651,-- therefor On page 6, in Column 1, under item (56) "Other Publications", Line 25, delete "15/858,923," and insert --15/023,093-- therefor On page 8, in Column 1, under item (56) "Other Publications", Line 1, delete "Nanoporaus" and insert --Nanoporous-- therefor On page 8, in Column 1, under item (56) "Other Publications", Line 2, delete "Bllayen" and insert --Bilayer-- therefor On page 8, in Column 1, under item (56) "Other Publications", Line 56, delete "Microparitcles" and insert --Microparticles-- therefor On page 8, in Column 2, under item (56) "Other Publications", Line 31, delete "nanopartilce" and insert --nanoparticle-- therefor Signed and Sealed this
Twenty-ninth Day of October, 2024

Katherine Kelly Vidal
*Director of the United States Patent and Trademark Office*

On page 8, in Column 2, under item (56) "Other Publications", Line 55, delete "Papilloma virus" and insert --Papillomavirus-- therefor On page 8, in Column 2, under item (56) "Other Publications", Line 60, delete "Excherichia" and insert --Escherichia-- therefor On page 9, in Column 1, under item (56) "Other Publications", Line 27, delete "Particulat" and insert --Particulate-- therefor On page 9, in Column 1, under item (56) "Other Publications", Line 28, delete "Functionalitiy"," and insert --Functionality",-- therefor On page 9, in Column 1, under item (56) "Other Publications", Line 34, delete "adva"," and insert --advances",-- therefor On page 9, in Column 1, under item (56) "Other Publications", Line 68, delete "gp 120.","  and insert --gp120.",-- therefor On page 10, in Column 1, under item (56) "Other Publications", Line 22, delete "(NW)" and insert --(NVV)-- therefor On page 10, in Column 1, under item (56) "Other Publications", Line 22, delete "cy1okine" and insert --cytokine-- therefor On page 10, in Column 2, under item (56) "Other Publications", Line 27, delete "Mitoxantrane"," and insert --Mitoxantrone",-- therefor On page 12, in Column 2, under item (56) "Other Publications", Line 8, delete "mesoporaus" and insert --mesoporous-- therefor On page 12, in Column 2, under item (56) "Other Publications", Line 17, delete "Sequence-Specitic" and insert --Sequence-Specific-- therefor In the Claims In Column 59, Line 61, in Claim 1, delete "by" and insert --by:-- therefor In Column 60, Line 65, in Claim 1, delete "Ionic" and insert --ionic-- therefor In Column 60, Line 66, in Claim 1, delete "Is" and insert --is-- therefor In Column 61, Line 4, in Claim 3, delete "Is" and insert --is-- therefor In Column 61, Line 25, in Claim 8, delete "Is" and insert --is-- therefor In Column 61, Line 32, in Claim 8, delete "PK-1" and insert --PIK-1-- therefor

CERTIFICATE OF CORRECTION (continued)
U.S. Pat. No. 11,672,866 B2

In Column 61, Line 37, in Claim 8, delete "inhbitor," and insert --inhibitor,-- therefor In Column 61, Lines 40-42, in Claim 8, delete "(442-(4-amino-1,2,5-oxadiazol-3-yl)-1-ethyl-7-4(3S)-3-piperidinylmethoxy]-1H-imidazo[4,5-c]pyridin-4-yl]-2-methyl-3-butyn-2-ol)," and insert --(4-[2-(4-amino-1,2,5-oxadiazol-3-yl)-1-ethyl-7-[(3S)-3-piperidinylmethoxy]-1H-imidazo[4,5-c]pyridin-4-yl]-2-methyl-3-butyn-2-ol),-- therefor In Column 61, Line 43, in Claim 8, delete "ANN-107" and insert --AMN-107-- therefor In Column 61, Lines 44-47, in Claim 8, delete "((R)-5-[6[(4-methyl-1-piperazinyl)methyl]-1H-benzimidazol-1-yl]-3-[(1r)-1-42-(trifluoromethyl)phenyl]ethoxy]-2-thioph-enecarboxamide)," and insert --((R)-5-[6-[(4-methyl-1-piperazinyl)methyl]-1H-benzimidazol-1-yl]-3-[(1r)-1-[2-(trifluoromethyl)phenyl]ethoxy]-2-thioph-enecarboxamide),-- therefor In Column 61, Lines 49-50, in Claim 8, delete "(4-9 Chloro-7-(2,6-difluorophenyl)-5H-pyrimido[5,4-d][2]benzazepin-2-yl]amino]benzoic acid)," and insert --(4-[9-Chloro-7-(2,6-difluorophenyl)-5H-pyrimido[5,4-d][2]benzazepin-2-yl]amino]benzoic acid),-- therefor In Column 61, Line 51, in Claim 8, after "(cenisertib),", delete "[[AT-9263,]]"

In Column 61, Line 55, in Claim 8, delete "ticilimumab," and insert --ticilimrumab,-- therefor In Column 61, Line 56, in Claim 8, delete "(Iodine-131" and insert --(iodine-131-- therefor In Column 61, Lines 66-67, in Claim 8, delete "((S)-4-((5-bromo-4-((1-hydroxypropan-2-yl)amino)pyrimidin-2 yl)amino)benzenesulfonamide)" and insert --((S)-4-((5-bromo-4-((1-hydroxypropan-2-yl)amino)pyrimidin-2-yl)amino)benzenesulfonamide)-- therefor In Columns 61-62, Lines 67, 1, in Claim 8, delete "seliciclib;" and insert --seliciclib,-- therefor In Column 62, Line 7, in Claim 8, delete "NC-1C11" and insert --IMC-1C11-- therefor In Column 62, Line 11, in Claim 8, delete "(SEQ D NO: 9)" and insert --(SEQ ID NO: 9)-- therefor In Column 62, Lines 16-18, in Claim 8, delete "(2-Methoxy-N-[((2E)-3-[4-[[3-methyl-4-[((6-methyl-3-pyridinyl)oxy]phenyl]amino]-6-quinazolinyl]-2-propen-1-yl]acetamide)," and insert --(2-Methoxy-N-[(2E)-3-[4-[3-methyl-4-[(6-methyl-3-pyridinyl)oxy]phenyl]amino]-6-quinazolinyl]-2-propen-1-yl]acetamide),-- therefor In Column 62, Line 18, in Claim 8, delete "TAK-165" and insert --TAK.-165-- therefor In Column 62, Lines 55-57, in Claim 8, delete "(4-Chloro-11b-(4-(2-(diethylamino)ethoxyphenyl)-estra-1,3,5(10)-triene-3,17b-diol)," and insert --(4-Chloro-11b-(4-(2-(diethylamino)ethoxy)phenyl)-estra-1,3,5(10)-triene-3,17b-diol),-- therefor

CERTIFICATE OF CORRECTION (continued)
U.S. Pat. No. 11,672,866 B2

In Column 62, Lines 57-58, in Claim 8, delete "(1-[4-chloroanilino]-4-14-pyridylmethyl] phthalazine succinate)," and insert --(1-[4-chloroanilino]-4-[4-pyridylmethyl] phthalazine succinate),-- therefor In Column 62, Line 66, in Claim 8, delete "&" and insert --(3-(4- -- therefor In Column 63, Lines 1-3, in Claim 8, delete "(3-(Dimethylamino)-N-13-1(4-hydroxybenzoyl)aminol-4-methylphenyl]benzamide)," and insert --(3-(Dimethylamino)-N-[3-[(4-hydroxybenzoyl)aminol-4-methylphenyl]benzamide),-- therefor In Column 63, Line 28, in Claim 10, delete "Patient." and insert --patient.-- therefor